US008697072B2

(12) United States Patent
Frank et al.

(10) Patent No.: US 8,697,072 B2
(45) Date of Patent: Apr. 15, 2014

(54) TARGETING ABCB5 FOR CANCER THERAPY

(75) Inventors: Markus H. Frank, Cambridge, MA (US); Natasha Y. Frank, Cambridge, MA (US); Mohamed H. Sayegh, Westwood, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 364 days.

(21) Appl. No.: 13/044,854

(22) Filed: Mar. 10, 2011

(65) Prior Publication Data

US 2011/0165149 A1 Jul. 7, 2011

Related U.S. Application Data

(62) Division of application No. 12/101,428, filed on Apr. 11, 2008, now Pat. No. 7,928,202.

(60) Provisional application No. 61/007,059, filed on Dec. 11, 2007, provisional application No. 60/923,128, filed on Apr. 12, 2007.

(51) Int. Cl.
*A61K 39/395* (2006.01)

(52) U.S. Cl.
USPC .................................... 424/133.1; 424/155.1

(58) Field of Classification Search
None
See application file for complete search history.

(56) References Cited

U.S. PATENT DOCUMENTS

| | | | |
|---|---|---|---|
| 4,382,441 A | 5/1983 | Svedman | |
| 4,587,101 A | 5/1986 | Marsoner et al. | |
| 4,817,594 A | 4/1989 | Juhasz | |
| 5,399,483 A | 3/1995 | Shibano et al. | |
| 5,565,354 A | 10/1996 | Ostberg | |
| 5,567,610 A | 10/1996 | Borrebaeck et al. | |
| 5,569,825 A | 10/1996 | Lonberg | |
| 5,571,893 A | 11/1996 | Baker et al. | |
| 5,759,570 A | 6/1998 | Arnold | |
| 5,833,641 A | 11/1998 | Curtis et al. | |
| 5,904,659 A | 5/1999 | Duarte et al. | |
| 6,071,267 A | 6/2000 | Zamierowski | |
| 6,420,622 B1 | 7/2002 | Johnston et al. | |
| 6,459,109 B2 | 10/2002 | Takeshita et al. | |
| 6,479,072 B1 | 11/2002 | Morgan et al. | |
| 6,632,656 B1 | 10/2003 | Thomas et al. | |
| 6,685,681 B2 | 2/2004 | Lockwood et al. | |
| 6,755,807 B2 | 6/2004 | Risk, Jr. et al. | |
| 6,767,194 B2 | 7/2004 | Jeon et al. | |
| 6,846,883 B2 | 1/2005 | Frank et al. | |
| 6,855,135 B2 | 2/2005 | Lockwood et al. | |
| 6,867,342 B2 | 3/2005 | Johnston et al. | |
| 6,899,873 B2 | 5/2005 | Ma et al. | |
| 7,202,346 B2 | 4/2007 | Payne et al. | |
| 7,928,202 B2 | 4/2011 | Frank et al. | |
| 8,076,091 B2 | 12/2011 | Frank et al. | |
| 2001/0007658 A1 | 7/2001 | Usala et al. | |
| 2002/0068913 A1 | 6/2002 | Fleischmann | |
| 2002/0115967 A1 | 8/2002 | Svedman | |
| 2002/0127736 A1 | 9/2002 | Chou et al. | |
| 2002/0150720 A1 | 10/2002 | Howard et al. | |
| 2004/0243073 A1 | 12/2004 | Lockwood et al. | |
| 2005/0004534 A1 | 1/2005 | Lockwood et al. | |
| 2005/0249728 A1 | 11/2005 | Singh et al. | |
| 2005/0251083 A1 | 11/2005 | Carr-Brendel et al. | |
| 2006/0177455 A1 | 8/2006 | Hoffee et al. | |
| 2008/0118432 A1 | 5/2008 | Bergstein et al. | |
| 2011/0287034 A1 | 11/2011 | Frank et al. | |
| 2012/0034196 A1 | 2/2012 | Frank et al. | |

FOREIGN PATENT DOCUMENTS

| | | |
|---|---|---|
| EP | 0 174 810 A2 | 3/1986 |
| EP | 0 267 781 A2 | 5/1988 |
| WO | WO 01/98361 A2 | 12/2001 |
| WO | WO 02/40541 | 5/2002 |
| WO | WO 2005/046762 A1 | 5/2005 |
| WO | WO 2005/068503 A2 | 7/2005 |

OTHER PUBLICATIONS

Bork et al., Go hunting in sequence databases but watch out for the traps. Trends Genet. Oct. 1996;12(10):425-7.
Bork, Powers and pitfalls in sequence analysis: the 70% hurdle. Genome Res. Apr. 2000;10(4):398-400.
Bowie et al., Deciphering the message in protein sequences: tolerance to amino acid substitutions. Science. Mar. 16, 1990;247(4948):1306-10.
Brenner, Errors in genome annotation. Trends Genet. Apr. 1999;15(4):132-3.
Brown et al., Tolerance of single, but not multiple, amino acid replacements in antibody VH CDR 2: a means of minimizing B cell wastage from somatic hypermutation? J Immunol. May 1, 1996;156(9):3285-91.
Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
Casset et al., A peptide mimetic of an anti-CD4 monoclonal antibody by rational design. Biochem Biophys Res Commun. Jul. 18, 2003;307(1):198-205.
Chung et al., Plastic microchip flow cytometer based on 2- and 3-dimensional hydrodynamic flow focusing. Microsystem Technologies. 2003;9:525-33.
De Pascalis et al., Grafting of "abbreviated" complementarity-determining regions containing specificity-determining residues essential for ligand contact to engineer a less immunogenic humanized monoclonal antibody. J Immunol. Sep. 15, 2002;169(6):3076-84.

(Continued)

*Primary Examiner* — Sheela J Huff

(74) *Attorney, Agent, or Firm* — Wolf, Greenfield & Sacks, P.C.

(57) ABSTRACT

The invention related to methods for treating a subject by manipulating ABCB5 on a cell as well as related products. The methods include methods of treating cancer using ABCB5 binding molecules such as antibodies and fragments thereof.

12 Claims, 17 Drawing Sheets

(56) References Cited

OTHER PUBLICATIONS

Dermer, Another Anniversary for the War on Cancer. Bio/Technology. Mar. 12, 1994 http://www.virusmyth.com/aids/hiv/gdbiotech.htm. Last accessed on Oct. 28, 2008. 2 pages.

Doerks et al., Protein annotation: detective work for function prediction. Trends Genet. Jun. 1998;14(6):248-50.

Frank et al., ABCB5 P-glycoprotein is a molecular marker of the Hoechst 33342 side population phenotype among human fetal skeletal muscle cells. FASEB Journal. 2004;18(4-5):A183. Abstract 144.9.

Frank et al., ABCB5-mediated doxorubicin transport and chemoresistance in human malignant melanoma. Cancer Res. May 15, 2005;65(10):4320-33.

Frank et al., Immunomodulatory functions of mesenchymal stem cells. Lancet. May 1, 2004;363(9419):1411-2.

Frank et al., Regulation of progenitor cell fusion by ABCB5 P-glycoprotein, a novel human ATP-binding cassette transporter. J Biol Chem. Nov. 21, 2003;278(47):47156-65. Epub Sep. 7, 2003.

Frank et al., Specific MDR1 P-glycoprotein blockade inhibits human alloimmune T cell activation in vitro. J Immunol. Feb. 15, 2001;166(4):2451-9.

Freshney, Culture of Animal Cells, A Manual of Basic Technique. Alan R. Liss, Inc., 1983, New York, p. 3-4.

Georges et al., Detection of P-glycoprotein isoforms by gene-specific monoclonal antibodies. Proc Natl Acad Sci U S A. Jan. 1990;87(1):152-6.

Gillet et al., Chemotherapy-induced resistance by ATP-binding cassette transporter genes. Biochim Biophys Acta. Jun. 2007;1775(2):237-62. Epub Jun. 6, 2007.

Guerci et al., Predictive value for treatment outcome in acute myeloid leukemia of cellular daunorubicin accumulation and P-glycoprotein expression simultaneously determined by flow cytometry. Blood. Apr. 15, 1995;85(8):2147-53.

Jakobovits et al., Analysis of homozygous mutant chimeric mice: deletion of the immunoglobulin heavy-chain joining region blocks B-cell development and antibody production. Proc Natl Acad Sci U S A. Mar. 15, 1993;90(6):2551-5.

Jorgensen et al., Engineering mesenchymal stem cells for immunotherapy. Gene Ther. May 2003;10(10):928-31.

Knutsen et al., Cytogenetic and molecular characterization of random chromosomal rearrangements activating the drug resistance gene, MDR1/P-glycoprotein, in drug-selected cell lines and patients with drug refractory ALL. Genes Chromosomes Cancer. Sep. 1998;23(1):44-54.

Kunkel, Rapid and efficient site-specific mutagenesis without phenotypic selection. Proc Natl Acad Sci U S A. Jan. 1985;82(2):488-92.

Lazar et al., Transforming growth factor alpha: mutation of aspartic acid 47 and leucine 48 results in different biological activities. Mol Cell Biol. Mar. 1988;8(3):1247-52.

Mechetner et al., Efficient inhibition of P-glycoprotein-mediated multidrug resistance with a monoclonal antibody. Proc Natl Acad Sci U S A. Jul. 1, 1992;89(13):5824-8.

Menke et al., Expression analysis of multidrug efflux pump genes in mouse hematopoietic stem and progenitor cells. Blood. 1999;94(10)(Supp 1, Part 1):Abstract #132.

Mickley et al., Gene rearrangement: a novel mechanism for MDR-1 gene activation. J Clin Invest. Apr. 15, 1997;99(8):1947-57.

Paul, Fundamental Immunology, 3rd Edition, 1993, pp. 292-295.

Pendse et al., P-glycoprotein functions as a differentiation switch in antigen presenting cell maturation. Am J Transplant. Dec. 2006;6(12):2884-93.

Robert, Multidrug resistance in oncology: diagnostic and therapeutic approaches. Eur J Clin Invest. Jun. 1999;29(6):536-45.

Rudikoff et al., Single amino acid substitution altering antigen-binding specificity. Proc Natl Acad Sci U S A. Mar. 1982;79(6):1979-83.

Schatton et al., Identification of cells initiating human melanomas. Nature. Jan. 17, 2008; 451(7176):345-9.

Schatton et al., The Chemoresistance Mediator ABCB5 Identifies Melanoma Stem Cells. 14th SPORE Investigator's Workshop. 2006:92. Abstract 150.

Schoenlein et al., Double minute chromosomes carrying the human multidrug resistance 1 and 2 genes are generated from the dimerization of submicroscopic circular DNAs in colchicine-selected KB carcinoma cells. Mol Biol Cell. May 1992;3(5):507-20.

Scott et al., The Pendred syndrome gene encodes a chloride-iodide transport protein. Nat Genet. Apr. 1999;21(4):440-3.

Sequence Comparison cited in parent U.S. Appl. No. 09/873,409 (Apr. 2, 2003 Office Action).

Sequence Comparison cited in parent U.S. Appl. No. 09/873,409 (Dec. 31, 2003 Office Action).

Shi et al., Transplantation of dermal multipotent cells promotes the hematopoietic recovery in sublethally irradiated rats. J Radiat Res (Tokyo). Mar. 2004;45(1):19-24.

Skolnick et al., From genes to protein structure and function: novel applications of computational approaches in the genomic era. Trends Biotechnol. Jan. 2000;18(1):34-9.

Smith et al., The challenges of genome sequence annotation or "the devil is in the details". Nat Biotechnol. Nov. 1997;15(12):1222-3.

Spangrude et al., Two mechanisms of discrimination between stem cells and progenitors by rhodamine-123: Mitochondrial activation and multi-drug resistance. Blood. 1995;86(1)(Supp 1):Abstract #1830.

Unger et al., Monolithic microfabricated valves and pumps by multilayer soft lithography. Science. Apr. 7, 2000;288(5463):113-6.

Vajdos et al., Comprehensive functional maps of the antigen-binding site of an anti-ErbB2 antibody obtained with shotgun scanning mutagenesis. J Mol Biol. Jul. 5, 2002;320(2):415-28.

Whitesides et al., Flexible Method for Microfluidics. Devices for handling nanoliter quantities of fluids are creating new fabrication challenges and finding new applications in biology, chemistry and materials science. Physics Today Online. Jun. 2001:1-8.

Young et al., Adult-derived stem cells and their potential for use in tissue repair and molecular medicine. J Cell Mol Med. Jul.-Sep. 2005;9(3):753-69.

Young et al., Human pluripotent and progenitor cells display cell surface cluster differentiation markers CD10, CD13, CD56, and MHC class-I. Proc Soc Exp Biol Med. May 1999;221(1):63-71.

Chaudhary et al., Expression and activity of P-glycoprotein, a multidrug efflux pump, in human hematopoietic stem cells. Cell. Jul. 12, 1991;66(1):85-94.

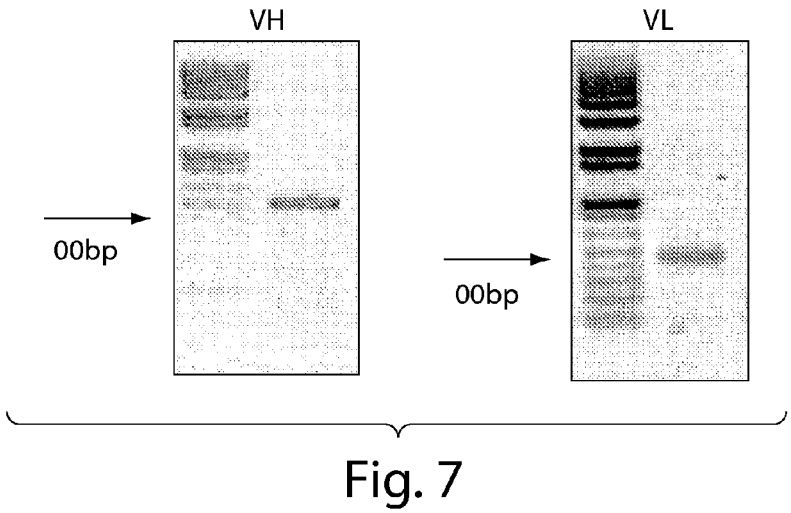

Fig. 7

HC-F1                                CDR-H1
EVQLVESGGDLVKPGGSLKLSCAASGFTFS DYYMY

HC-F2            CDR-H2        HC-F3
WVRQTPEKRLEWVA TINDGGTHTY YPDSLKGRFTISRDNAKNILYLQMSSL

CDR-H3           HC-F4
MSEDTAMYYCAR DDYYYGSHFDAMDY WGQGTSVTVSS

THE FOUR FRAMEWORK REGIONS F1, F2, F3, AND F4 AS WELL
AS THE THREE COMPLEMENTARITY DETERMINING REGIONS,
CDR-H1, CDR-H2 AND CDR-H3, ARE INDICATED.

Fig. 8

GAAGTGCAACTGGTGGAGTCTGGGGGACTTAGTGAAGCCTGGAGGGTCCTG
AAGCTCTCCTGTGCAGCCTCTGGATTCACTTTCAGTGACTATTACATGTATTGGGTTCG
TCAGACTCCGGAAAAGAGGCTGGAGTGGGTCGCCACCATTAATGATGGCGGTACTCACA
CCTACTATCCAGACAGTCTGAAGGGGCGATTCACCATCTCCAGAGACAATGCCAAGAAC
ATCCTGTACCTGCAAATGAGCAGTCTGATGTCTGAGGACACAGCCATGTATTATTGTGC
AAGAGATGATTATTACTACGGTAGTCACTTCGATGCTATGGACTACTGGGGTCAAGGAA
CCTCAGTCACCGTCTCCTCA

THE CDR SEQUENCES ARE UNDERLINED

Fig. 9

| LC-F1 | CDR-L1 | LC-F2 |
|---|---|---|
| DIVLTQSPASLAVSLGQRATISY | RASKSVSTSGYSYMH | WNQQKPGQPPRLLIY |

| CDR-L2 | LC-F3 | CDR-L3 |
|---|---|---|
| LVSNLES | EVPARFSGSGSGDTFTLNIHPVEEEDAATYYC | QHIRELTR |

LC-F4
SEGGTKLEIKR

THE FOUR FRAMEWORK REGIONS F1, F2, F3, AND F4 AS WELL AS THE THREE COMPLEMENTARITY DETERMINING REGIONS, CDR-L1, CDR-L2 AND CDR-L3, ARE INDICATED.

Fig. 10

```
        GACATTGTGCTGACACAGTCTCCTGCTTCCTTAGCTGTATCTCTGGGGCAGAGG
GCCACCATCTCATACAGGGCCAGCAAAAGTGTCAGTACATCTGGCTATAGTTATATGCA
CTGGAACCAACAGAAACCAGGACAGCCACCCAGACTCCTCATCTATCTTGTATCCAACC
TAGAATCTGAGGTCCCTGCCAGGTTCAGTGGCAGTGGGTCTGGGACAGACTTCACCCTC
AACATCCATCCTGTGGAGGAGGAGGATGCTGCAACCTATTACTGTCAGCACATTAGGGA
GCTTACACGTTCGGAGGGGGGCACCAAGCTGGAAATCAAACGG
```

THE CDR SEQUENCES ARE UNDERLINED.

Fig. 11

```
ATGGACTTTGGGCTGAGCTTGGTTTTCCTTGTCCTTGTTTTAAAAGGTGTCCAG
TGTGAAGTGCAACTGGTGGAGTCTGGGGGAGACTTAGTGAAGCCTGGAGGGTCCCTGAA
GCTCTCCTGTGCAGCCTCTGGATTCACTTTCAGTGACTATTACATGTATTGGGTTCGTC
AGACTCCGGAAAAGAGGCTGGAGTGGGTCGCCACCATTAATGATGGCGGTACTCACACC
TACTATCCAGACAGTCTGAAGGGGCGATTCACCATCTCCAGAGACAATGCCAAGAACAT
CCTGTACCTGCAAATGAGCAGTCTGATGTCTGAGGACACAGCCATGTATTATTGTGCAA
GAGATGATTATTACTACGGTAGTCACTTCGATGCTATGGACTACTGGGGTCAAGGAACC
TCAGTCACCGTCTCCTCAGCCTCCACCAAGGGCCCATCGGTCTTCCCCCTGGCACCCTC
CTCCAAGAGCACCTCTGGGGGCACAGCGGCCCTGGGCTGCCTGGTCAAGGACTACTTCC
CCGAACCGGTGACGGTGTCGTGGAACTCAGGCGCCCTGACCAGCGGCGTGCACACCTTC
CCGGCTGTCCTACAGTCCTCAGGACTCTACTCCCTCAGCAGCGTGGTGACCGTGCCCTC
CAGCAGCTTGGGCACCCAGACCTACATCTGCAACGTGAATCACAAGCCCAGCAACACCA
AGGTGGACAAGAAAGTTGAGCCCAAATCTTGTGACAAAACTCACACATGCCCACCGTGC
CCAGCACCTGAACTCCTGGGGGGACCGTCAGTCTTCCTCTTCCCCCCAAAACCCAAGGA
CACCCTCATGATCTCCCGGACCCCTGAGGTCACATGCGTGGTGGTGGACGTGAGCCACG
AAGACCCTGAGGTCAAGTTCAACTGGTACGTGGACGGCGTGGAGGTGCATAATGCCAAG
ACAAAGCCGCGGGAGGAGCAGTACAACAGCACGTACCGGGTGGTCAGCGTCCTCACCGT
CCTGCACCAGGACTGGCTGAATGGCAAGGAGTACAAGTGCAAGGTCTCCAACAAAGCCC
TCCCAGCCCCCATCGAGAAAACCATCTCCAAAGCCAAAGGGCAGCCCCGAGAACCACAG
GTGTACACCCTGCCCCCATCCCGGGATGAGCTGACCAAGAACCAGGTCAGCCTGACCTG
CCTGGTCAAAGGCTTCTATCCCAGCGACATCGCCGTGGAGTGGGAGAGCAATGGGCAGC
CGGAGAACAACTACAAGACCACGCCTCCCGTGCTGGACTCCGACGGCTCCTTCTTCCTC
TACAGCAAGCTCACCGTGGACAAGAGCAGGTGGCAGCAGGGGAACGTCTTCTCATGCTC
CGTGATGCATGAGGCTCTGCACAACCACTACACGCAGAAGAGCCTCTCCCTGTCTCCGG
GTAAATGA
```

Fig. 12

ATGGAGACAGACACACTCCTGCTATGGGTACTGCTGCTCTGGGTTCCAGGTTCC
ACTGGTGACATTGTGCTGACACAGTCTCCTGCTTCCTTAGCTGTATCTCTGGGGCAGAG
GGCCACCATCTCATACAGGGCCAGCAAAAGTGTCAGTACATCTGGCTATAGTTATATGC
ACTGGAACCAACAGAAACCAGGACAGCCACCCAGACTCCTCATCTATCTTGTATCCAAC
CTAGAATCTGAGGTCCCTGCCAGGTTCAGTGGCAGTGGGTCTGGGACAGACTTCACCCT
CAACATCCATCCTGTGGAGGAGGAGGATGCTGCAACCTATTACTGTCAGCACATTAGGG
AGCTTACACGTTCGGAGGGGGGCACCAAGCTGGAAATCAAACGGACTGTGGCTGCACCA
TCTGTCTTCATCTTCCCGCCATCTGATGAGCAGTTGAAATCTGGAACTGCCTCTGTTGT
GTGCCTGCTGAATAACTTCTATCCCAGAGAGGCCAAAGTACAGTGGAAGGTGGATAACG
CCCTCCAATCGGGTAACTCCCAGGAGAGTGTCACAGAGCAGGACAGCAAGGACAGCACC
TACAGCCTCAGCAGCACCCTGACGCTGAGCAAAGCAGACTACGAGAAACACAAAGTCTA
CGCCTGCGAAGTCACCCATCAGGGCCTGAGCTCGCCCGTCACAAAGAGCTTCAACAGGG
GAGAGTGTTGA

Fig. 13

SEQUENCE LISTING

```
<160> NUMBER OF SEQ ID NOS: 20

<210> SEQ ID NO 1
<211> LENGTH: 123
<212> TYPE: PRT
<213> ORGANISM: artificial sequence
<220> FEATURE:
<223> OTHER INFORMATION: Synthetic peptide

<400> SEQUENCE: 1

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asp Tyr
            20                  25                  30
```

Tyr Met Tyr Trp Val Arg Gln Thr Pro Glu Lys Arg Leu Glu Trp Val
            35                  40                  45

Ala Thr Ile Asn Asp Gly Gly Thr His Thr Tyr Tyr Pro Asp Ser Leu
 50                  55                  60

Lys Gly Arg Phe Thr Ile Ser Arg Asp Asn Ala Lys Asn Ile Leu Tyr
65                  70                  75                  80

Leu Gln Met Ser Ser Leu Met Ser Glu Asp Thr Ala Met Tyr Tyr Cys
                85                  90                  95

Ala Arg Asp Asp Tyr Tyr Tyr Gly Ser His Phe Asp Ala Met Asp Tyr
                100                 105                 110

Trp Gly Gln Gly Thr Ser Val Thr Val Ser Ser
            115                 120

<210> SEQ ID NO 2
<211> LENGTH: 111
<212> TYPE: PRT
<213> ORGANISM: artificial sequence
<220> FEATURE:
<223> OTHER INFORMATION: Synthetic peptide

<400> SEQUENCE: 2

Asp Ile Val Leu Thr Gln Ser Pro Ala Ser Leu Ala Val Ser Leu Gly
 1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Glu Val Pro Ala
 50                  55                  60

Arg Phe Ser Gly Ser Gly Ser Gly Asp Thr Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Thr Lys Leu Glu Ile Lys Arg
            100                 105                 110

<210> SEQ ID NO 3
<211> LENGTH: 5
<212> TYPE: PRT
<213> ORGANISM: artificial sequence
<220> FEATURE:
<223> OTHER INFORMATION: Synthetic peptide

<400> SEQUENCE: 3

Asp Tyr Tyr Met Tyr
 1               5

<210> SEQ ID NO 4
<211> LENGTH: 10
<212> TYPE: PRT
<213> ORGANISM: artificial sequence
<220> FEATURE:
<223> OTHER INFORMATION: Synthetic peptide

<400> SEQUENCE: 4

Thr Ile Asn Asp Gly Gly Thr His Thr Tyr
 1               5                   10

<210> SEQ ID NO 5
<211> LENGTH: 14
<212> TYPE: PRT

-continued

<213> ORGANISM: artificial sequence
<220> FEATURE:
<223> OTHER INFORMATION: Synthetic peptide

<400> SEQUENCE: 5

Asp Asp Tyr Tyr Tyr Gly Ser His Phe Asp Ala Met Asp Tyr
1               5                   10

<210> SEQ ID NO 6
<211> LENGTH: 15
<212> TYPE: PRT
<213> ORGANISM: artificial sequence
<220> FEATURE:
<223> OTHER INFORMATION: Synthetic peptide

<400> SEQUENCE: 6

Arg Ala Ser Lys Ser Val Ser Thr Ser Gly Tyr Ser Tyr Met His
1               5                   10                  15

<210> SEQ ID NO 7
<211> LENGTH: 7
<212> TYPE: PRT
<213> ORGANISM: artificial sequence
<220> FEATURE:
<223> OTHER INFORMATION: Synthetic peptide

<400> SEQUENCE: 7

Leu Val Ser Asn Leu Glu Ser
1               5

<210> SEQ ID NO 8
<211> LENGTH: 8
<212> TYPE: PRT
<213> ORGANISM: artificial sequence
<220> FEATURE:
<223> OTHER INFORMATION: Synthetic peptide

<400> SEQUENCE: 8

Gln His Ile Arg Glu Leu Thr Arg
1               5

<210> SEQ ID NO 9
<211> LENGTH: 369
<212> TYPE: DNA
<213> ORGANISM: artificial sequence
<220> FEATURE:
<223> OTHER INFORMATION: Synthetic oligonucleotide

<400> SEQUENCE: 9
gaagtgcaac tggtggagtc tgggggagac ttagtgaagc ctggagggtc cctgaagctc      60
tcctgtgcag cctctggatt cactttcagt gactattaca tgtattgggt tcgtcagact     120
ccggaaaaga ggctggagtg ggtcgccacc attaatgatg gcggtactca cacctactat     180
ccagacagtc tgaaggggcg attcaccatc tccagagaca tgccaagaa catcctgtac      240 ctgcaaatga gcagtctgat gtctgaggac acagccatgt attattgtgc aagagatgat     300
tattactacg gtagtcactt cgatgctatg gactactggg gtcaaggaac ctcagtcacc     360
gtctcctca                                                            369

<210> SEQ ID NO 10
<211> LENGTH: 333
<212> TYPE: DNA
<213> ORGANISM: artificial sequence
<220> FEATURE:
<223> OTHER INFORMATION: Synthetic oligonucleotide -continued

```
<400> SEQUENCE: 10
gacattgtgc tgacacagtc tcctgcttcc ttagctgtat ctctggggca gagggccacc      60
atctcataca gggccagcaa aagtgtcagt acatctggct atagttatat gcactggaac     120
caacagaaac caggacagcc acccagactc ctcatctatc ttgtatccaa cctagaatct     180
gaggtccctg ccaggttcag tggcagtggg tctgggacag acttcaccct caacatccat     240
cctgtggagg aggaggatgc tgcaacctat tactgtcagc acattaggga gcttacacgt     300
tcggaggggg gcaccaagct ggaaatcaaa cgg                                  333

<210> SEQ ID NO 11
<211> LENGTH: 15
<212> TYPE: DNA
<213> ORGANISM: artificial sequence
<220> FEATURE:
<223> OTHER INFORMATION: Synthetic oligonucleotide

<400> SEQUENCE: 11
gactattaca tgtat                                                       15

<210> SEQ ID NO 12
<211> LENGTH: 30
<212> TYPE: DNA
<213> ORGANISM: artificial sequence
<220> FEATURE:
<223> OTHER INFORMATION: Synthetic oligonucleotide

<400> SEQUENCE: 12
accattaatg atggcggtac tcacacctac                                       30

<210> SEQ ID NO 13
<211> LENGTH: 42
<212> TYPE: PRT
<213> ORGANISM: artificial sequence
<220> FEATURE:
<223> OTHER INFORMATION: Synthetic oligonucleotide

<400> SEQUENCE: 13

Gly Ala Thr Gly Ala Thr Thr Ala Thr Thr Ala Cys Thr Ala Cys Gly
1               5                   10                  15

Gly Thr Ala Gly Thr Cys Ala Cys Thr Thr Cys Gly Ala Thr Gly Cys
            20                  25                  30

Thr Ala Thr Gly Gly Ala Cys Thr Ala Cys
        35                  40

<210> SEQ ID NO 14
<211> LENGTH: 45
<212> TYPE: DNA
<213> ORGANISM: artificial sequence
<220> FEATURE:
<223> OTHER INFORMATION: Synthetic oligonucleotide

<400> SEQUENCE: 14
agggccagca aaagtgtcag tacatctggc tatagttata tgcac                      45

<210> SEQ ID NO 15
<211> LENGTH: 21
<212> TYPE: DNA
<213> ORGANISM: artificial sequence
<220> FEATURE:
<223> OTHER INFORMATION: Synthetic oligonucleotide

<400> SEQUENCE: 15
cttgtatcca acctagaatc t                                                21
```

<210> SEQ ID NO 16
<211> LENGTH: 24
<212> TYPE: DNA
<213> ORGANISM: artificial sequence
<220> FEATURE:
<223> OTHER INFORMATION: Synthetic oligonucleotide

<400> SEQUENCE: 16
cagcacatta gggagcttac acgt                                          24

<210> SEQ ID NO 17
<211> LENGTH: 1419
<212> TYPE: DNA
<213> ORGANISM: artificial sequence
<220> FEATURE:
<223> OTHER INFORMATION: Synthetic oligonucleotide

<400> SEQUENCE: 17
atggactttg ggctgagctt ggttttcctt gtccttgttt taaaaggtgt ccagtgtgaa      60
gtgcaactgg tggagtctgg gggagactta gtgaagcctg agggtccct gaagctctcc     120 tgtgcagcct ctggattcac tttcagtgac tattacatgt attgggttcg tcagactccg     180
gaaaagaggc tggagtgggt cgccaccatt aatgatggcg gtactcacac ctactatcca     240
gacagtctga gggggcgatt caccatctcc agagacaatg ccaagaacat cctgtacctg     300
caaatgagca gtctgatgtc tgaggacaca gccatgtatt attgtgcaag agatgattat     360
tactacggta gtcacttcga tgctatggac tactggggtc aaggaacctc agtcaccgtc     420
tcctcagcct ccaccaaggg cccatcggtc ttccccctgg cacctcctc caagagcacc     480 tctgggggca gcggccct gggctgcctg gtcaaggact acttccccga accggtgacg     540
gtgtcgtgga actcaggcgc cctgaccagc ggcgtgcaca ccttcccggc tgtcctacag     600
tcctcaggac tctactccct cagcagcgtg gtgaccgtgc cctccagcag cttgggcacc     660
cagacctaca tctgcaacgt gaatcacaag cccagcaaca ccaaggtgga caagaaagtt     720
gagcccaaat cttgtgacaa aactcacaca tgcccaccgt gcccagcacc tgaactcctg     780
gggggaccgt cagtcttcct cttccccca aaacccaagg acaccctcat gatctcccgg     840
acccctgagg tcacatgcgt ggtggtggac gtgagccacg aagaccctga ggtcaagttc     900
aactggtacg tggacggcgt ggaggtgcat aatgccaaga caaagccgcg ggaggagcag     960
tacaacagca cgtaccgggt ggtcagcgtc ctcaccgtcc tgcaccagga ctggctgaat    1020
ggcaaggagt acaagtgcaa ggtctccaac aaagccctcc cagccccat cgagaaaacc    1080 atctccaaag ccaaagggca gccccgagaa ccacaggtgt acaccctgcc cccatcccgg    1140
gatgagctga ccaagaacca ggtcagcctg acctgcctgg tcaaaggctt ctatcccagc    1200
gacatcgccg tggagtggga gagcaatggg cagccggaga acaactacaa gaccacgcct    1260
cccgtgctgg actccgacgg ctccttcttc ctctacagca agctcaccgt ggacaagagc    1320
aggtggcagc aggggaacgt cttctcatgc tccgtgatgc atgaggctct gcacaaccac    1380
tacacgcaga agagcctctc cctgtctccg ggtaaatga                          1419

<210> SEQ ID NO 18
<211> LENGTH: 714
<212> TYPE: DNA
<213> ORGANISM: artificial sequence
<220> FEATURE:
<223> OTHER INFORMATION: Synthetic oligonucleotide

<400> SEQUENCE: 18

```
atggagacag acacactcct gctatgggta ctgctgctct gggttccagg ttccactggt    60
gacattgtgc tgacacagtc tcctgcttcc ttagctgtat ctctgggca gagggccacc   120 atctcataca gggccagcaa aagtgtcagt acatctggct atagttatat gcactggaac   180
caacagaaac caggacagcc acccagactc ctcatctatc ttgtatccaa cctagaatct   240
gaggtccctg ccaggttcag tggcagtggg tctgggacag acttcaccct caacatccat   300
cctgtggagg aggaggatgc tgcaacctat tactgtcagc acattaggga gcttacacgt   360
tcggaggggg gcaccaagct ggaaatcaaa cggactgtgg ctgcaccatc tgtcttcatc   420
ttcccgccat ctgatgagca gttgaaatct ggaactgcct ctgttgtgtg cctgctgaat   480
aacttctatc ccagagaggc caaagtacag tggaaggtgg ataacgccct ccaatcgggt   540
aactcccagg agagtgtcac agagcaggac agcaaggaca gcacctacag cctcagcagc   600
accctgacgc tgagcaaagc agactacgag aaacacaaag tctacgcctg cgaagtcacc   660
catcagggcc tgagctcgcc cgtcacaaag agcttcaaca ggggagagtg ttga          714

<210> SEQ ID NO 19
<211> LENGTH: 1362
<212> TYPE: DNA
<213> ORGANISM: artificial sequence
<220> FEATURE:
<223> OTHER INFORMATION: Synthetic oligonucleotide

<400> SEQUENCE: 19
gaagtgcaac tggtggagtc tgggggagac ttagtgaagc tggagggtc cctgaagctc     60 tcctgtgcag cctctggatt cactttcagt gactattaca tgtattgggt tcgtcagact   120
ccggaaaaga ggctggagtg gtcgccacc attaatgatg gcggtactca cacctactat   180
ccagacagtc tgaaggggcg attcaccatc tccagagaca atgccaagaa catcctgtac   240
ctgcaaatga gcagtctgat gtctgaggac acagccatgt attattgtgc aagagatgat   300
tattactacg gtagtcactt cgatgctatg gactactggg gtcaaggaac ctcagtcacc   360
gtctcctcag cctccaccaa gggcccatcg gtcttccccc tggcaccctc ctccaagagc   420
acctctgggg gcacagcggc cctgggctgc ctggtcaagg actacttccc cgaaccggtg   480
acggtgtcgt ggaactcagg cgccctgacc agcggcgtgc acaccttccc ggctgtccta   540
cagtcctcag gactctactc cctcagcagc gtggtgaccg tgccctccag cagcttgggc   600
acccagacct acatctgcaa cgtgaatcac aagcccagca acaccaaggt ggacaagaaa   660
gttgagccca atcttgtga caaaactcac acatgcccac cgtgcccagc acctgaactc   720
ctggggggac cgtcagtctt cctcttcccc ccaaaaccca aggacaccct catgatctcc   780
cggacccctg aggtcacatg cgtggtggtg gacgtgagcc acgaagaccc tgaggtcaag   840
ttcaactggt acgtggacgg cgtggaggtg cataatgcca agacaaagcc gcggaggag   900 cagtacaaca gcacgtaccg ggtggtcagc gtcctcaccg tcctgcacca ggactggctg   960
aatggcaagg agtacaagtg caaggtctcc aacaaagccc tcccagcccc catcgagaaa  1020
accatctcca aagccaaagg gcagcccga gaaccacagg tgtacaccct gcccccatcc  1080
cgggatgagc tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcaggtggc agcaggggaa cgtcttctca tgctccgtga tgcatgaggc tctgcacaac  1320
cactacacgc agaagagcct ctccctgtct ccgggtaaat ga                      1362
```

```
<210> SEQ ID NO 20
<211> LENGTH: 654
<212> TYPE: DNA
<213> ORGANISM: artificial sequence
<220> FEATURE:
<223> OTHER INFORMATION: Synthetic oligonucleotide

<400> SEQUENCE: 20
gacattgtgc tgacacagtc tcctgcttcc ttagctgtat ctctgggca gagggccacc      60 atctcataca gggccagcaa aagtgtcagt acatctggct atagttatat gcactggaac    120
caacagaaac caggacagcc acccagactc ctcatctatc ttgtatccaa cctagaatct    180
gaggtccctg ccaggttcag tggcagtggg tctgggacag acttcaccct caacatccat    240
cctgtggagg aggaggatgc tgcaacctat tactgtcagc acattaggga gcttacacgt    300 tcggagggggg gcaccaagct ggaaatcaaa cggactgtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg ttga           654
```

TARGETING ABCB5 FOR CANCER THERAPY

RELATED APPLICATIONS

This Application claims the benefit under 35 U.S.C. §120 of U.S. application Ser. No. 12/101,428, entitled "TARGETING ABCB5 FOR CANCER THERAPY" filed on Apr. 11, 2008, which is herein incorporated by reference in its entirety. Application Ser. No. 12/101,428 claims priority under 35 U.S.C. §119(e) to U.S. Provisional Application Ser. No. 60/923,128, entitled "TARGETING ABCB5 FOR CANCER THERAPY" filed on Apr. 12, 2007, which is herein incorporated by reference in its entirety. Application Ser. No. 12/101,428 claims priority under 35 U.S.C. §119(e) to U.S. Provisional Application Ser. No. 61/007,059, entitled "TARGETING ABCB5 FOR CANCER THERAPY" filed on Dec. 11, 2007, which is herein incorporated by reference in its entirety.

FEDERALLY SPONSORED RESEARCH

This invention was made with Government support under NIH Grant No. 1R01CA113796-01A1. The Government has certain rights in this invention.

BACKGROUND OF INVENTION

Human malignant melanoma is a highly chemorefractory cancer. There are currently not many effective treatment options. Malignant melanoma of the skin is highly prevalent in the United States, with 1 in 63 men and women afflicted during their lifetime. Of those, 11% are diagnosed after the cancer has spread to regional lymph nodes or directly beyond the primary site and 3% after the cancer has already metastasized (distant stage), with corresponding 5-year relative survival rates of 63.8% and 16.0%.

SUMMARY OF INVENTION

The invention is based at least in part on the discovery that chemoresistant ABCB5+ tumor stem cells contribute to the development of cancers such as melanoma and that these cells can be targeted to treat the cancer. ABCB5 targeting may be employed as either a stand-alone therapeutic approach to disseminated disease, or as an adjunctive therapy to sensitize cancer cells to chemotherapeutic agents, especially in those patients with currently refractory metastatic disease. An advantage of ABCB5-targeted therapeutic approaches is that they are directed at tumorigenic stem cells, whereas conventional therapeutics target only the bulk population of tumor cells.

In some aspects the invention relates to a method of delivering a therapeutic agent to an intracellular compartment of a cell by contacting a cell with an isolated molecule that selectively binds to ABCB5 conjugated to a therapeutic agent in an effective amount to deliver the therapeutic agent to an intracellular compartment of the cell.

In some embodiments the isolated molecule that selectively binds to ABCB5 is an isolated peptide. In other embodiments it is a small molecule. The isolated peptide may be, for instance, an antibody or antigen binding fragment thereof or an scFv.

The therapeutic agent may be, in some embodiments, a toxin, an siRNA, a chemotherapeutic agent or a therapeutic antibody.

The method involves, in other embodiments the step of contacting a cell with an isolated molecule that selectively binds to a surface marker such as CD49e, CD133, CD166, BMPR1a, TIR-1, VE-cadherin (CD144) or nestin.

According to another aspect of the invention a composition is provided of an isolated peptide that selectively binds to ABCB5 and comprises an amino acid sequence selected from the group consisting of SEQ ID NO: 1, SEQ ID NO:2, SEQ ID NO:3, SEQ ID NO:4, SEQ ID NO:5, SEQ ID NO:6, SEQ ID NO:7 and SEQ ID NO:8, or functionally equivalent variants thereof containing conservative substitutions, wherein the isolated peptide is not mAb 3C2-1D12.

In other aspects of the invention a composition of an isolated peptide that selectively binds to ABCB5 and comprises an amino acid sequence selected from the group consisting of SEQ ID NO: 1, SEQ ID NO:2, SEQ ID NO:3, SEQ ID NO:4, SEQ ID NO:5, SEQ ID NO:6, SEQ ID NO:7, and SEQ ID NO:8, or functionally equivalent variants thereof containing conservative substitutions is provided. The isolated antibody or antibody fragment is present in an effective amount for enhancing chemosensitization in a human subject.

According to yet another aspect of the invention a composition of an isolated peptide that selectively binds to ABCB5 and comprises an amino acid sequence selected from the group consisting of SEQ ID NO: 1, SEQ ID NO:2, SEQ ID NO:3, SEQ ID NO:4, SEQ ID NO:5, SEQ ID NO:6, SEQ ID NO:7 and SEQ ID NO:8, or functionally equivalent variants thereof containing conservative substitutions is provided. The isolated peptide is preferably co-formulated with a therapeutic agent.

The isolated peptide, in some embodiments, is conjugated to the therapeutic agent. In other embodiments the therapeutic agent is selected from the group consisting of camptothecin 9-NH2, mitoxantrone, camptothecin 7-Cl, pyrazofurin, menogaril, camptothecin 20 ester, camptothecin, amsacrine, etoposide, anthrapyrazole-derivitive, terniposide, camptothecin 11-formyl, camptothecin 10-OH, daunorubicin, doxydoxorubicin, doxorubicin, oxanthrazoole, camptothecin 11-HOMe, zorubicin, uracil mustard, piperazinedione, hepsulfam, melphalan, bisantrene, triethylenemelamine, spiromustine, Yoshi-864, chlorambucil, piperazine mustard, hydroxyurea, porfiromycin, mechlorethamine, fluorodopan, mitomycin, cytarabine (araC), dianhydrogalactitol, gemcitabine, thiotepa, N,N-dibenzyl-daunomycin, teroxirone, and aphidicolin-glycinate.

A kit is provided according to other aspects of the invention. The kit includes a container housing an isolated peptide that selectively binds to ABCB5 and comprises an amino acid sequence selected from the group consisting of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12, or functionally equivalent variants thereof containing conservative substitutions, and instructions for administering the isolated peptide to a human subject.

A method for treating a subject is provided according to other aspects of the invention. The method involves systemically administering an isolated peptide that selectively binds to ABCB5 and comprises an amino acid sequence selected from the group consisting of SEQ ID NO: 1, SEQ ID NO:2, SEQ ID NO:3, SEQ ID NO:4, SEQ ID NO:5, SEQ ID NO:6, SEQ ID NO:7 and SEQ ID NO:8, or functionally equivalent variants thereof containing conservative substitutions to a subject having cancer in an effective amount to treat the cancer.

Method for treating a subject by administering any one of the compositions described herein to a subject having cancer in an effective amount to treat the cancer is also provided. A method for treating a subject is provided according to other aspects of the invention. The method involves administering an isolated peptide that selectively binds to ABCB5 and comprises an amino acid sequence selected from the group consisting of SEQ ID NO: 1, SEQ ID NO:2, SEQ ID NO:3, SEQ ID NO:4, SEQ ID NO:5, SEQ ID NO:6, SEQ ID NO:7 and SEQ ID NO:8, or functionally equivalent variants thereof containing conservative substitutions and a chemotherapeutic agent, to a subject having cancer in an effective amount to treat the cancer.

According to other aspects of the invention a method is provided for treating a subject by systemically administering to a subject having cancer in an effective amount to treat the cancer an isolated antibody or antibody fragment that selectively binds to ABCB5 and a chemotherapeutic agent.

The invention in other aspects is an isolated peptide of an immunoglobulin heavy chain variable domain, wherein: (i) CDR14-H1 comprises an amino acid sequence of SEQ ID NO. 3; (ii) CDR2-H2 comprises an amino acid sequence of SEQ ID NO. 4; and (iii) a CDR3-H3 sequence, wherein the isolated peptide is not mAb 3C2-1D12. In some embodiments the CDR3-H3 has an amino acid sequence of SEQ ID NO. 3. The isolated peptide may bind to human ABCB5 and may be an antibody. Optionally the isolated peptide further includes a light chain variable domain wherein CDR1-L1 has an amino acid sequence of SEQ ID NO. 6, a CDR2-L2 that has an amino acid sequence of SEQ ID NO. 7 and/or a CDR3-L3 that has an amino acid sequence of SEQ ID NO. 8.

In other aspects the invention is an isolated peptide having an immunoglobulin light chain variable domain, wherein: (i) CDR1-L1 has an amino acid sequence of SEQ ID NO. 6; (ii) CDR2-L2 has an amino acid sequence of SEQ ID NO. 7; and (iii) a CDR3-L3 sequence, wherein the isolated peptide is not mAb 3C2-1D12. In some embodiments the CDR3-L3 has an amino acid sequence of SEQ ID NO. 8.

An isolated peptide having at least two antibody variable domains: (a) a heavy chain antibody variable domain comprising the isolated peptide as described herein and (b) a light chain antibody variable domain comprising the isolated peptide as described herein is provided according to other aspects of the invention. In some embodiments the isolated peptide is a single chain Fv. In other embodiments the isolated peptide is a Fab isolated peptide. In yet other embodiments the isolated peptide is a fully human isolated peptide.

The isolated peptide may further include framework regions FR1, FR2, FR3, and/or FR4 for an isolated peptide variable domain corresponding to the variant CDR1-H1, CDR2-H2, CDR3-H3, wherein the framework regions are obtained from a single polypeptide template. Each of the framework regions may have an amino acid sequence corresponding to the framework region amino acid sequences of polypeptide SEQ ID NO: 1.

In some embodiments the isolated peptide further includes a dimerization domain linked to the C-terminal region of a heavy chain polypeptide variable domain. The dimerization domain may be a leucine zipper domain or a sequence having at least one cysteine residue. The dimerization domain has a hinge region in some embodiments. In other embodiments the dimerization domain is a single cysteine. In some embodiments the isolated peptide is a monoclonal antibody. In other embodiments it is a bispecific antibody. In yet other embodiments the isolated peptide is a synthetic antibody.

According to another aspect of the invention an anti-ABCB5 antibody or antigen-binding fragment thereof is provided. The antibody has a human constant region, wherein the anti-ABCB5 antibody or antigen binding fragment competitively inhibits binding of mAb 3C2-1D12 to ABCB5. In some embodiments the antigen-binding fragment is selected from the group consisting of Fab, Fab', F(ab')$_2$, Fv, scFv, dsFv, Fd, VH dAb, and VL dAb. In other embodiments the antibody or antigen-binding fragment is of immunoglobulin class IgA, IgGb 1, IgG2, IgG3, IgG4 or IgM. In yet other embodiments the antibody or antigen-binding fragment comprises a human constant region and a human variable framework region or the antigen-binding fragment is a single chain antibody. The single chain antibody optionally is a camelid antibody.

A humanized antibody variable domain having a functional antigen binding region is provided according to other aspects of the invention. The humanized antibody variable domain has non-human CDR1-H1, CDR2-H2, CDR3-H3, CDR1-L1, CDR2-L2, and CDR3-L3 having at least 90% homology to CDR1-H1, CDR2-H2, CDR3-H3, CDR1-L1, CDR2-L2, and CDR3-L3 of mAb 3C2-1D12 incorporated into a human antibody variable domain.

In other aspects of the invention a chimeric antibody is provided. The chimeric antibody has a variable domain which specifically binds to ABCB5 and a constant domain, wherein the variable domain and the constant domain are from different species.

In some embodiments the isolated peptide has an amino acid sequence of a ABCB5-binding CDR3-H3 or functionally equivalent variant thereof. In other embodiments the isolated peptide has an amino acid sequence of a ABCB5-binding CDR2-H2 or functionally equivalent variant thereof. In other embodiments the isolated peptide has an amino acid sequence of a ABCB5-binding CDR1-H1 or functionally equivalent variant thereof. In other embodiments the isolated peptide has an amino acid sequence of a ABCB5-binding CDR3-L3 or functionally equivalent variant thereof. In other embodiments the isolated peptide has an amino acid sequence of a ABCB5-binding CDR2-L2 or functionally equivalent variant thereof. In yet other embodiments the isolated peptide has an amino acid sequence of a ABCB5-binding CDR1-L1 or functionally equivalent variant thereof.

In other embodiments the isolated peptide is an isolated antibody or antibody fragment. The isolated antibody or antibody fragment may optionally be an intact soluble monoclonal antibody. In other embodiments the isolated antibody or antibody fragment is an isolated monoclonal antibody fragment selected from the group consisting of an Fab, Fab', F(ab)$_2$, Fv, scFv, dsFv, Fd, VH dAb, and VL dAb. In yet other embodiments the isolated antibody or antibody fragment enhances chemosensitization. In a preferred embodiment the isolated peptide selectively binds to ABCB5. In yet other embodiments the isolated antibody or antibody fragment is a humanized antibody. The isolated peptide optionally may be a scFv. The isolated peptide in other embodiments is conjugated to a detectable label. The composition may also include a pharmaceutically acceptable carrier and optionally is a sterile formulation.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1 is a series of images and graphs depicting a melanoma progression tissue microarray analysis for ABCB5 as well as a characterization of ABCB5+ melanoma populations. FIGS. 1(b-c) depict several characterizations of ABCB5+ melanoma populations.

FIG. 2 is a series of graphs and images depicting the in vivo tumorigenicity of ABCB5+ melanoma cell subsets in human to mouse tumor xenograft models.

FIG. 3 depicts the in vivo tracking of tumorigenicity, self-renewal and differentiation of human ABCB5+ melanoma cells in NOD/SCID mouse recipients.

FIG. 4 is a series of graphs and images representing the analysis of the ABCB5 mAb effect on melanoma xenograft growth.

FIG. 7 is a gel depicting cDNA bands that were produced from the RNA heavy chain (HC) and light chain (LC) variable regions (VRs) by reverse-transcription. Both HC and LC VR PCR products were cloned into the Invitrogen sequencing vector pCR2.1 and transformed into TOP10 cells.

FIG. 8 is 3C2-1D12 antibody HC VR amino acid sequence (SEQ ID NO:1).

FIG. 9 is 3C2-1D12 antibody HC VR nucleotide sequence (SEQ ID NO:9).

FIG. 10 is 3C2-1D12 antibody LC VR amino acid sequence (SEQ ID NO:2).

FIG. 11 is 3C2-1D12 antibody LC VR nucleotide sequence (SEQ ID NO:10).

FIG. 12 is 3C2-1D12 antibody full length heavy chain nucleotide sequence (SEQ ID NO:17).

FIG. 13 is 3C2-1D12 antibody full length light chain nucleotide sequence (SEQ ID NO:18).

DETAILED DESCRIPTION

Figure 1A:
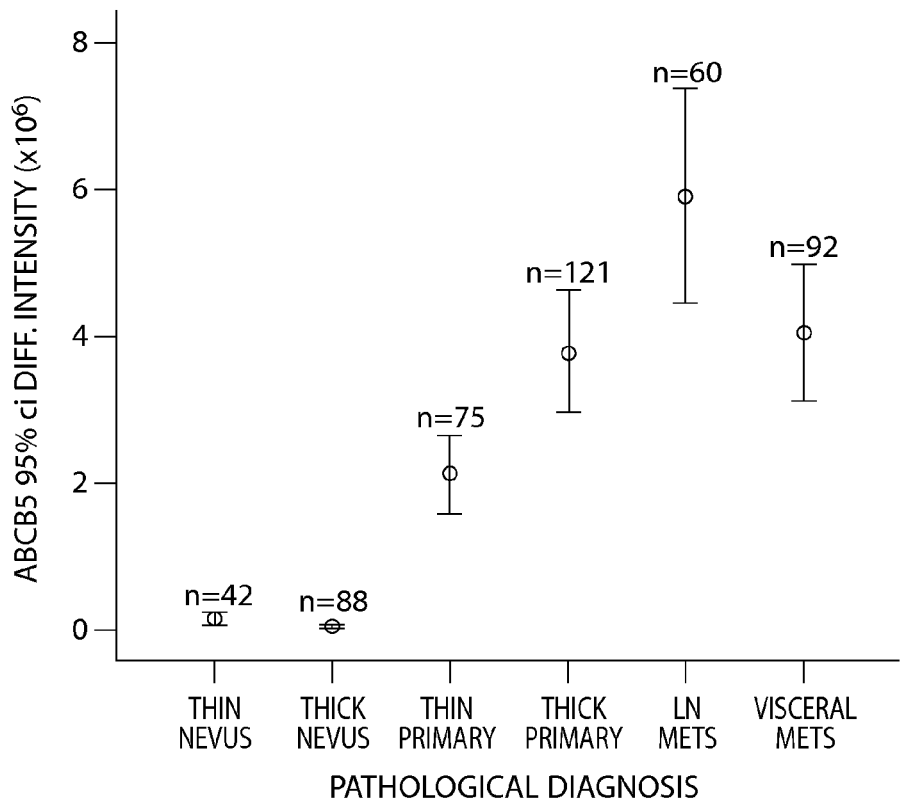
FIG. 1(a) shows a chart illustrating an analysis by the Chromavision Automated Cellular Image System, showing significant differences in ABCB5 staining intensities for thin and thick melanocytic nevi, versus thin and thick primary melanomas, versus lymph node and visceral melanoma metastases (thin or thick nevi vs. thin or thick primary melanomas, or vs. lymph node or visceral metastases, all P values<0.001; thin primary melanomas vs. thick primary melanomas P=0.004; thin and thick primary melanomas vs. lymph node metastases, P=0.001, lymph node metastases vs. visceral metastases, P=0.025).

Tumor initiating cells capable of self-renewal and differentiation, which are responsible for tumor growth, have been identified in human hematological malignancies and solid cancers. If such minority populations are associated with tumor progression in human patients, specific targeting of tumor initiating cells might provide for a novel strategy to eradicate cancers currently resistant to systemic therapy. A subpopulation enriched for human malignant cancer initiating cells defined by expression of the chemoresistance mediator ABCB5 have been identified according to the invention. As shown in the Examples below, specific targeting of this tumorigenic minority population abrogates tumor growth.

The inventors recently cloned and characterized ABCB5, a novel human multidrug resistance transporter shown to be preferentially expressed by cells of melanocytic lineage. Inhibition of ABCB5 renders normally resistant melanoma cells susceptible to doxorubicin. We have demonstrated that ABCB5 expression 1) marks tumorigenic melanoma cells of stem cell phenotype and function; and 2) specific targeting of the ABCB5+ melanoma stem cell compartment constitutes a novel, highly promising stem cell-targeted approach to melanoma therapy. The data is described in more detail in the Examples section.

Additionally, in serial human to mouse xenotransplantation experiments, ABCB5+ melanoma cells possessed greater tumorigenic capacity than ABCB5− bulk populations. Moreover, in vivo genetic cell fate tracking demonstrated tumorigenic ABCB5+ cancer cells were able to generate ABCB5+ and ABCB5− progeny, whereas ABCB5− cells gave rise exclusively to ABCB5− progeny. This identification of a specific relationship between a chemoresistance mechanism and cancer stem cells in a human malignancy has important implications for stem cell-targeted approaches to cancer therapy.

It has also been discovered according to the invention that ablation of ABCB5+ melanoma cells via targeted immunotherapeutic approaches may represent a new strategy for achieving more durable clinical responses than those obtained by therapeutic strategies directed predominantly at the bulk population of tumor cells. Therefore, we investigated whether selective ablation of chemoresistant, tumorigenic human ABCB5+ melanoma stem cells via systemic administration of an anti-ABCB5 monoclonal antibody (mAb clone 3C2-1D12) facilitates inhibition of tumor formation/tumor eradication in a relevant preclinical animal model of human malignant melanoma involving human to nude mouse tumor xenografts.

As shown in more detail below, we examined the bioavailability and melanoma-binding efficacy/specificity of in vivo administered anti-ABCB5 mAb in a human to mouse melanoma xenograft model. In order to examine whether administration of anti-ABCB5 mAb results in detectable in vivo serum levels, mouse sera was incubated with freshly harvested human melanoma cell cultures, followed by counterstaining of cells with FITC-conjugated goat anti-mouse Ig secondary Ab and subsequent analysis by single color flow cytometry. Significant binding of FITC-conjugated goat anti-mouse Ig secondary Ab to those melanoma cultures pre-incubated with sera at all tested dilutions derived from anti-ABCB5 mAb-treated mice was observed. Binding was not observed with sera derived from either isotype control-treated or untreated animals. The detection of 5.4% ABCB5 positivity at sera dilutions as low as 1:100 (FIG. 1A) was consistent with the previously reported ABCB5+ cell frequency among in vitro-cultured G3361 melanoma cells (Frank, N. Y. et al. ABCB5-mediated doxorubicin transport and chemoresistance in human malignant melanoma. Cancer Res 65, 4320-33 (2005); Frank, N. Y. et al. Regulation of progenitor cell fusion by ABCB5 P-glycoprotein, a novel human ATP-binding cassette transporter. J. Biol Chem 278, 47156-65 (2003)). These findings demonstrate that systemically administered anti-ABCB5 mAb results in effective in vivo mAb serum levels. The data described herein further demonstrate that systemically administered anti-ABCB5 mAb efficiently and preferentially binds xenografted ABCB5+ human melanoma cells in vivo, providing evidence for its suitability for in vivo therapeutic targeting approaches. Using human melanoma cells xenografts into nude mice, it was demonstrated that specific targeting of the ABCB5+ melanoma stem cell compartment with antibodies was an effective stem cell-targeted approach to melanoma therapy.

The invention is based in part on the discovery, isolation and characterization of ABCB5 binding molecules, such as human monoclonal antibodies that bind to ABCB5 and are useful in the treatment of cancer. ABCB5 is a multidrug resistance transporter that is present in cancerous stem cells.

Thus, the compositions of the invention may be useful in the treatment of a subject having or at risk of having cancer. A subject shall mean a human or vertebrate mammal including but not limited to a dog, cat, horse, goat and primate, e.g., monkey. Thus, the invention can also be used to treat diseases or conditions in non human subjects. For instance, cancer is one of the leading causes of death in companion animals (i.e., cats and dogs). Preferably the subject is a human.

As used herein, the term treat, treated, or treating when used with respect to a disorder such as cancer refers to a prophylactic treatment which increases the resistance of a subject to development of the disease or, in other words, decreases the likelihood that the subject will develop the disease as well as a treatment after the subject has developed the disease in order to fight the disease, prevent the disease from becoming worse, or slow the progression of the disease compared to in the absence of the therapy.

A subject at risk of developing a cancer is one who has a high probability of developing cancer. These subjects include, for instance, subjects having a genetic abnormality, the presence of which has been demonstrated to have a correlative relation to a higher likelihood of developing a cancer and subjects exposed to cancer causing agents such as tobacco, asbestos, or other chemical toxins, or a subject who has previously been treated for cancer and is in apparent remission. A subject at risk of having cancer also includes a subject having precancerous lesions. A precancerous lesion is an area of tissue that has altered properties and carries the risk of turning into skin cancer. Precancerous lesions may be caused by, for instance, UV radiation, genetics, exposure to carcinogens such as arsenic, tar or x-ray radiation.

A subject having a cancer is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. Preferably the cancer includes cancer stem cells that express ABCB5.

Optionally, prior to the treatment the presence of ABCB5 positive stem cells can be detected using the binding molecules described herein. The detection or diagnosis, methods provided by the invention generally involve contacting one or more molecules of the invention with a sample in or from a subject. Preferably, the sample is first harvested from the subject, although in vivo detection methods are also envisioned. The sample may include any body tissue or fluid that is suspected of harboring the cancer stem cells. For example, the stem cells are commonly found in or around the tumor mass.

In some aspects, the invention provides binding molecules such as peptides, antibodies, antibody fragments and small molecules. The molecules of the invention bind to ABCB5 and enhance tumor killing. The binding molecules are referred to herein as isolated molecules that selectively bind to ABCB5. It is to be understood that such antibodies are able to bind ABCB5 regardless of its source. Accordingly, antibodies of the invention that are defined as binding to, for example, melanoma cell ABCB5 and capable of detecting and/or enhancing anti-tumor effects in, for example, melanoma cells as well as other cancers, such as breast cancer.

Although not intending to be bound by any particular theory, it is believed that treatment of tumors and cancers may fail because tumorigenic stem cells are not effectively targeted by conventional treatments. The ABCB5 binding molecules of the invention specifically target and are involved in the destruction of these cells. Thus, when these molecules are used alone or in combination with conventional therapies the most aggressive cells of the tumor can be killed.

There are several possible mechanisms by which anti-ABCB5 mAb treatment may inhibit in vivo tumorigenic growth and tumor viability of human melanoma xenografts in this recipient nude mouse model, including antibody-dependent cell-mediated cytotoxicity (ADCC), complement-mediated cytotoxicity (CDC) or antibody-dependent macrophage-mediated cytotoxicity (ABMC), and/or inhibition of ABCB5 function, which may contribute to stem cell tumorigenicity. Any of these mechanisms are predicted to target only the ABCB5-expressing tumor cell subset compared to controls. We also expect anti-ABCB5 mAb-mediated in vivo therapeutic targeting of ABCB5+ melanoma stem cells via chemosensitization- or immunotoxin-mediated cell ablation strategies. Since ABCB5-targeted delivery of toxins (chemical or biological toxins, radionuclides) or of ABCB5 mAb-conjugated siRNAs toward additional tumor stem cell-specific gene targets might require cellular toxin internalization, we also examined cellular internalization of anti-ABCB5 mAb following surface binding to ABCB5+ human melanoma cells. The results indicate that anti-ABCB5 mAb-conjugated toxins can be specifically delivered to intracellular compartments in chemoresistant ABCB5+ human melanoma cells, highlighting a therapeutic advantage of this novel approach for the treatment of clinical melanoma and other cancers.

A molecule that selectively binds to ABCB5 as used herein refers to a molecule, e.g, small molecule, peptide, antibody, fragment, that interacts with ABCB5 and optionally interferes with the ABCB5 activity. In some embodiments the molecules are peptides.

The peptides of the invention minimally comprise regions that bind to ABCB5. ABCB5-binding regions, in some embodiments derive from the ABCB5-binding regions of the antibodies of the invention, or alternatively, they are functionally equivalent variants of such regions. Accordingly, two particularly important classes of antibody-derived ABCB5-binding regions are variable regions and CDRs of the antibodies described herein. CDR and variable region nucleic acids can be cloned from antibody-producing cells or prepared synthetically based on the sequences described herein.

The term "antibody" herein is used in the broadest sense and specifically covers intact monoclonal antibodies, polyclonal antibodies, multispecific antibodies (e.g. bispecific antibodies) formed from at least two intact antibodies, antibody fragments, so long as they exhibit the desired biological activity, and antibody like molecules such as scFv. A native antibody usually refers to heterotetrameric glycoproteins composed of two identical light (L) chains and two identical heavy (H) chains. Each heavy and light chain has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

Certain portions of the variable domains differ extensively in sequence among antibodies and are used in the binding and specificity of each particular antibody for its particular antigen. However, the variability is not evenly distributed throughout the variable domains of antibodies. It is concentrated in three or four segments called "complementarity-determining regions" (CDRs) or "hypervariable regions" in both in the light-chain and the heavy-chain variable domains. The more highly conserved portions of variable domains are called the framework (FR). The variable domains of native heavy and light chains each comprise four or five FR regions, largely adopting a β-sheet configuration, connected by the CDRs, which form loops connecting, and in some cases forming part of, the n-sheet structure. The CDRs in each chain are held together in close proximity by the FR regions and, with the CDRs from the other chain, contribute to the formation of the antigen-binding site of antibodies (see Kabat et al., NIH Publ. No. 91-3242, Vol. I, pages 647-669 (1991)). The constant domains are not necessarily involved directly in binding an antibody to an antigen, but exhibit various effector functions, such as participation of the antibody in antibody-dependent cellular toxicity.

A hypervariable region or CDR as used herein defines a subregion within the variable region of extreme sequence variability of the antibody, which form the antigen-binding site and are the main determinants of antigen specificity. According to one definition, they can be residues (Kabat nomenclature) 24-34 (L1), 50-56 (L2) and 89-97 (L3) in the light chain variable region and residues (Kabat nomenclature 31-35 (H1), 50-65 (H2), 95-102 (H3) in the heavy chain variable region. Kabat et al., Sequences of Proteins of Immunological Interest, 5th Ed. Public Health Service, National Institute of Health, Bethesda, Md. [1991]).

An "intact" antibody is one which comprises an antigen-binding variable region as well as a light chain constant domain ($C_L$) and heavy chain constant domains, $C_{H1}$, $C_{H2}$ and $C_{H3}$. The constant domains may be native sequence constant domains (e.g. human native sequence constant domains) or amino acid sequence variant thereof. Preferably, the intact antibody has one or more effector functions. Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. For example, the antibody fragments can be isolated from antibody phage libraries. Alternatively, Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture.

"Antibody fragments" comprise a portion of an intact antibody, preferably the antigen binding or variable region of the intact antibody. Examples of antibody fragments include Fab, Fab', F(ab')$_2$, and Fv fragments; diabodies; single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain. By "Fc region chain" herein is meant one of the two polypeptide chains of an Fc region.

The "hinge region," and variations thereof, as used herein, includes the meaning known in the art, which is illustrated in, for example, Janeway et al., Immuno Biology: the immune system in health and disease, (Elsevier Science Ltd., NY) (4th ed., 1999)

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The "light chains" of antibodies (immunoglobulins) from any vertebrate species can be assigned to one of two clearly distinct types, called kappa (κ) and lambda (λ), based on the amino acid sequences of their constant domains.

Preferably, the ABCB5-binding peptides minimally encompass at least one CDR from those described herein or those that can be derived from the sequences described herein. As used herein, an ABCB5-binding CDR is a CDR described herein. The ABCB5-binding region may be an ABCB5-binding CDR1, an ABCB5-binding CDR2, or an ABCB5-binding CDR3, all of which are derived from the antibodies and antibody variable chains disclosed herein.

As used herein, an "ABCB5-binding CDR1" is a CDR1 that binds, preferably specifically, to ABCB5, and is derived from either the heavy or light chain variable regions of the antibodies described herein. It may have an amino acid sequence selected from the group consisting of SEQ ID NO: 3 and SEQ ID NO: 6. An "ABCB5-binding CDR2" is a CDR2 that binds, preferably specifically, to ABCB5, and is derived from either the heavy or light chain variable regions of the antibodies described herein. It may have an amino acid sequence selected from the group consisting of SEQ ID NO: 4 and SEQ ID NO: 7. An "ABCB5-binding CDR3" is a CDR3 that binds, preferably specifically, to ABCB5, and is derived from either the heavy or light chain variable regions of the antibodies described herein. It may have an amino acid sequence selected from the group consisting of SEQ ID NO: 5 and SEQ ID NO: 8.

In addition to the sequences listed herein, the invention intends to embrace functionally equivalent variants of these sequences including conservative substitution variants in either the amino acid or nucleotide sequence, as described in greater detail below.

The peptides of the invention are useful inter alia in diagnostic methods aimed at detecting, in a sample or from a subject, the ABCB5 antigen or ABCB5-expressing cells. At a minimum, peptides useful in these methods need only recognize and bind to ABCB5 regardless of whether they also enhance tumor killing. The antibodies may be employed, for instance, in diagnostic FACS analysis, Western blotting, and immunohistochemistry. Such antibodies may also be employed for in vivo diagnostic uses, where label-conjugated mAbs can be used to assess tumor burden, tumor localization or residual tumor mass following chemotherapy or surgical therapy of ABCB5-expressing tumors. In important embodiments, the antibodies and fragments thereof bind to ABCB5 selectively. In some embodiments, they only possess one or more of the CDRs derived from the antibody clones described herein. In preferred embodiments, the peptides comprise an ABCB5-binding CDR3, and even more preferably, the peptides comprise a heavy chain ABCB5-binding CDR3. It is to be understood that not all of the CDRs are required in order to effect binding to ABCB5. However, in some embodiments the peptides comprise all of the CDRs of a given antibody clone disclosed herein.

In addition, it should be understood that the invention also embraces the exchange of CDRs between the variable regions provided herein. Preferably, a heavy chain CDR is exchanged with another heavy chain variable region CDR, and likewise, a light chain CDR is exchanged with another light chain variable region CDR.

The peptides may also comprise an ABCB5-binding variable region. An ABCB5-binding variable region is a variable region (preferably an antibody variable region as described herein). SEQ ID NO: 1 corresponds to the amino acid sequences of the heavy chain variable region. SEQ ID NO: 9 corresponds to the nucleotide sequence of the heavy chain variable region. SEQ ID NO: 2 corresponds to the amino acid sequences of the light chain variable region. SEQ ID NO: 10 corresponds to the nucleotide sequence of the light chain variable region.

It is to be understood that the nucleic acids or peptides of the invention may be derived from the sequences provided herein. These sequences can be cloned (e.g., by PCR) and inserted into a vector and/or cells in order to produce peptides corresponding to full length variable regions or fragments of full length variable regions, and antibodies comprising the variable regions. It is therefore possible to generate antibodies or fragments thereof that comprise a combination of light and heavy chain variable regions.

The invention intends to capture antibody and antibody fragments of various isotypes. The antibodies may be of an IgG1, IgG2, IgG3, IgG4, IgD, IgE, IgM, IgA1, IgA2, or sIgA isotype. The invention intends to capture isotypes found in non-human species as well such as but not limited to IgY in birds and sharks. Vectors encoding the constant regions of various isotypes are known and previously described. (See, for example, Coloma et al. Novel vectors for the expression of antibody molecules using variable regions generated by polymerase chain reaction. J Immunol Methods. 1992 Jul. 31; 152(1):89-104; Guttieri et al. Cassette vectors for conversion of Fab fragments into full-length human IgG1 monoclonal antibodies by expression in stably transformed insect cells. Hybrid Hybridomics. 2003 June; 22(3):135-45; McLean et al. Human and murine immunoglobulin expression vector cassettes. Mol Immunol. 2000 October; 37(14):837-45; Walls et al. Vectors for the expression of PCR-amplified immunoglobulin variable domains with human constant regions. Nucleic Acids Res. 1993 Jun. 25; 21(12):2921-9; Norderhaug et al. Versatile vectors for transient and stable expression of recombinant antibody molecules in mammalian cells. J Immunol Methods. 1997 May 12; 204(1):77-87.)

The peptides of the invention are isolated peptides. As used herein, the term "isolated peptides" means that the peptides are substantially pure and are essentially free of other substances with which they may be found in nature or in vivo systems to an extent practical and appropriate for their intended use. In particular, the peptides are sufficiently pure and are sufficiently free from other biological constituents of their hosts cells so as to be useful in, for example, producing pharmaceutical preparations or sequencing. Because an isolated peptide of the invention may be admixed with a pharmaceutically acceptable carrier in a pharmaceutical preparation, the peptide may comprise only a small percentage by weight of the preparation. The peptide is nonetheless substantially pure in that it has been substantially separated from the substances with which it may be associated in living systems.

The peptides of the invention bind to ABCB5, preferably in a selective manner. As used herein, the terms "selective binding" and "specific binding" are used interchangeably to refer to the ability of the peptide to bind with greater affinity to ABCB5 and fragments thereof than to non-ABCB5 derived compounds. That is, peptides that bind selectively to ABCB5 will not bind to non-ABCB5 derived compounds to the same extent and with the same affinity as they bind to ABCB5 and fragments thereof, with the exception of cross reactive antigens or molecules made to be mimics of ABCB5 such as peptide mimetics of carbohydrates or variable regions of anti-idiotype antibodies that bind to the ABCB5-binding peptides in the same manner as ABCB5. In some embodiments, the peptides of the invention bind solely to ABCB5 and fragments thereof. As used herein, a binding peptide that binds selectively or specifically to tumor cell ABCB5 may also bind ABCB5 from other sources and will bind with lesser affinity (if at all) to non-ABCB5 derived compounds. Lesser affinity may include at least 10% less, 20% less, 30% less, 40% less, 50% less, 60% less, 70% less, 80% less, 90% less, or 95% less.

"Isolated antibodies" as used herein refer to antibodies that are substantially physically separated from other cellular material (e.g., separated from cells which produce the antibodies) or from other material that hinders their use either in the diagnostic or therapeutic methods of the invention. Preferably, the isolated antibodies are present in a homogenous population of antibodies (e.g., a population of monoclonal antibodies). Compositions of isolated antibodies can however be combined with other components such as but not limited to pharmaceutically acceptable carriers, adjuvants, and the like.

"Isolated antibody producing cells" including isolated hybridomas and isolated recombinant cells (such as those described herein), as used herein, refer to antibody-producing cells that are substantially physically separated from other cells, other bodily material (e.g., ascites tissue and fluid), and other material that hinders their use in the production of, for example, an isolated and preferably homogenous antibody population.

Thus in one embodiment, the peptide of the invention is an isolated intact soluble monoclonal antibody specific for ABCB5. As used herein, the term "monoclonal antibody" refers to a homogenous population of immunoglobulins that specifically bind to an identical epitope (i.e., antigenic determinant). The peptide of the invention in one embodiment is, for example, a monoclonal antibody having a heavy chain variable region having an amino acid sequence of SEQ ID NO:1 and a light chain variable region having an amino acid sequence of SEQ ID NO:2. Monoclonal antibodies having any combination of light chain and heavy chain variable regions are embraced by the invention.

The invention intends to encompass antibodies other than, for example, the sequences of 3C2-1D12, provided that such antibodies have the binding characteristics of the monoclonal antibodies described herein. Optionally, these additional antibodies also enhance tumor killing of ABCB5-expressing cancer cells. One of ordinary skill in the art can easily identify antibodies having the functional characteristics of this monoclonal antibody using the screening and binding assays set forth in detail herein.

Unless indicated otherwise, the term "monoclonal antibody 3C2-1D12" or "mAb3C2-1D12" refers to an antibody that has antigen binding residues of, or derived from, the murine 3C2-1D12 antibody.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pluckthun, Immunol. Revs., 130: 151-188 (1992).

In a further embodiment, monoclonal antibodies or antibody fragments can be isolated from antibody phage libraries generated using the techniques described in McCafferty et al., Nature, 348:552-554 (1990). Clackson et al., Nature, 352: 624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In other embodiments, the peptide is an antibody fragment. As is well-known in the art, only a small portion of an antibody molecule, the paratope, is involved in the binding of the antibody to its epitope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford; and Pier G B, Lyczak J B, Wetzler L M, (eds). Immunology, Infection and Immunity (2004) 1$^{st}$ Ed. American Society for Microbiology Press, Washington D.C.). The pFc' and Fc regions of the antibody, for example, are effectors of the complement cascade and can mediate binding to Fc receptors on phagocytic cells, but are not involved in antigen binding. An antibody from which the pFc' region has been enzymatically cleaved, or which has been produced without the pFc' region, designated an F(ab')$_2$ fragment, retains both of the antigen binding sites of an intact antibody. An isolated F(ab')$_2$ fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', F(ab')$_2$ and Fv are employed with either standard immunological meanings [Klein, Immunology (John Wiley, New York, N.Y., 1982); Clark, W. R. (1986) The Experimental Foundations of Modern Immunology (Wiley & Sons, Inc., New York); Roitt, I. (1991) Essential Immunology, 7th Ed., (Blackwell Scientific Publications, Oxford); and Pier G B, Lyczak J B, Wetzler L M, (eds). Immunology, Infection and Immunity (2004) 1$^{st}$ Ed. American Society for Microbiology Press, Washington D.C.].

In other embodiments, the Fc portions of the antibodies of the invention may be replaced so as to produce IgM as well as human IgG antibodies bearing some or all of the CDRs of the monoclonal antibodies described herein. Of particular importance is the inclusion of a ABCB5-binding CDR3 region and, to a lesser extent, the other CDRs and portions of the framework regions of the monoclonal antibodies described herein. Such human antibodies will have particular clinical utility in that they will recognize and bind, preferably selectively, to ABCB5, but will not evoke an immune response in humans against the antibody itself.

The invention also intends to include functionally equivalent variants of the ABCB5-binding peptides. A "functionally equivalent variant" is a compound having the same function (i.e., the ability to bind to ABCB5) as the peptides of the invention. A functionally equivalent variant may be peptide in nature but it is not so limited. For example, it may be a carbohydrate, a peptidomimetic, etc. In important embodiments, the functionally equivalent variant is a peptide having the amino acid sequence of a variable region or a CDR with conservative substitutions therein, that is still capable of binding to ABCB5. An example of a functionally equivalent variant of ABCB5-binding CDR3 from the heavy chain variable region (i.e., SEQ ID NO:1) is a peptide having conservative substitutions in SEQ ID NO:1 which bind, preferably specifically, to ABCB5, and optionally which enhances tumor killing of ABCB5-expressing cells.

The term "amino acid sequence variant" refers to polypeptides having amino acid sequences that differ to some extent from a native sequence polypeptide. The amino acid sequence variants possess substitutions, deletions, and/or insertions at certain positions within the amino acid sequence of the native amino acid sequence.

"Homology" is defined as the percentage of residues in the amino acid sequence variant that are identical after aligning the sequences and introducing gaps, if necessary, to achieve the maximum percent homology. Methods and computer programs for the alignment are well known in the art.

Amino acid sequence modification of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated.

As used herein, "conservative substitution" refers to an amino acid substitution which does not alter the relative charge or size characteristics of the peptide in which the amino acid substitution is made. Conservative substitutions of amino acids include substitutions made amongst amino acids with the following groups: (1) M,I,L,V; (2) F,Y,W; (3) K,R,H; (4) A,G; (5) S,T; (6) Q,N; and, (7) E,D.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

One type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody used in methods of the invention may comprise one or more alterations as compared to the wild type counterpart antibody, for e.g. in the Fc region, in addition to the hinge sequence mutation described herein. These antibodies would nonetheless retain substantially the same characteristics required for therapeutic utility as compared to their wild type counterpart. For e.g., it is thought that certain alterations can be made in the Fc region that would result in altered (i.e., either improved or diminished) C1q binding and/or Complement Dependent Cytotoxicity (CDC), for e.g., as described in WO99/51642. See also Duncan & Winter Nature 322:738-40 (1988); U.S. Pat. No. 5,648,260; U.S. Pat. No. 5,624,821; and WO94/29351 concerning other examples of Fc region variants.

Any cysteine residue not involved in maintaining the proper conformation of the anti-ABCB5 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Another type of amino acid variant of the antibody alters the original glycosylation pattern of the antibody. By altering is meant deleting one or more carbohydrate moieties found in the antibody, and/or adding one or more glycosylation sites that are not present in the antibody. lycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Functional equivalence refers to an equivalent activity (e.g., binding to ABCB5, or enhancing killing of ABCB5-expressing cells), however it also embraces variation in the level of such activity. For example, a functional equivalent is a variant that binds to ABCB5 with lesser, equal, or greater affinity than the monoclonal antibody clones described herein, provided that the variant is still useful in the invention (i.e., it binds to ABCB5 and optionally enhances tumor killing).

Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding the particular CDR or a peptide comprising the CDR amino acid sequences described herein. These and other methods for altering a CDR containing peptide will be known to those of ordinary skill in the art and may be found in references which compile such methods, e.g. Sambrook or Ausubel, noted above. In some embodiments, however, due to the size of the CDRs, it may be more convenient to synthesize the variant peptides using a peptide synthesizer such as those commercially available. The activity of functionally equivalent variants of the ABCB5-binding CDR can be tested by the binding assays, and in some cases biological activity assays, discussed in more detail below. As used herein, the terms "functional variant", "functionally equivalent variant" and "functionally active variant" are used interchangeably.

As used herein the term "functionally active antibody fragment" means a fragment of an antibody molecule including an ABCB5-binding region of the invention which retains the ability to bind to ABCB5 respectively, preferably in a specific manner. Such fragments can be used both in vitro and in vivo. In particular, well-known functionally active antibody fragments include but are not limited to F(ab)$_2$, Fab, Fv and Fd fragments of antibodies. These fragments which lack the Fc fragment of intact antibody, clear more rapidly from the circulation, and may have less non-specific tissue binding than an intact antibody (Wahl et al., *J. Nucl. Med.* 24:316-325 (1983)). As another example, single-chain antibodies can be constructed in accordance with the methods described in U.S. Pat. No. 4,946,778 to Ladner et al. Such single-chain antibodies include the variable regions of the light and heavy chains joined by a flexible linker moiety. Methods for obtaining a single domain antibody ("Fd") which comprises an isolated variable heavy chain single domain, also have been reported (see, for example, Ward et al., *Nature* 341:644-646 (1989), disclosing a method of screening to identify an antibody heavy chain variable region ($V_H$ single domain antibody) with sufficient affinity for its target epitope to bind thereto in isolated form). Methods for making recombinant Fv fragments based on known antibody heavy chain and light chain variable region sequences are known in the art and have been described, e.g., Moore et al., U.S. Pat. No. 4,462,334. Other references describing the use and generation of antibody fragments include e.g., Fab fragments (Tijssen, Practice and Theory of Enzyme Immunoassays (Elsevier, Amsterdam, 1985)), Fv fragments (Hochman et al., Biochemistry 12: 1130 (1973); Sharon et al., Biochemistry 15: 1591 (1976); Ehrlich et al., U.S. Pat. No. 4,355,023) and portions of antibody molecules (Audilore-Hargreaves, U.S. Pat. No. 4,470,925). Thus, those skilled in the art may construct antibody fragments from various portions of intact antibodies without destroying the specificity of the antibodies for ABCB5.

In important aspects of the invention, the functionally active antibody fragment also retains the ability to enhance killing of ABCB5-expressing cells. In this latter instance, the antibody fragment includes an Fc region as well as an epitope binding domain. The Fc region allows the antibody fragment to bind to Fc receptor positive cells, which subsequently phagocytose the epitope bound by the Fab region of the antibody.

The anti-ABCB5 peptides of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biot, 2:593-596 (1992)].

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., J. Immunol., 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

An exemplary humanized antibody of interest herein comprises variable heavy domain complementarity determining residues DYYMY (SEQ ID NO:3); TINDGGTHTY (SEQ ID NO:4); and/or DDYYYGSHFDAMDY (SEQ ID NO:5), optionally comprising amino acid modifications of those CDR residues, e.g. where the modifications essentially maintain or improve affinity of the antibody. For example, the antibody variant of interest may have from about one to about seven or about five amino acid substitutions in the above variable heavy CDR sequences. Such antibody variants may be prepared by affinity maturation.

The humanized antibody may comprise variable light domain complementarity determining residues RASKSVSTSGYSYMH (SEQ ID NO:6); LVSNLES (SEQ ID NO:7); and/or QHIRELTR (SEQ ID NO:8), e.g. in addition to those variable heavy domain CDR residues in the preceding paragraph. Such humanized antibodies optionally comprise amino acid modifications of the above CDR residues, e.g. where the modifications essentially maintain or improve affinity of the antibody. For example, the antibody variant of interest may have from about one to about seven or about five amino acid substitutions in the above variable light CDR sequences.

The present application also contemplates affinity matured antibodies which bind ABCB5. The parent antibody may be a human antibody or a humanized antibody, e.g., one comprising the variable light and/or heavy sequences of SEQ ID Nos. 2 and 1, respectively. The affinity matured antibody preferably binds to ABCB5 with an affinity superior to that of murine mAb3C2-1D12.

Various forms of the humanized antibody or affinity matured antibody are contemplated. For example, the humanized antibody or affinity matured antibody may be an antibody fragment, such as a Fab, which is optionally conjugated with one or more cytotoxic agent(s) in order to generate an immunoconjugate. Alternatively, the humanized antibody or affinity matured antibody may be an intact antibody, such as an intact IgG1 antibody.

European Patent Application 0239400, the entire contents of which is hereby incorporated by reference, provides an exemplary teaching of the production and use of humanized monoclonal antibodies in which at least the CDR portion of a murine (or other non-human mammal) antibody is included in the humanized antibody. Briefly, the following methods are useful for constructing a humanized CDR monoclonal antibody including at least a portion of a mouse CDR. A first replicable expression vector including a suitable promoter operably linked to a DNA sequence encoding at least a variable domain of an Ig heavy or light chain and the variable domain comprising framework regions from a human antibody and a CDR region of a murine antibody is prepared. Optionally a second replicable expression vector is prepared which includes a suitable promoter operably linked to a DNA sequence encoding at least the variable domain of a complementary human Ig light or heavy chain respectively. A cell line is then transformed with the vectors. Preferably the cell line is an immortalized mammalian cell line of lymphoid origin, such as a myeloma, hybridoma, trioma, or quadroma cell line, or is a normal lymphoid cell which has been immortalized by transformation with a virus. The transformed cell line is then cultured under conditions known to those of skill in the art to produce the humanized antibody.

As set forth in European Patent Application 0239400 several techniques are well known in the art for creating the particular antibody domains to be inserted into the replicable vector. (Preferred vectors and recombinant techniques are discussed in greater detail below.) For example, the DNA sequence encoding the domain may be prepared by oligonucleotide synthesis. Alternatively a synthetic gene lacking the CDR regions in which four framework regions are fused together with suitable restriction sites at the junctions, such that double stranded synthetic or restricted subcloned CDR cassettes with sticky ends could be ligated at the junctions of the framework regions. Another method involves the preparation of the DNA sequence encoding the variable CDR containing domain by oligonucleotide site-directed mutagenesis. Each of these methods is well known in the art. Therefore, those skilled in the art may construct humanized antibodies containing a murine CDR region without destroying the specificity of the antibody for its epitope.

As an alternative to humanization, human antibodies can be generated. A "human antibody" is one which possesses an amino acid sequence which corresponds to that of an antibody produced by a human and/or has been made using any techniques for making human antibodies. This definition of a human antibody specifically excludes a humanized antibody comprising non-human antigen-binding residues. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); and U.S. Pat. Nos. 5,591,669, 5,589,369 and 5,545,807.

Alternatively, phage display technology (McCafferty et al., Nature 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905. Human antibodies may also be generated by in vitro activated B cells (see U.S. Pat. Nos. 5,567,610 and 5,229,275).

Human monoclonal antibodies also may be made by any of the methods known in the art, such as those disclosed in U.S. Pat. No. 5,567,610, issued to Borrebaeck et al., U.S. Pat. No. 565,354, issued to Ostberg, U.S. Pat. No. 5,571,893, issued to Baker et al, Kozber, *J. Immunol.* 133: 3001 (1984), Brodeur, et al., *Monoclonal Antibody Production Techniques and Applications*, p. 51-63 (Marcel Dekker, Inc, new York 1987), and Boerner et al., *J. Immunol.*, 147: 86-95 (1991).

The invention also encompasses the use of single chain variable region fragments (scFv). Single chain variable region fragments are made by linking light and/or heavy chain variable regions by using a short linking peptide. Any peptide having sufficient flexibility and length can be used as a linker in a scFv. Usually the linker is selected to have little to no immunogenicity. An example of a linking peptide is multiple GGGGS residues, which bridge the carboxy terminus of one variable region and the amino terminus of another variable region. Other linker sequences may also be used.

All or any portion of the heavy or light chain can be used in any combination. Typically, the entire variable regions are included in the scFv. For instance, the light chain variable region can be linked to the heavy chain variable region. Alternatively, a portion of the light chain variable region can be linked to the heavy chain variable region, or portion thereof. Also contemplated are scFvs in which the heavy chain variable region is from the antibody of interest, and the light chain variable region is from another immunoglobulin.

The scFvs can be assembled in any order, for example, $V_H$-linker-$V_L$ or $V_L$-linker-$V_H$. There may be a difference in the level of expression of these two configurations in particular expression systems, in which case one of these forms may be preferred. Tandem scFvs can also be made, such as (X)-linker-(X)-linker-(X), in which X are polypeptides form the antibodies of interest, or combinations of these polypeptides with other polypeptides. In another embodiment, single chain antibody polypeptides have no linker polypeptide, or just a short, inflexible linker. Possible configurations are $V_L$-$V_H$ and $V_H$-$V_L$. The linkage is too short to permit interaction between $V_L$ and $V_H$ within the chain, and the chains form homodimers with a $V_L/V_H$ antigen binding site at each end. Such molecules are referred to in the art as "diabodies".

Single chain variable regions may be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*, and the expressed protein may be isolated using standard protein purification techniques.

Conditions of expression should be such that the scFv polypeptide can assume optimal tertiary structure. Depending on the plasmid used and the host cell, it may be necessary to modulate the rate of production. For instance, use of a weaker promoter, or expression at lower temperatures, may be necessary to optimize production of properly folded scFv in prokaryotic systems; or it may be preferably to express scFv in eukaryotic cells.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90: 6444-6448 (1993).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

Bispecific antibodies are monoclonal, preferably human or humanized, antibodies that have binding specificities for at least two different antigens. In the present case, one of the binding specificities is for the ABCB5, the other one is for any other antigen, and preferably for a cell-surface protein or receptor or receptor subunit. Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibodies with more than two valencies are contemplated. For example, trispecific antibodies can be prepared. Tutt et al., J. Immunol. 147: 60 (1991).

Additionally small peptides including those containing the ABCB5-binding CDR3 region may easily be synthesized or produced by recombinant means to produce the peptide of the invention. Such methods are well known to those of ordinary skill in the art. Peptides can be synthesized, for example, using automated peptide synthesizers which are commercially available. The peptides can be produced by recombinant techniques by incorporating the DNA expressing the peptide into an expression vector and transforming cells with the expression vector to produce the peptide.

Peptides, including antibodies, can be tested for their ability to bind to ABCB5 using standard binding assays known in the art. As an example of a suitable assay, ABCB5 can be immobilized on a surface (such as in a well of a multi-well plate) and then contacted with a labeled peptide. The amount of peptide that binds to the ABCB5 (and thus becomes itself immobilized onto the surface) may then be quantitated to determine whether a particular peptide binds to ABCB5. Alternatively, the amount of peptide not bound to the surface may also be measured. In a variation of this assay, the peptide can be tested for its ability to bind directly to a ABCB5-expressing cell.

Peptide binding can also be tested using a competition assay. If the peptide being tested (including an antibody) competes with the monoclonal antibodies or antibody fragments described herein, as shown by a decrease in binding of the monoclonal antibody or fragment, then it is likely that the peptide and the monoclonal antibody bind to the same, or at least an overlapping, epitope. In this assay system, the antibody or antibody fragment is labeled and the ABCB5 is immobilized onto the solid surface. In this way, competing peptides including competing antibodies can be identified. The invention embraces peptides and in particular antibodies (and fragments thereof) that compete with antibody 3C2 1D12 for binding to ABCB5 (i.e., antibodies that recognize and bind to the same epitopes as 3C2 1D12.

The invention also encompasses small molecules that bind to ABCB5 and enhance tumor killing. Such binding molecules may be identified by conventional screening methods, such as phage display procedures (e.g. methods described in Hart et al., J. Biol. Chem. 269:12468 (1994)). Hart et al. report a filamentous phage display library for identifying novel peptide ligands. In general, phage display libraries using, e.g., M13 or fd phage, are prepared using conventional procedures such as those described in the foregoing reference. The libraries generally display inserts containing from 4 to 80 amino acid residues. The inserts optionally represent a completely degenerate or biased array of peptides. Ligands having the appropriate binding properties are obtained by selecting those phage which express on their surface a ligand that binds to the target molecule. These phage are then subjected to several cycles of reselection to identify the peptide ligand expressing phage that have the most useful binding characteristics. Typically, phage that exhibit the best binding characteristics (e.g., highest affinity) are further characterized by nucleic acid analysis to identify the particular amino acid sequences of the peptide expressed on the phage surface in the optimum length of the express peptide to achieve optimum binding. Phage-display peptide or antibody library is also described in Brissette R et al Curr Opin Drug Discov Devel. 2006 May; 9(3): 363-9.

Alternatively, binding molecules can be identified from combinatorial libraries. Many types of combinatorial libraries have been described. For instance, U.S. Pat. Nos. 5,712,171 (which describes methods for constructing arrays of synthetic molecular constructs by forming a plurality of molecular constructs having the scaffold backbone of the chemical molecule and modifying at least one location on the molecule in a logically-ordered array); 5,962,412 (which describes methods for making polymers having specific physiochemical properties); and 5,962,736 (which describes specific arrayed compounds).

Other binding molecules may be identified by those of skill in the art following the guidance described herein. Library technology can be used to identify small molecules, including small peptides, which bind to ABCB5 and interrupt its function. One advantage of using libraries for antagonist identification is the facile manipulation of millions of different putative candidates of small size in small reaction volumes (i.e., in synthesis and screening reactions). Another advantage of libraries is the ability to synthesize antagonists which might not otherwise be attainable using naturally occurring sources, particularly in the case of non-peptide moieties.

Small molecule libraries can be screened for their modulatory effects on ABCB5-mediated rhodamine-123 efflux transport, from which binding to ABCB5 can be inferred. Potential substrates or inhibitors of ABCB5 function can also be identified by correlating ABCB5 gene or protein expression across the NCI-60 panel of cancer cell lines of the National Cancer Institute with established drug potencies of >100,000 compounds for these cell lines, similar as described in Frank et al. Cancer Research 2005 for a select 119 standard anticancer agents.

Many if not all of these compounds can be synthesized using recombinant or chemical libraries. A vast array of candidate compounds can be generated from libraries of synthetic or natural compounds. Libraries of natural compounds in the form of bacterial, fungal, plant and animal extracts are available or can readily produced. Natural and synthetically produced libraries and compounds can be readily modified through conventional chemical, physical, and biochemical means. In addition, compounds known to bind to and thereby act as antagonists of calcium channels may be subjected to directed or random chemical modifications such as acylation, alkylation, esterification, amidification, etc. to produce structural analogs which may function similarly or perhaps with greater specificity.

Small molecule combinatorial libraries may also be generated. A combinatorial library of small organic compounds is a collection of closely related analogs that differ from each other in one or more points of diversity and are synthesized by organic techniques using multi-step processes. Combinatorial libraries include a vast number of small organic compounds. One type of combinatorial library is prepared by means of parallel synthesis methods to produce a compound array. A "compound array" as used herein is a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in PCT published patent application WO95/18972, published Jul. 13, 1995 and U.S. Pat. No. 5,712,171 granted Jan. 27, 1998 and its corresponding PCT published patent application WO96/22529, which are hereby incorporated by reference.

Standard binding assays are well known in the art, and a number of these are suitable in the present invention including ELISA, competition binding assay (as described above), sandwich assays, radioreceptor assays using radioactively labeled peptides or radiolabeled antibodies, immunoassays, etc. The nature of the assay is not essential provided it is sufficiently sensitive to detect binding of a small number of peptides.

A variety of other reagents also can be included in the binding mixture. These include reagents such as salts, buffers, neutral proteins (e.g., albumin), detergents, etc. which may be used to facilitate optimal binding. Such a reagent may also reduce non-specific or background interactions of the reaction components. Other reagents that improve the efficiency of the assay may also be used. The mixture of the foregoing assay materials is incubated under conditions under which the monoclonal antibody normally specifically binds ABCB5. Such conditions will preferably mimic physiological conditions. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours. After incubation, the presence or absence of specific binding between the peptide and ABCB5 is detected by any convenient method available to the user.

Typically, a plurality of assay mixtures are run in parallel with different peptides or different peptide concentrations to obtain a different response to the various concentrations. One of these concentrations serves as a negative control, i.e., at zero concentration of ABCB5 or at a concentration of ABCB5 below the limits of assay detection.

A separation step is often used to separate bound from unbound peptide or antibody. The separation step may be accomplished in a variety of ways. Conveniently, at least one of the components (e.g., peptide or antibody) is immobilized on a solid substrate via binding to ABCB5. The unbound components may be easily separated from the bound fraction. The solid substrate can be made of a wide variety of materials and in a wide variety of shapes, e.g., columns or gels of polyacrylamide, agarose or sepharose, microtiter plates, microbeads, resin particles, etc. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

The molecules described herein can be used alone or in conjugates with other molecules such as detection or cytotoxic agents in the detection and treatment methods of the invention, as described in more detail herein.

Typically, one of the components usually comprises, or is coupled or conjugated to a detectable label. A detectable label is a moiety, the presence of which can be ascertained directly or indirectly. Generally, detection of the label involves an emission of energy by the label. The label can be detected directly by its ability to emit and/or absorb photons or other atomic particles of a particular wavelength (e.g., radioactivity, luminescence, optical or electron density, etc.). A label can be detected indirectly by its ability to bind, recruit and, in some cases, cleave another moiety which itself may emit or absorb light of a particular wavelength (e.g., epitope tag such as the FLAG epitope, enzyme tag such as horseradish peroxidase, etc.). An example of indirect detection is the use of a first enzyme label which cleaves a substrate into visible products. The label may be of a chemical, peptide or nucleic acid molecule nature although it is not so limited. Other detectable labels include radioactive isotopes such as $P^{32}$ or $H^3$, luminescent markers such as fluorochromes, optical or electron density markers, etc., or epitope tags such as the FLAG epitope or the HA epitope, biotin, avidin, and enzyme tags such as horseradish peroxidase, β-galactosidase, etc. The label may be bound to a peptide during or following its synthesis. There are many different labels and methods of labeling known to those of ordinary skill in the art. Examples of the types of labels that can be used in the present invention include enzymes, radioisotopes, fluorescent compounds, colloidal metals, chemiluminescent compounds, and bioluminescent compounds. Those of ordinary skill in the art will know of other suitable labels for the peptides described herein, or will be able to ascertain such, using routine experimentation. Furthermore, the coupling or conjugation of these labels to the peptides of the invention can be performed using standard techniques common to those of ordinary skill in the art.

Another labeling technique which may result in greater sensitivity consists of coupling the molecules described herein to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

Conjugation of the peptides including antibodies or fragments thereof to a detectable label facilitates, among other things, the use of such agents in diagnostic assays. Another category of detectable labels includes diagnostic and imaging labels (generally referred to as in vivo detectable labels) such as for example magnetic resonance imaging (MRI): Gd(DOTA); for nuclear medicine: $^{201}$Tl, gamma-emitting radionuclide 99 mTc; for positron-emission tomography (PET): positron-emitting isotopes, (18)F-fluorodeoxyglucose ((18)FDG), (18)F-fluoride, copper-64, gadodiamide, and radioisotopes of Pb(II) such as 203Pb; 111In.

The conjugations or modifications described herein employ routine chemistry, which chemistry does not form a part of the invention and which chemistry is well known to those skilled in the art of chemistry. The use of protecting groups and known linkers such as mono- and hetero-bifunctional linkers are well documented in the literature and will not be repeated here.

As used herein, "conjugated" means two entities stably bound to one another by any physiochemical means. It is important that the nature of the attachment is such that it does not impair substantially the effectiveness of either entity.

Keeping these parameters in mind, any covalent or non-covalent linkage known to those of ordinary skill in the art may be employed. In some embodiments, covalent linkage is preferred. Noncovalent conjugation includes hydrophobic interactions, ionic interactions, high affinity interactions such as biotin-avidin and biotin-streptavidin complexation and other affinity interactions. Such means and methods of attachment are well known to those of ordinary skill in the art.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

The conjugates of the invention also include an antibody conjugated to a cytotoxic agent such as a chemotherapeutic agent, toxin (e.g. an enzymatically active toxin of bacterial, fungal, plant or animal origin, or fragments thereof, or a small molecule toxin), or a radioactive isotope (i.e., a radioconjugate). Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296). Enzymatically active toxins and fragments thereof which can be used in the conjugates include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes.

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99}m$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as tc.sup.99m or I.sup.123, .Re.sup.186, Re.sup.188 and In.sup.111 can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The sequences responsible for the specificity of the monoclonal antibodies of the invention have been determined. Accordingly, peptides according to the invention can be prepared using recombinant DNA technology. There are entities in the United States which will perform this function commercially, such as Thomas Jefferson University and the Scripps Protein and Nucleic Acids Core Sequencing Facility (La Jolla, Calif.). For example, the variable region cDNA can be prepared by polymerase chain reaction using degenerate or non-degenerate primers (derived from the amino acid sequence). The cDNA can be subcloned to produce sufficient quantities of double stranded DNA for sequencing by conventional sequencing reactions or equipment.

With knowledge of the nucleic acid sequences of the heavy chain and light chain variable domains of the anti-ABCB5 monoclonal antibody, one of ordinary skill in the art is able to produce nucleic acids which encode this antibody or which encode the various antibody fragments, humanized antibodies, or polypeptides described above. It is contemplated that such nucleic acids will be operably joined to other nucleic acids forming a recombinant vector for cloning or for expression of the peptides of the invention. The present invention includes any recombinant vector containing the coding sequences, or part thereof, whether for prokaryotic or eukaryotic transformation, transfection or gene therapy. Such vectors may be prepared using conventional molecular biology techniques, known to those with skill in the art, and would comprise DNA coding sequences for the CDR region (and preferably the CDR3 region) and additional variable sequences contributing to the specificity of the antibodies or parts thereof, as well as other non-specific peptide sequences and a suitable promoter either with (Whittle et al., *Protein Eng.* 1:499, 1987 and Burton et al., *Science* 266:1024-1027, 1994) or without (Marasco et al., *Proc. Natl. Acad. Sci.* (*USA*) 90:7889, 1993 and Duan et al., *Proc. Natl. Acad. Sci.* (*USA*) 91:5075-5079, 1994) a signal sequence for export or secretion. Such vectors may be transformed or transfected into prokaryotic (Huse et al., *Science* 246:1275, 1989, Ward et al., *Nature* 341: 644-646, 1989; Marks et al., *J. Mol. Biol.* 222: 581, 1991 and Barbas et al., *Proc. Natl. Acad. Sci.* (*USA*) 88:7978, 991) or eukaryotic (Whittle et al., 1987 and Burton et al., 1994) cells or used for gene therapy (Marasco et al., 1993 and Duan et al., 1994) by conventional techniques, known to those with skill in the art.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

The expression vectors of the present invention include regulatory sequences operably joined to a nucleotide sequence encoding one of the peptides of the invention. As used herein, the term "regulatory sequences" means nucleotide sequences which are necessary for, or conducive to, the transcription of a nucleotide sequence which encodes a desired polypeptide and/or which are necessary for or conducive to the translation of the resulting transcript into the desired polypeptide. Regulatory sequences include, but are not limited to, 5' sequences such as operators, promoters and ribosome binding sequences, and 3' sequences such as polyadenylation signals. The vectors of the invention may optionally include 5' leader or signal sequences, 5' or 3' sequences encoding fusion products to aid in protein purification, and various markers which aid in the identification or selection of transformants. The choice and design of an appropriate vector is within the ability and discretion of one of ordinary skill in the art. The subsequent purification of the peptides may be accomplished by any of a variety of standard means known in the art.

A preferred vector for screening peptides, but not necessarily preferred for the mass production of the peptides of the invention, is a recombinant DNA molecule containing a nucleotide sequence that codes for and is capable of expressing a fusion polypeptide containing, in the direction of amino- to carboxy-terminus, (1) a prokaryotic secretion signal domain, (2) a polypeptide of the invention, and, optionally, (3) a fusion protein domain. The vector includes DNA regulatory sequences for expressing the fusion polypeptide, preferably prokaryotic regulatory sequences. Such vectors can be constructed by those with skill in the art and have been described by Smith et al. (*Science* 228:1315-1317, 1985), Clackson et al. (*Nature* 352:624-628, 1991); Kang et al. (in "Methods: A Companion to Methods in Enzymology: Vol. 2", R. A. Lerner and D. R. Burton, ed. Academic Press, NY, pp 111-118, 1991); Barbas et al. (*Proc. Natl. Acad. Sci.* (*USA*) 88:7978-7982, 1991), Roberts et al. (*Proc. Natl. Acad. Sci.* (*USA*) 89:2429-2433, 1992)

A fusion polypeptide may be useful for purification of the peptides of the invention. The fusion domain may, for example, include a poly-His tail which allows for purification on Ni+ columns or the maltose binding protein of the commercially available vector pMAL (New England BioLabs, Beverly, Mass.). A currently preferred, but by no means necessary, fusion domain is a filamentous phage membrane anchor. This domain is particularly useful for screening phage display libraries of monoclonal antibodies but may be of less utility for the mass production of antibodies. The filamentous phage membrane anchor is preferably a domain of the cpIII or cpVIII coat protein capable of associating with the matrix of a filamentous phage particle, thereby incorporating the fusion polypeptide onto the phage surface, to enable solid phase binding to specific antigens or epitopes and thereby allow enrichment and selection of the specific antibodies or fragments encoded by the phagemid vector.

The secretion signal is a leader peptide domain of a protein that targets the protein membrane of the host cell, such as the periplasmic membrane of gram negative bacteria. A preferred secretion signal for *E. coli* is a pelB secretion signal. The predicted amino acid residue sequences of the secretion signal domain from two pelB gene producing variants from *Erwinia carotova* are described in Lei, et al. (Nature 381:543-546, 1988). The leader sequence of the pelB protein has previously been used as a secretion signal for fusion proteins (Better, et al., *Science* 240:1041-1043, 1988; Sastry, et al., *Proc. Natl. Acad. Sci.* (*USA*) 86:5728-5732, 1989; and Mullinax, et al., *Proc. Natl. Acad. Sci.* (*USA*) 87:8095-8099, 1990). Amino acid residue sequences for other secretion signal polypeptide domains from *E. coli* useful in this invention can be found in Oliver, In Neidhard, F.C. (ed.), *Escherichia coli* and *Salmonella Typhimurium*, American Society for Microbiology, Washington, D.C., 1:56-69 (1987).

To achieve high levels of gene expression in *E. coli*, it is necessary to use not only strong promoters to generate large quantities of mRNA, but also ribosome binding sites to ensure that the mRNA is efficiently translated. In *E. coli*, the ribosome binding site includes an initiation codon (AUG) and a sequence 3-9 nucleotides long located 3-11 nucleotides upstream from the initiation codon (Shine, et al., *Nature* 254:34, 1975). The sequence, AGGAGGU, which is called the Shine-Dalgarno (SD) sequence, is complementary to the 3' end of *E. coli* 16S rRNA. Binding of the ribosome to mRNA and the sequence at the 3' end of the mRNA can be affected by several factors: (i) the degree of complementarity between the SD sequence and 3' end of the 16S rRNA; (ii) the spacing and possibly the DNA sequence lying between the SD sequence and the AUG (Roberts, et al., *Proc. Natl. Acad. Sci.* (*USA*) 76:760, 1979a: Roberts, et al., *Proc. Natl. Acad. Sci.* (*USA*) 76:5596, 1979b; Guarente, et al., *Science* 209:1428, 1980; and Guarente, et al., *Cell* 20:543, 1980). Optimization is achieved by measuring the level of expression of genes in plasmids in which this spacing is systematically altered. Comparison of different mRNAs shows that there are statistically preferred sequences from positions −20 to +13 (where the A of the AUG is position 0) (Gold, et al., *Annu. Rev. Microbiol.* 35:365, 1981). Leader sequences have been shown to influence translation dramatically (Roberts, et al., 1979a, b supra); and (iii) the nucleotide sequence following the AUG, which affects ribosome binding (Taniguchi, et al., *J. Mol. Biol.*, 118:533, 1978).

The 3' regulatory sequences define at least one termination (stop) codon in frame with and operably joined to the heterologous fusion polypeptide.

In a prokaryotic expression host, the vector utilized includes a prokaryotic origin of replication or replicon, i.e., a DNA sequence having the ability to direct autonomous replication and maintenance of the recombinant DNA molecule extra-chromosomally in a prokaryotic host cell, such as a bacterial host cell, transformed therewith. Such origins of replication are well known in the art. Preferred origins of replication are those that are efficient in the host organism. A prokaryotic host cell, for instance, is *E. coli*. For use of a vector in *E. coli*, a preferred origin of replication is ColE1 found in pBR322 and a variety of other common plasmids. Also preferred is the p15A origin of replication found on pACYC and its derivatives. The ColE1 and p15A replicons have been extensively utilized in molecular biology, are available on a variety of plasmids and are described by Sambrook. et al., *Molecular Cloning: A Laboratory Manual,* 2nd edition, Cold Spring Harbor Laboratory Press, 1989).

In addition, those embodiments that include a prokaryotic replicon preferably also include a gene whose expression confers a selective advantage, such as drug resistance, to a bacterial host transformed therewith. Typical bacterial drug resistance genes are those that confer resistance to ampicillin, tetracycline, neomycin/kanamycin or chloramphenicol. Vectors typically also contain convenient restriction sites for insertion of translatable DNA sequences. Exemplary vectors are the plasmids pUC18 and pUC19 and derived vectors such as pcDNAII available from Invitrogen (San Diego, Calif.).

When the peptide of the invention is an antibody including both heavy chain and light chain sequences, these sequences may be encoded on separate vectors or, more conveniently, may be expressed by a single vector. The heavy and light chain may, after translation or after secretion, form the heterodimeric structure of natural antibody molecules. Such a heterodimeric antibody may or may not be stabilized by disulfide bonds between the heavy and light chains.

A vector for expression of heterodimeric antibodies, such as the intact antibodies of the invention or the F(ab')$_2$, Fab or Fv fragment antibodies of the invention, is a recombinant DNA molecule adapted for receiving and expressing translatable first and second DNA sequences. That is, a DNA expression vector for expressing a heterodimeric antibody provides a system for independently cloning (inserting) the two translatable DNA sequences into two separate cassettes present in the vector, to form two separate cistrons for expressing the first and second polypeptides of a heterodimeric antibody. The DNA expression vector for expressing two cistrons is referred to as a dicistronic expression vector.

Preferably, the vector comprises a first cassette that includes upstream and downstream DNA regulatory sequences operably joined via a sequence of nucleotides adapted for directional ligation to an insert DNA. The upstream translatable sequence preferably encodes the secretion signal as described above. The cassette includes DNA regulatory sequences for expressing the first antibody polypeptide that is produced when an insert translatable DNA sequence is directionally inserted into the cassette via the sequence of nucleotides adapted for directional ligation.

The dicistronic expression vector also contains a second cassette for expressing the second antibody polypeptide. The second cassette includes a second translatable DNA sequence that preferably encodes a secretion signal, as described above, operably joined at its 3' terminus via a sequence of nucleotides adapted for directional ligation to a downstream DNA sequence of the vector that typically defines at least one stop codon in the reading frame of the cassette. The second translatable DNA sequence is operably joined at its 5' terminus to DNA regulatory sequences forming the 5' elements. The second cassette is capable, upon insertion of a translatable DNA sequence (insert DNA), of expressing the second fusion polypeptide comprising a secretion signal with a polypeptide coded by the insert DNA.

The peptides of the present invention may also be produced by eukaryotic cells such as CHO cells, human hybridomas, immortalized B-lymphoblastoid cells, and the like. In this case, a vector is constructed in which eukaryotic regulatory sequences are operably joined to the nucleotide sequences encoding the peptide. The design and selection of an appropriate eukaryotic vector is within the ability and discretion of one of ordinary skill in the art. The subsequent purification of the peptides may be accomplished by any of a variety of standard means known in the art.

In another embodiment, the present invention provides host cells, both prokaryotic and eukaryotic, transformed or transfected with, and therefore including, the vectors of the present invention.

Suitable host cells for the expression of glycosylated anti-ABCB5 antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

Vertebrate cells are also of particular interest as host cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/−DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for anti-ABCB5 antibody production and cultured in conventional nutrient media modified as appropriate for inducing promoters, selecting transformants, or amplifying the genes encoding the desired sequences.

The host cells used to produce the anti-ABCB5 antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re.

30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. The antibody composition prepared from the cells can be purified using, for example, hydroxylapatite chromatography, gel electrophoresis, dialysis, and affinity chromatography, with affinity chromatography being the preferred purification technique. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Following any preliminary purification steps, the mixture may be subjected to low pH hydrophobic interaction chromatography using an elution buffer at a pH between about 2.5-4.5, preferably performed at low salt concentrations (e.g., from about 0-0.25M salt).

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences, as desired.

The compositions and methods of the invention can be enhanced by utilization in combination with other procedures for cancer and precancerous lesions. In some instances the treatment procedure involves administration of another therapeutic agent such as an anti-cancer agent, including but not limited to chemotherapeutic agents and radiation. Chemotherapeutic agents may be selected from the group consisting of methotrexate, vincristine, adriamycin, cisplatin, taxol, paclitaxel, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, dacarbazine, LY294002, PX866, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT(Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2' deoxycoformycin), Semustine (methyl-CCNU), Teniposide (VM-26) and Vindesine sulfate, but it is not so limited.

The methods of the invention may be performed with therapies for treating the cancer such as surgery and radiation. The methods of the invention may also be performed in combination with a therapeutic that is an isolated short RNA that directs the sequence-specific degradation of a cancer specific mRNA through a process known as RNA interference (RNAi). In some embodiments the cancer-specific mRNA is ABCB5. The process is known to occur in a wide variety of organisms, including embryos of mammals and other vertebrates. It has been demonstrated that dsRNA is processed to RNA segments 21-23 nucleotides (nt) in length, and furthermore, that they mediate RNA interference in the absence of longer dsRNA. Thus, these 21-23 nt fragments are sequence-specific mediators of RNA degradation and are referred to herein as siRNA or RNAi. Methods of the invention encompass the use of these fragments (or recombinantly produced or chemically synthesized oligonucleotides of the same or similar nature) to enable the targeting of cancer specific mRNAs for degradation in mammalian cells useful in the therapeutic applications discussed herein.

The methods for design of the RNA's that mediate RNAi and the methods for transfection of the RNAs into cells and animals is well known in the art and the RNAi molecules are readily commercially available (Verma N. K. et al, J. Clin. Pharm. Ther., 28(5):395-404 (2004), Mello C. C. et al. Nature, 431(7006)338-42 (2004), Dykxhoom D. M. et al., Nat. Rev. Mol. Cell. Biol. 4(6):457-67 (2003) Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK)). The RNAs are preferably chemically synthesized using appropriately protected ribonucleoside phosphoramidites and a conventional DNA/RNA synthesizer. Most conveniently, siRNAs are obtained from commercial RNA oligo synthesis suppliers listed herein. In general, RNAs are not too difficult to synthesize and are readily provided in a quality suitable for RNAi. A typical 0.2 µmmol-scale RNA synthesis provides about 1 milligram of RNA, which is sufficient for 1000 transfection experiments using a 24-well tissue culture plate format.

The cancer specific cDNA specific siRNA is designed preferably by selecting a sequence that is not within 50-100 bp of the start codon and the termination codon, avoids intron regions, avoids stretches of 4 or more bases such as AAAA, CCCC, avoids regions with GC content<30% or >60%, avoids repeats and low complex sequence, and it avoids single nucleotide polymorphism sites. The target sequence may have a GC content of around 50%. The siRNA targeted sequence may be further evaluated using a BLAST homology search to avoid off target effects on other genes or sequences. Negative controls are designed by scrambling targeted siRNA sequences. The control RNA preferably has the same length and nucleotide composition as the siRNA but has at least 4-5 bases mismatched to the siRNA. The RNA molecules of the present invention can comprise a 3' hydroxyl group. The RNA molecules can be single-stranded or double stranded; such molecules can be blunt ended or comprise overhanging ends (e.g., 5', 3') from about 1 to about 6 nucleotides in length (e.g., pyrimidine nucleotides, purine nucleotides). In order to further enhance the stability of the RNA of the present invention, the 3' overhangs can be stabilized against degradation. The RNA can be stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

The RNA molecules used in the methods of the present invention can be obtained using a number of techniques known to those of skill in the art. For example, the RNA can be chemically synthesized or recombinantly produced using methods known in the art. Such methods are described in U.S. Published Patent Application Nos. US2002-0086356A1 and US2003-0206884A1 that are hereby incorporated by reference in their entirety.

The methods described herein are used to identify or obtain RNA molecules that are useful as sequence-specific mediators of cancer specific mRNA degradation and, thus, for inhibiting proteins which contribute to the functioning of cancer cells. Expression of ABCB5, for example, can be inhibited in humans in order to prevent the protein from being translated and thus preventing its function in vivo.

Any RNA can be used in the methods of the present invention, provided that it has sufficient homology to the cancer specific gene to mediate RNAi. The RNA for use in the present invention can correspond to the entire cancer specific gene or a portion thereof. There is no upper limit on the length of the RNA that can be used. For example, the RNA can range from about 21 base pairs (bp) of the gene to the full length of the gene or more. In one embodiment, the RNA used in the methods of the present invention is about 1000 bp in length. In another embodiment, the RNA is about 500 bp in length. In yet another embodiment, the RNA is about 22 bp in length. In certain embodiments the preferred length of the RNA of the invention is 21 to 23 nucleotides. The Sequence of ABCB5 is known, for instance, see U.S. Pat. No. 6,846,883 (which refers to ABCB5 as 7p P-glycoprotein).

The ABCB5 binding molecules of the invention are administered to the subject in an effective amount for treating cancer. An "effective amount for treating cancer" is an amount necessary or sufficient to realize a desired biologic effect. For example, an effective amount of a compound of the invention could be that amount necessary to c (i) kill a cancer cell; (ii) inhibit the further growth of the cancer, i.e., arresting or slowing its development; and/or (iii) sensitize a cancer cell to an anti-cancer agent or therapeutic. According to some aspects of the invention, an effective amount is that amount of a compound of the invention alone or in combination with a cancer medicament, which when combined or co-administered or administered alone, results in a therapeutic response to the cancer, either in the prevention or the treatment of the cancer. The biological effect may be the amelioration and or absolute elimination of symptoms resulting from the cancer. In another embodiment, the biological effect is the complete abrogation of the cancer, as evidenced for example, by the absence of a tumor or a biopsy or blood smear which is free of cancer cells.

The effective amount of a compound of the invention in the treatment of a cancer to or in the reduction of the risk of developing a cancer may vary depending upon the specific compound used, the mode of delivery of the compound, and whether it is used alone or in combination. The effective amount for any particular application can also vary depending on such factors as the cancer being treated, the particular compound being administered, the size of the subject, or the severity of the disease or condition. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject.

Subject doses of the compounds described herein typically range from about 0.1 to 10,000 mg, more typically from about 1 μg/day to 8000 mg, and most typically from about 10 μg to 100 μg. Stated in terms of subject body weight, typical dosages range from about 0.1 μg to 20 mg/kg/day, more typically from about 1 to 10 mg/kg/day, and most typically from about 1 to 5 mg/kg/day. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the molecules of the invention are also contemplated. In some instances, when the molecules of the invention are administered with a cancer medicament a sub-therapeutic dosage of either the molecules or the cancer medicament, or a sub-therapeutic dosage of both, is used in the treatment of a subject having, or at risk of developing, cancer. When the two classes of drugs are used together, the cancer medicament may be administered in a sub-therapeutic dose to produce a desirable therapeutic result. A "sub-therapeutic dose" as used herein refers to a dosage which is less than that dosage which would produce a therapeutic result in the subject if administered in the absence of the other agent. Thus, the sub-therapeutic dose of a cancer medicament is one which would not produce the desired therapeutic result in the subject in the absence of the administration of the molecules of the invention. Therapeutic doses of cancer medicaments are well known in the field of medicine for the treatment of cancer. These dosages have been extensively described in references such as Remington's Pharmaceutical Sciences, 18th ed., 1990; as well as many other medical references relied upon by the medical profession as guidance for the treatment of cancer. Therapeutic dosages of antibodies have also been described in the art.

A variety of administration routes are available. The particular mode selected will depend, of course, upon the particular anti-ABCB5 antibody selected, the particular condition being treated and the dosage required for therapeutic efficacy. The methods of this invention, generally speaking, may be practiced using any mode of administration that is medically acceptable, meaning any mode that produces effective levels of protection without causing clinically unacceptable adverse effects. Preferred modes of administration are parenteral routes. The term "parenteral" includes subcutaneous, intravenous, intramuscular, intraperitoneal, and intrasternal injection, or infusion techniques. Other routes include but are not limited to oral, nasal, dermal, sublingual, and local.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The compounds of the invention can be administered by any ordinary route for administering medications. Depending upon the type of cancer to be treated, compounds of the invention may be inhaled, ingested or administered by systemic routes. Systemic routes include oral and parenteral. Inhaled medications are preferred in some embodiments because of the direct delivery to the lung, particularly in lung cancer patients. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. Preferred routes of administration include but are not limited to oral, parenteral, intramuscular, intranasal, intratracheal, intrathecal, intravenous, inhalation, ocular, vaginal, and rectal. For use in therapy, an effective amount of the compounds of the invention can be administered to a subject by any mode that delivers the nucleic acid to the affected organ or tissue. "Administering" the pharmaceutical composition of the present invention may be accomplished by any means known to the skilled artisan.

According to the methods of the invention, the peptide may be administered in a pharmaceutical composition. In general, a pharmaceutical composition comprises the peptide of the invention and a pharmaceutically-acceptable carrier. Pharmaceutically-acceptable carriers for peptides, monoclonal antibodies, and antibody fragments are well-known to those of ordinary skill in the art. As used herein, a pharmaceutically-acceptable carrier means a non-toxic material that does not interfere with the effectiveness of the biological activity of the active ingredients, e.g., the ability of the peptide to bind to ABCB5.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The peptides of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

When the compounds described herein (including peptide and non-peptide varieties) are used therapeutically, in certain embodiments a desirable route of administration may be by pulmonary aerosol. Techniques for preparing aerosol delivery systems containing compounds are well known to those of skill in the art. Generally, such systems should utilize components which will not significantly impair the biological properties of the peptides (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The peptides of the invention may be administered directly to a tissue. Preferably, the tissue is one in which the cancer stem cells are found. Alternatively, the tissue is one in which the cancer is likely to arise. Direct tissue administration may be achieved by direct injection. The peptides may be administered once, or alternatively they may be administered in a plurality of administrations. If administered multiple times, the peptides may be administered via different routes. For example, the first (or the first few) administrations may be made directly into the affected tissue while later administrations may be systemic.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium to alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In yet other embodiments, the preferred vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix disclosed in PCT/US/03307. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the peptide, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for prophylactic treatment of subjects at risk of developing a recurrent cancer. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Therapeutic formulations of the antibodies may be prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Melanoma Cells and Culture Methods.

The G3361 human malignant melanoma cell line, derived from a single tumor cell cloned in soft agar, was provided by Dr. Emil Frei III (Dana-Farber Cancer Institute, Boston, Mass.), the A375 cell line is commercially available from American Type Culture Collection (ATCC) (Manassas, Va.). All cell lines were cultured in RPMI 1640 medium supplemented with 10% fetal bovine serum, 6 mmol/L HEPES, 2 mmol/l L-glutamine, and 100 IU/ml penicillin/streptomycin at 37° C. and 5% $CO_2$ in a humidified incubator as previously described. The G3361/DsRed2 and G3361/EYFP cell lines were generated by stable transfection of G3361 melanoma cells with either *Discosoma* sp. red fluorescent protein (DsRed2) or the enhanced yellow-green variant (EYFP) of the *Aequorea victoria* green fluorescent protein (GFP) in conjunction with the simian virus 40 large T-antigen nuclear retention signal (Kalderon, D., Roberts, B. L., Richardson, W. D. & Smith, A. E. A short amino acid sequence able to specify nuclear location. Cell 39, 499-509 (1984)), using pDsRed2-Nuc or pEYFP-Nuc mammalian expression vectors also containing a neomycin resistance cassette (BD Biosciences, Palo Alto, Calif.) and the Lipofectamine 2000 reagent (Invitrogen) as previously described. Clonal G3361/DsRed and G3361/EYFP cultures were generated from stably transfected cultures by limiting dilution. Clinical melanoma cells (n=6 patients) were freshly derived from surgical specimen according to human subjects research protocols approved by the IRBs of the University of Würzburg Medical School or the Wistar Institute, Philadelphia, Pa.

Antibodies.

The specific IgG1κ anti-ABCB5 mAb 3C2-1D12 was used herein in the expression studies. FITC-conjugated 3C2-1D12 mAb was used to assay purity of sorted ABCB5$^+$ and ABCB5$^-$ melanoma subsets. Unconjugated or FITC-conjugated MOPC-31C mouse isotype control mAbs, FITC-conjugated goat anti-mouse IgG secondary Ab, phycoerythrin (PE)-conjugated anti-human CD20, anti-human CD31 and isotype control mAbs were purchased from PharMingen, San Diego, Calif. Allophycocyanin (APC)-conjugated and PE-conjugated secondary mAbs were purchased from eBioscience, San Diego, Calif. Unconjugated anti-human TIE-1, anti-human BMPR1a, PE-conjugated anti-human VE-cadherin and anti-human Nestin mAbs were from R&D Systems, Minneapolis, Minn. The following antibodies were used for ABCB5, TIE-1 and VE-cadherin immunohistochemistry and immunofluorescence staining: mouse anti-ABCB5 mAb (Frank, N. Y. et al. ABCB5-mediated doxorubicin transport and chemoresistance in human malignant melanoma. Cancer Res 65, 4320-33 (2005); Frank, N. Y. et al. Regulation of progenitor cell fusion by ABCB5 P-glycoprotein, a novel human ATP-binding cassette transporter. J Biol Chem 278, 47156-65 (2003)), HRP-conjugated horse anti-mouse IgG secondary Ab (Vector Laboratories, Burlingame, Calif.), FITC-conjugated rabbit anti-mouse IgG secondary Ab (ZYMED Laboratories, San Francisco, Calif.), unconjugated rabbit anti-human VE-cadherin Ab (kindly provided by Cell Signaling Technology, Danvers, Mass.), mouse control IgG Abs (DAKO, Carpinteria, Calif.), unconjugated rabbit anti human TIE-1 mAb (Santa Cruz Biotechnologies, Santa Cruz, Calif.), FITC-conjugated donkey anti-mouse IgG secondary Ab, Texas Red-conjugated donkey anti-rabbit IgG secondary Ab, Cy3-conjugated donkey anti-rabbit IgG secondary Ab, and rabbit control IgG Ab (all from Jackson ImmunoResearch, West Grove, Pa.).

Histopathology and Immunohistochemistry.

5 micron-thick melanoma cryosections were fixed in −20° C. acetone for 5 minutes. Air-dried sections were incubated with 10 μg/ml ABCB5 mAb at 4° C. overnight; 10 μg/ml mouse IgG were used as negative control. Sections were washed with PBS×3 for 5 minutes and incubated with 1:200 peroxidase-conjugated horse anti-mouse IgG Ab for ABCB5 staining. For ABCB5/VE-cadherin or ABCB5/TIE-1 fluorescence double labeling, 5 μm melanoma sections were fixed in −20° C. acetone for 5 minutes. Air-dried sections were incubated with 10 μg/ml ABCB5 mAb and 2.5 μg/ml VE-cadherin or TIE-1 Abs at 4° C. overnight; 10 μg/ml mouse IgG and 2.5 μg/ml rabbit IgG were used as negative controls. Sections were washed with PBS containing 0.05% tween 20 for 5 minutes×3 and incubated with a 1:150 dilution of Texas Red-conjugated or Cy3-conjugated donkey anti-rabbit IgG Ab and FITC-conjugated rabbit anti-mouse IgG Ab for 30 minutes at room temperature. After subsequent washings, the sections were mounted with VECTASHIELD mounting medium (Vector Laboratories) and covered by coverslip. Immunofluorescence reactivity was viewed on an Olympus BX51/52 system microscope coupled to a Cytovision system (Applied Imaging, San Jose, Calif.).

Tissue Microarray Design and Analysis.

The Melanocytic Tumor Progression TMA is the product of a joint effort of the three Skin SPORES (Harvard, M.D. Anderson, University of Pennsylvania). This array contains 480×0.6 mm cores of tumor tissue representing four major diagnostic tumor types: benign nevi, primary cutaneous melanoma, lymph node metastasis and visceral metastasis. Cases were collected from the Pathology services of the three participating institutions. For quality control purposes, two duplicate cores are chosen at each distinct region. Nevi and primary melanomas had either one region or three regions of the tissue block sampled (2 or 6 cores), whereas metastatic tumors had one region sampled from each block. Therefore, the 480 cores represent 2 adjacent cores from 240 distinct histological regions. This array includes 130 cores from 35 nevi, 200 cores from 60 primary melanoma and 150 cores from 75 metastatic lesions. Operationally, thin nevi and thin melanomas involved only the superficial/papillary dermis, whereas thick nevi and thick melanomas had grown to involve both papillary and deep (reticular) dermis. This array was constructed in the laboratory of Dr. Mark Rubin (Brigham and Women's Hospital Department of Pathology and Dana Farber Cancer Institute, Boston). Histologic sections of the tissue array slide were baked at 58° C. for 20 minutes and then treated as follows: xylene×2 (1 hour, 10 minutes), 100% ethanol×2 for 2 minutes, 95% ethanol for 2 minutes, and dH$_2$O×3 for 2 minutes. Antigen retrieval was performed in 10 mMol citrate buffer, pH 6.0 with boiling in pressure cooker for 10 minutes and then cooled to room temperature. After washing with PBS×2 for 5 minutes, tissue was blocked with 10% horse serum and 1% BSA in PBS at room temperature for 1 hour then incubated with 5 µg/ml ABCB5 mAb at 4° C. overnight. The tissue was then washed with PBS-0.05% tween 20×3 for 5 minutes then treated with 3% $H_2O_2$/PBS for 15 minutes. After rinsing in PBS, the sections were incubated with 1:200 biotinylated horse anti-mouse IgG Ab at room temperature for 30 minutes, rinsed in PBS-tween×3 for 5 minutes, and incubated with avidin-biotin-horseradish peroxidase complex (Vector Laboratories) for 30 minutes at room temperature. Immunoreactivity was detected using NovaRed substrate (Vector Laboratories). The Chromavision Automated Cellular Imaging System (ACIS) was used to quantify the immunostaining intensity of ABCB5 and mIgGIR on the HTMA 84 tissue microarray. The control slide intensity values (background plus intrinsic melanization) were subtracted from the experimental slide and the difference in the intensity values for each core was taken to be the true staining. This graph (see FIG. 1) shows with 95% confidence interval the difference in intensity for each pathology diagnosis. P values between relevant groups were calculated using the independent/samples t test. The number above each error bar shows the number of cases within each group.

Flow Cytometric Analysis of ABCB5 Expression.

Analysis of coexpression of ABCB5 with the CD20, CD31, VE-cadherin, or BMPR1a surface markers or the Nestin or TIE-1 intracellular markers in clinical patient-derived melanoma cell suspensions was performed by dual-color flow cytometry as described previously. Clinical melanoma cells were incubated with anti-ABCB5 mAb or isotype control mAb or no Ab followed by counterstaining with APC-conjugated donkey anti-mouse IgG. Cells were then fixed in PBS containing 2% Paraformaldehyde (30 min at 4° C.), and subsequently incubated with PE-conjugated anti-CD20, anti-CD31, anti-VE-cadherin, anti-Nestin or PE-conjugated isotype control mAbs, or unconjugated anti-BMPR1a, anti-TIE-1 or unconjugated isotype control mAbs followed by counterstaining with PE- or FITC-conjugated anti-immunoglobulin secondary antibodies. Washing steps with staining buffer or 1% saponin permeabilization buffer were performed between each step. Dual-color flow cytometry was subsequently done with acquisition of fluorescence emission at the Fl1 (FITC) or Fl2 (PE) and Fl4 (APC) spectra on a Becton Dickinson FACScan (Becton Dickinson, San Jose, Calif.) as described. Statistical differences in expression levels of the above listed markers by ABCB5+ and ABCB5− cells were determined using the nonparametric Mann-Whitney test. A two-sided P value of P<0.05 was considered significant. A375 melanoma cells were analyzed for surface ABCB5 expression by incubation with anti-ABCB5 mAb or isotype control mAb (10 µg/ml) followed by counterstaining with FITC-conjugated goat anti-mouse immunoglobulin secondary antibody and single-color flow cytometry (Fl1) as described.

Cell Isolation.

Single cell suspensions were generated from human melanoma xenografts upon surgical dissection of tumors from sacrificed Balb/c NOD/SCID or Balb/c nude mice 8 weeks following tumor cell inoculation. Each tumor was cut into small pieces (ca. 1 mm$^3$) and tumor fragments were subsequently incubated in 10 ml sterile PBS containing 0.1 g/L calcium chloride and 5 mg/ml Collagenase Serva NB6 (SERVA Electrophoresis GmbH, Heidelberg, Germany) for 3 hours at 37° C. on a shaking platform at 200 rpm to generate single cell suspensions. Subsequently, tumor cells were washed with PBS for excess collagenase removal. ABCB5+ cells were isolated by positive selection and ABCB5− cell populations were generated by removing ABCB5+ cells using anti-ABCB5 mAb labeling and magnetic bead cell sorting as described. Briefly, human G3361 or A375 melanoma cells or single cell suspensions derived from human melanoma xenografts or clinical melanoma samples were labeled with anti-ABCB5 mAb (20 µg/ml) for 30 min at 4° C., washed for excess antibody removal, followed by incubation with secondary anti-mouse IgG mAb-coated magnetic microbeads (Miltenyi Biotec, Auburn, Calif.) and subsequent dual-passage cell separation in MiniMACS separation columns (Miltenyi Biotec) according to the manufacturers recommendations. Purity of ABCB5+ cell isolates and ABCB5− human G3361 melanoma cells was assayed by flow cytometric analysis of ABCB5-expression (Fl1) on a FACSCalibur machine (Becton Dickinson, Sunnyvale, Calif.) after incubation with FITC-conjugated anti-ABCB5 mAb, followed by anti-mouse IgG mAb-coated microbead incubation and magnetic cell sorting. Statistical differences in ABCB5-expression between unsegregated, ABCB5+, and ABCB5− human G3361 melanoma cells were determined using one-way ANOVA followed by the Bonferroni correction. A two-sided P value of P<0.05 was considered statistically significant.

Animals.

Balb/c nude mice and Balb/c NOD/SCID mice were purchased from The Jackson Laboratory (Bar Harbor, Me.). Mice were maintained in accordance with the institutional guidelines of Children's Hospital Boston and Harvard Medical School and experiments were performed according to approved experimental protocols.

Human Melanoma Xenotransplantation.

Unsegregated, ABCB5+, or ABCB5− human G3361 ($10^7$, $10^6$, or $10^5$/inoculum, respectively), or human A375 ($2\times10^6$, $2\times10^5$, or $2\times10^4$/inoculum, respectively), or clinical patient-derived melanoma cells ($10^6$/inoculum, respectively), or ABCB5+ or ABCB5− cells isolated from ABCB5+-derived primary G3361 tumor xenografts ($10^7$/inoculum, respectively) were injected s.c. uni- or bilaterally into the flanks of recipient Balb/c NOD/SCID mice. Tumor formation/growth was assayed weekly as a time course, at least up to the endpoint of 8 weeks, unless excessive tumor size required protocol-stipulated euthanasia earlier, by determination of tumor volume (TV) according to the established formula [TV (mm$^3$)=$\pi$/6×0.5×length×(width)$^2$]. With respect to tumor formation, mice were considered tumor-negative if no tumor tissue was identified upon necropsy. Statistically significant differences in primary and secondary tumor formation were assessed using the Fisher's Exact test. Differences in tumor volumes were determined using one-way ANOVA followed by the Bonferroni correction or the Kruskal-Wallis Test followed by Dun's correction, with two-tailed P values<0.05 considered significant.

In Vivo Genetic Lineage Tracking.

ABCB5+/DsRed2 and ABCB57EYFP human G3361 tumor cell populations, generated using magnetic bead cell sorting as above, were reconstituted at relative abundance ratios of $1\times10^6$ and $9\times10^6$ cells, respectively, followed by determination of resultant cell ratios in inocula by dual-color flow cytometry (Fl1 (EYFP) vs. Fl2 (DsRed2) plots) prior to xenotransplantation. G3361/DsRed2 and G3361/EYFP co-cultures were injected s.c. ($10^7$ cells/inoculum) into the right flank of recipient Balb/c NOD/SCID mice. At 4 or 6 weeks post xenotransplantation, tumors were harvested and single cell suspensions or frozen tissue sections prepared as above, for determination of relative in vivo abundance of DsRed2+ and EYFP+ melanoma cells by dual-color flow cytometry or fluorescence microscopy of tumor-derived single cell suspensions (upon attachment in adherent tissue culture plates), and for analysis of 5 μm frozen tissue sections by fluorescence microscopy. In additional experiments, the relative abundance of DsRed2+ and EYFP+ melanoma cells was determined in ABCB5+ or ABCB5 xenograft-derived cell subsets by dual-color flow cytometry as above and the percentages of DsRed2+ and EYFP+ tumor cells were statistically compared using the unpaired student t test, with a two-sided P value of P<0.05 considered statistically significant.

Anti-ABCB5 mAb Targeting.

Unsegregated human G3361 melanoma cells were xenografted s.c. into recipient Balb/c nude mice ($10^7$/inoculum). Animals were injected i.p. with anti-ABCB5 mAb (clone 3C2-1D12), isotype control mAb (500 μg/injection) bi-weekly or no Ab starting 24 hrs prior to melanoma xenotransplantation. Tumor growth was assayed bi-weekly as a time course by determination of tumor volume (TV) as described above. Differences in tumor volumes were determined using nonparametric one-way ANOVA (Kruskal-Wallis Test) followed by Dun's correction for comparison of the three experimental groups, with two-tailed P values<0.05 considered significant. For determination of binding efficacy of in vivo administered anti-ABCB5 mAb to established human to nude mouse melanoma xenografts, single cell suspensions and frozen sections were generated from melanoma xenografts 24 hours following i.p. administration of anti-ABCB5 mAb, murine IgG1κ isotype control mAb, or no treatment. The prepared single cell suspensions were subsequently incubated with FITC-conjugated goat anti-mouse Ig secondary Ab for 30 min at 4° C. and analyzed by single color flow cytometry as above, and frozen sections were incubated with HRP-conjugated horse anti-mouse Ig secondary Ab and analyzed as above.

Assessment of ADCC and CDC.

ADCC or CDC were determined by dual-color flow cytometry as described previously. Briefly, human G3361 melanoma cell suspensions in serum-free Dulbecco's Modified Eagle's Medium (DMEM) (BioWhittaker, Walkersville, Md.) were labeled with 3,3'-dioctadecyloxacarbocyanine (DiO) (Invitrogen, Carlsbad, Calif.) according to the manufacturers recommendations. DiO-labeled melanoma cells were then plated at a density of 300,000 cells per well in flat-bottomed 6-well culture plates in 3 ml and cultured in standard medium in a humidified incubator overnight. Thereafter, DiO-labeled melanoma target cells were pre-incubated in the presence or absence of anti-ABCB5 or isotype control mAbs (20 μg/ml, respectively) for 30 min at 37° C., 5% $CO_2$, and subsequently cocultured for additional 24 hours at 37° C., 5% $CO_2$ with or without freshly isolated Balb/c nude mouse effector splenocytes ($12 \times 10^6$ cells/well, 1:40 target to effector cell ratio) for assessment of ADCC, or in the presence or absence of 5% Balb/c nude mouse serum for determination of CDC. Subsequently cells and their supernatants were harvested and analyzed by dual-color flow cytometry on a FACSCalibur machine (Becton Dickinson) immediately upon addition of 10 μg/ml propidium iodide (PI) (Sigma, Milwaukee, WN), with lysed target cells recognized by a DiO+PI+ phenotype. ADCC levels for the three treatment groups were calculated as follows: [ADCC (%)=(DiO+PI+ percent sample positivity)−(mean Ab-untreated DiO+PI+ percent sample positivity)]. Differences in ADCC levels were determined using nonparametric one-way ANOVA (Kruskal-Wallis Test) followed by Dun's correction, with two-tailed P values<0.05 considered significant.

Cell Viability Measurements.

Cell viability was measured in tumor cell inocula prior to xenotransplantation using calcein-AM staining. Briefly, $1 \times 10^6$ unsegregated, ABCB5+, or ABCB5− melanoma cells were incubated with calcein-AM (Molecular Probes, Eugene, Oreg.) for 30 min at 37° C. and 5% $CO_2$ to allow for substrate-uptake and enzymatic activation to the fluorescent derivative. Subsequently the cells were washed and fluorescence measurements acquired by flow cytometry at the Fl2 emission spectrum on a Becton Dickinson FACScan. Cells exhibiting generation of the fluorescent calcein-AM derivative compared to unexposed samples were considered viable. Cell viability was also determined in all samples using the trypan blue dye exclusion method.

RNA Extraction and Real-Time Quantitative Reverse Transcription-PCR.

RNA extraction from G3361 and A375 human melanoma cells and standard cDNA synthesis reactions were performed using the SuperScript First-Strand Synthesis System for reverse transcription-PCR (Invitrogen) as described previously. Total RNA prepared from 8 additional melanoma cell lines of the NCI-60 panel (LOX IMVI, SK-MEL-5, M14, UACC-62, SK-MEL-28, UACC-257, SK-MEL-2, MALME-3M) maintained at the National Cancer Institute under conditions and with passage numbers as described previously was provided by the NCI/NIH Developmental Therapeutics Program. Real-time quantitative reverse transcription-PCR for relative ABCB5 gene expression was performed as described previously. ABCB5 expression was assessed by the ratio of the expression level in the sample against mean expression in all samples, in n=3 independent experiments. Growth data (culture doubling time) for the 8 human melanoma cell lines from the NCI-60 panel were those obtained by the National Cancer Institute, which can be found online (http://dtp.nci.nih.gov/docs/misc/common_files/cell_list.html). Growth kinetics for the G3361 and A375 melanoma cell lines were established in our laboratory by cell counting according to the formula: to population doubling time (h)=T2−T1/($\log_2$(cell count$_{T2}$/cell count$_{T1}$)), where T2 and T1 represent two distinct time points (h) in the logarithmic culture growth phase. Linear correlation of relative ABCB5 mRNA expression and culture doubling times (h) was performed and a Pearson correlation coefficient was calculated and the criteria of P<0.05 and r>0.3 or r<−0.3 were used to identify significant correlations as described previously.

Example 1

We first examined the relationship of ABCB5 to clinical malignant melanoma progression, because of its close association with CD166, a marker of more advanced disease. This was assessed via ABCB5 immunohistochemical staining and quantitative image analysis of an established melanoma progression tissue microarray (TMA) containing 480 patient-derived melanoma tissue cores (0.6 mm), representing four major diagnostic tumor types: benign melanocytic nevi, primary cutaneous melanoma, melanoma metastases to lymph nodes, and melanoma metastases to viscera (FIG. 1a). We found that primary or metastatic melanomas expressed significantly more ABCB5 than benign melanocytic nevi (P<0.001), thick primary melanomas expressed more ABCB5 than thin primary melanomas (P=0.004), and melanomas metastatic to lymph nodes expressed more ABCB5 than primary lesions (P=0.001), identifying ABCB5 as a novel molecular marker of neoplastic progression in human malignant melanoma. Apparent heterogeneity in ABCB5 expression was noted in metastases, with greater staining in lymph node than visceral metastases (P=0.025).

Example 2

Figure 1B:
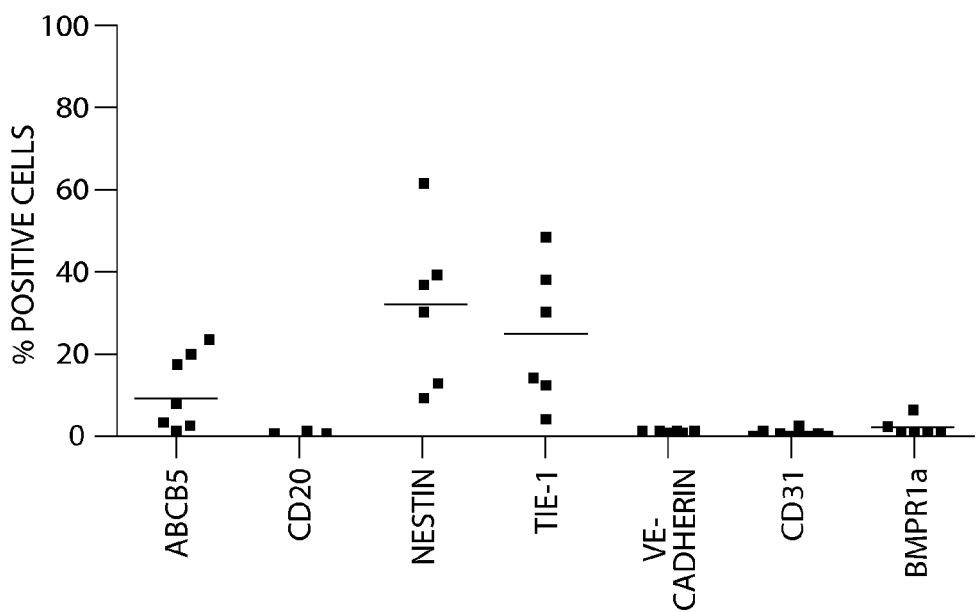
FIG. 1(b) depicts a single-color flow cytometry analysis of clinical melanoma samples for expression of ABCB5, CD20, Nestin, TIE-1, VE-cadherin, CD31, or BMPR1a. Illustrated are % positive cells for n=6 melanoma patients (horizontal bars indicate mean expression).
Figure 1C:
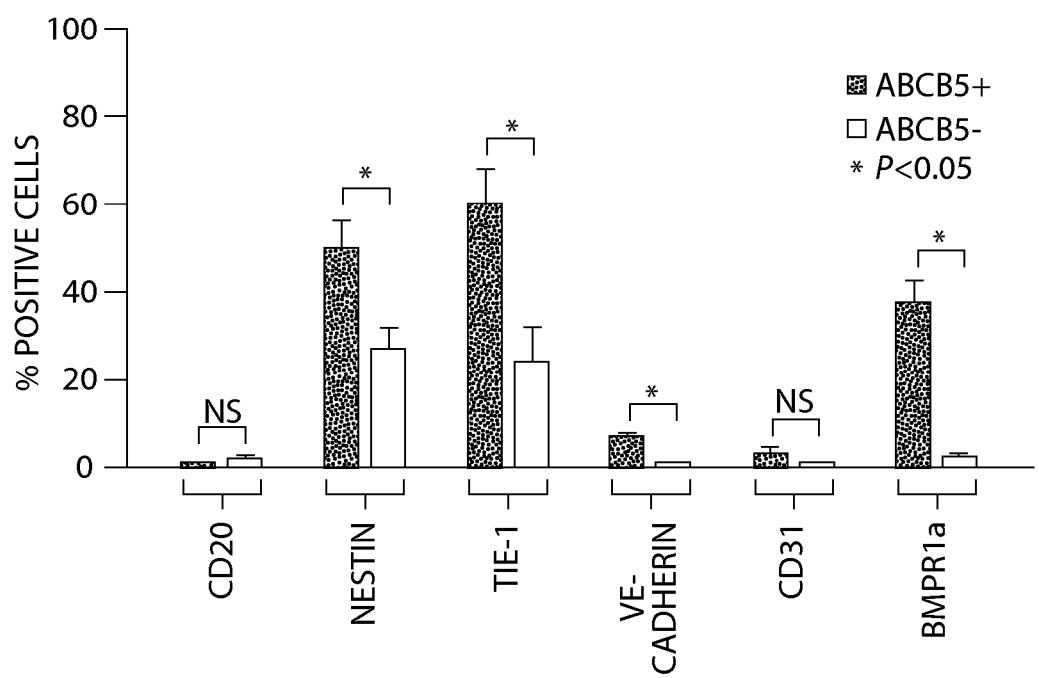
FIG. 1(c) shows the expression of CD20, Nestin, TIE-1, VE-cadherin, CD31, or BMPR1a by ABCB5+ or ABCB5− clinical melanoma cells as determined by dual-color flow cytometry. % positive cells (mean±SEM) are illustrated for n=3-6 melanoma patients.

When assayed by flow cytometry in single cell suspensions freshly derived from a smaller series of surgically dissected clinical melanomas (n=6 patients, Table 1), ABCB5 was also found to be consistently expressed in 6 of 6 specimen, with ABCB5$^+$ tumor cell frequency ranging from 1.6 to 20.4% (9.2±3.2%, mean±SEM) (FIG. 1b, Table 1). Further phenotypic characterization with respect to antigens associated with a more primitive molecular phenotype revealed significant expression of CD20 in 3 of 6 specimen (frequency in all samples: 0.3±0.2%, mean±SEM), nestin in 6 of 6 (31.9±7.8%), TIE-1 in 6 of 6 (24.9±6.9%), VE-cadherin in 4 of 6 (0.2±0.1%), BMPR1a in 6 of 6 (1.8±1.0%), and of the stromal marker CD31 in 5 of 6 specimen (0.8±0.4%) (FIG. 1b). Preferential expression by ABCB5$^+$ compared to ABCB5$^-$ subpopulations, as previously identified for the stem cell determinant CD133, was hereby demonstrated in those samples expressing the respective markers for nestin (49.4±6.6% vs. 26.6±4.9%, respectively, mean±SEM, P=0.026), TIE-1 (59.4±7.8% vs. 23.8±7.5%, P=0.015), VE-cadherin (6.4±1.2% vs. 0.1±0.1%, P=0.029), and BMPR1a (37.0±4.4 vs. 2.0±0.2%, P=0.002), but not for CD20 (0.2±0.2% vs. 1.1±0.7%, NS), or CD31 (2.4±1.2% vs. 0.5±0.3%, NS) (FIG. 1c). In situ immunohistochemistry revealed ABCB5$^+$ single cells or clusters to account for a minority subpopulation within clinical tumors with positively-stained cells predominantly correlating with non-melanized, undifferentiated regions or TIE-1 expression, and unreactive zones corresponding to melanized, more differentiated areas.

Table 1 summarizes the tumor characteristics of six patients with a melanoma site (either a metastasis or primary recurrent). Tumors are quantified by % of ABCB5+ present. Also shown is a summary of the outcomes (number of mice with tumors) for nine groups of NOD/SCID mice which were transplanted with replicate (n=2-10) inocula of unsegregated, ABCB5$^+$ or ABCB5$^-$ human melanoma cells.

TABLE 1

Patient and tumor characteristics

| Patient no | Melanoma site | ABCB5$^+$ in tumor (%) | Number of transplanted mice with tumors | | |
|---|---|---|---|---|---|
| | | | Un-segregated | ABCB5− | ABCB5+ |
| P1 | Metastasis | 8.5 | 0/2 | 0/2 | 2/2 |
| P2 | Metastasis | 1.6 | 1/2 | 0/2 | 2/2 |
| P3 | Metastasis | 3.2 | 5/5 | 1/5 | 5/5 |
| P4 | Metastasis | 20.4 | N/A | N/A | N/A |
| P5 | Metastasis | 17.4 | N/A | N/A | N/A |
| P6 | Primary | 4.2 | N/A | N/A | N/A |

Example 3

Figure 5A:
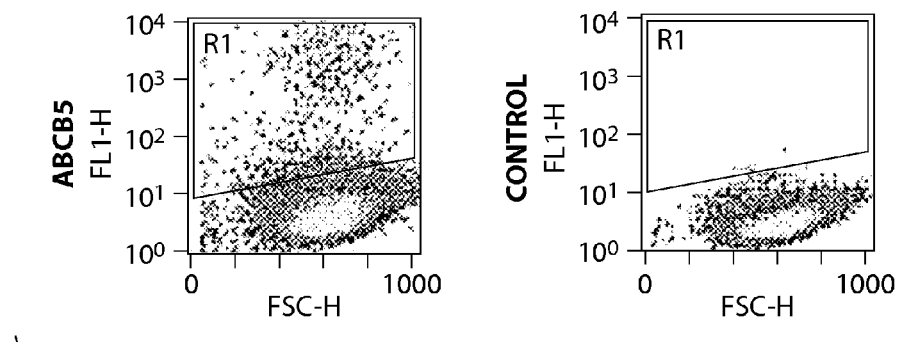
FIG. 5(a) depicts the representative flow cytometric surface ABCB5 expression or control staining (FITC, Fl1) plotted against forward scatter (FSC) determined in unsegregated cultures of human A375 melanoma cells.
Figure 5B:
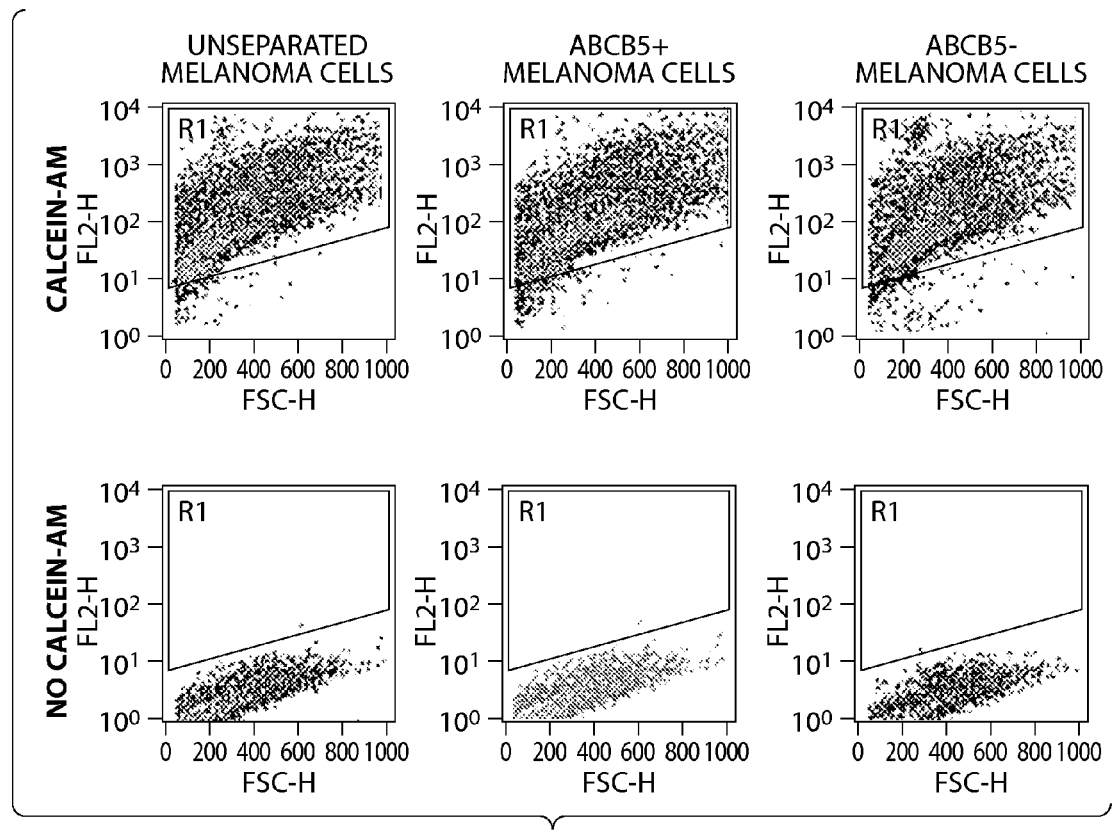
FIG. 5(b) depicts the representative single-color flow cytometric analysis of cell viability for unsegregated (left panels), ABCB5⁺ (center panels) and ABCB5⁻ (right panels) human melanoma cells as determined by cellular incorporation and enzymatic activation of the fluorescent dye calcein-AM. The upper panels depict calcein-AM samples, the lower panels no calcein-AM controls. Viable cells are found in the R1 gates of the FSC vs. Fl2 plots. Figure (c) is a graph showing the ABCB5 expression of unsegregated and purified ABCB5⁺ or ABCB5⁺-depleted (ABCB5) G3361 human melanoma cells.

To determine whether the melanoma cell subset defined by ABCB5 was enriched for MMIC, we compared the abilities of ABCB5$^+$-purified (ABCB5$^+$) vs. ABCB5$^+$-depleted (ABCB5$^-$) melanoma cells to initiate tumor formation in vivo, using either established clonal cutaneous human melanoma cultures (G3361: 2-10% ABCB5 positivity; A375: 1-10% positivity, FIG. 5a) or freshly patient-derived melanoma cells (FIG. 1b, Table 1) in human to NOD/SCID mouse tumor xenotransplantation experiments. Groups of NOD/SCID mice were transplanted with replicate (n=2-10) inocula of unsegregated, ABCB5$^+$ or ABCB5$^-$ human melanoma cells over a log-fold range from cell doses unable to efficiently initiate tumor growth (G3361: 10$^5$ cells, A375: 2×10$^4$ cells) to doses that consistently initiated tumor formation when ABCB5$^+$ cells were used (G3361: 10$^7$ cells, A375: 2×10$^6$ cells, fresh patient isolates: 10$^6$ cells). Cell viability determined by calcein-AM staining exceeded 90% in all tumor cell inocula and did not significantly differ among isolates (FIG. 5b).

Figure 2A:
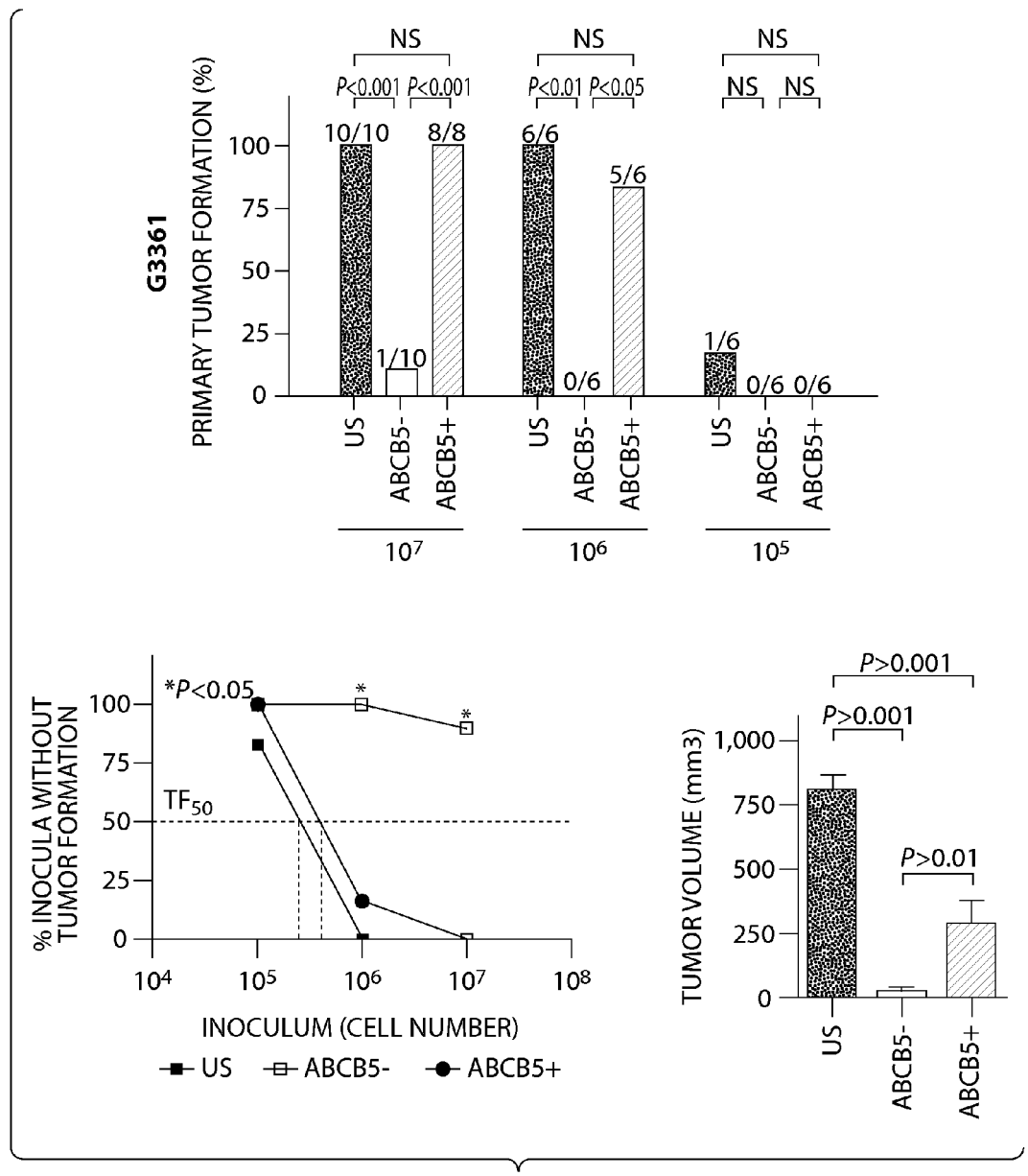
FIG. 2(a) (Left panel) is a graph demonstrating the in vivo tumor formation capacity (%) of unsegregated (US), ABCB5−, or ABCB5+ G3361 melanoma cells following s.c. xenotransplantation ($10^7$, $10^6$, or $10^5$ cells/inoculum) into NOD/SCID mice. (Center Panel) is a graph showing the % inocula without tumor formation plotted against inoculated cell numbers for unsegregated (US), ABCB5−, or ABCB5+ G3361 melanoma cells into NOD/SCID mice, for determination of the Tumor Formation Capacity 50% ($TF_{50}$). (Right panel) shows the tumor volumes (mean±SEM) of primary melanoma xenografts 8 weeks after s.c. xenotransplantation into NOD/SCID mice of unsegregated (US), ABCB5−, or ABCB5+ G3361 melanoma cells ($10^7$/inoculum).

Of 22 aggregate mice injected with ABCB5$^-$ G3361 melanoma cells only 1 mouse transplanted with the highest cell dose generated a tumor (FIG. 2a, left panel). In contrast, 13 of 20 injected with ABCB5$^+$ cells formed tumors (P<0.0001), including all mice injected with the highest cell dose (FIG. 2a, left panel, additional P values for individual dose-specific comparisons provided in figure), indicating >2 log-fold enrichment for MMIC in this cell subset, as determined by comparison of inocula doses required for 50% tumor formation (TF$_{50}$) (FIG. 2a, center panel).

Figure 2B:
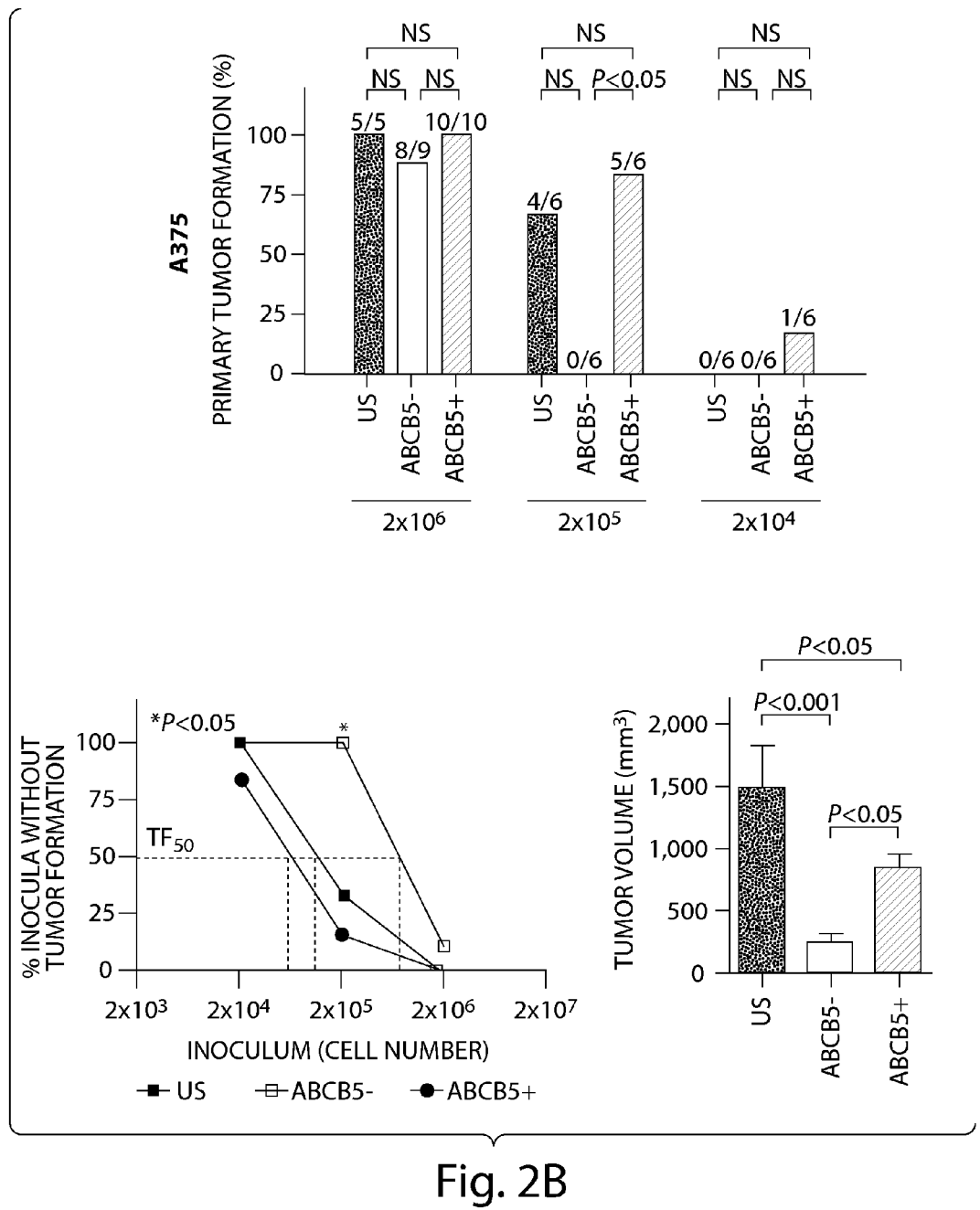
FIG. 2(b) (Left panel) is a graph showing the in vivo tumor formation capacity (%) of unsegregated (US), ABCB5−, or ABCB5+ A375 melanoma cells following s.c. xenotransplantation ($2\times10^6$, $2\times10^5$, or $2\times10^4$ cells/inoculum) into NOD/SCID mice. (Center Panel) depicts the % inocula without tumor formation plotted against inoculated cell numbers for unsegregated (US), ABCB5−, or ABCB5+ A375 melanoma cells into NOD/SCID mice, for determination of the Tumor Formation Capacity 50% ($TF_{50}$). (Right panel) shows the tumor volumes (mean±SEM) of primary melanoma xenografts 5 weeks after s.c. xenotransplantation into NOD/SCID mice of unsegregated (US), ABCB5−, or ABCB5+ A375 melanoma cells ($2\times10^6$/inoculum).
Figure 5C:
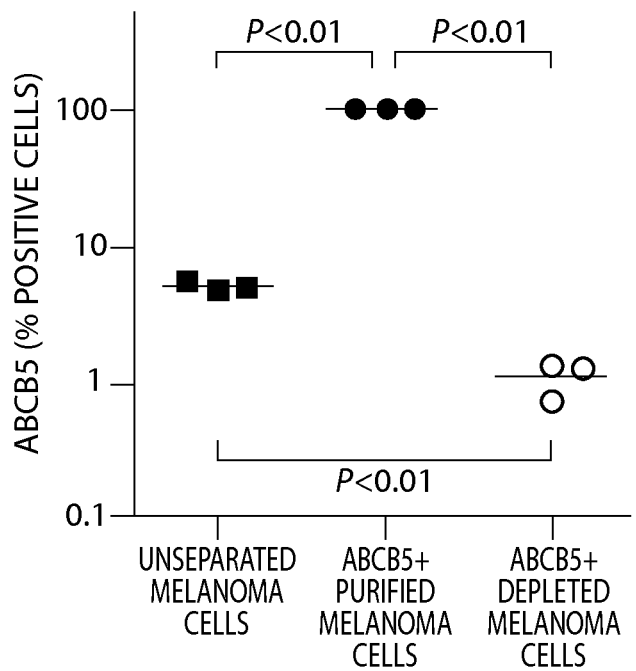
FIG. 5 summarizes the characterization of unsegregated, ABCB5⁺, or ABCB5⁻ human melanoma cells prior to xenotransplantation.
Figure 6:
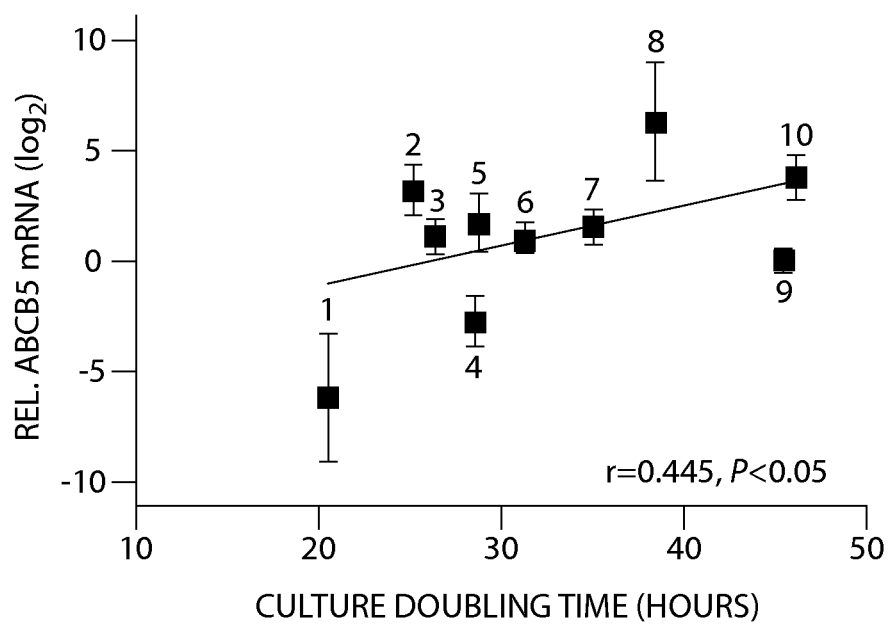
FIG. 6 is a graph summarizing the correlation analysis of relative ABCB5 gene expression with melanoma cell culture doubling times. Pearson correlation of relative ABCB5 gene expression determined by real-time RT-PCR (mean±SD, n=3 independent experiments) and culture doubling times of 10 melanoma cell lines (1, LOX IMVI; 2, SK-MEL-5; 3, M14; 4, A375; 5, G3361; 6, UACC-62; 7, SK-MEL-28; 8, UACC-257; 9, SK-MEL-2; 10, MALME-3M); r is the Pearson correlation coefficient.

Similarly, of 21 aggregate mice injected with ABCB5$^-$ A375 melanoma cells, only 8 mice developed a tumor, whereas 16 of 22 mice injected with ABCB5$^+$ cells formed tumors (P<0.05), indicating >1 log-fold enrichment for MMIC among ABCB5$^+$ A375 cells (FIG. 2b, left and center panels). ABCB5$^+$ cell purification resulted in a 19.8-fold enrichment of ABCB5$^+$ cell frequency from 5.0±0.4% in unsegregated cultures to 98.8±0.8% (mean±SD, n=3, P<0.001) when assayed in representative samples using G3361 melanoma cells, and ABCB5$^+$-depletion resulted in a 4.75-fold reduction of ABCB5$^+$ cell frequency from 5.0±0.4% to 1.1±0.3% (mean±SD, n=3, P<0.001) (FIG. 5c). This residual contamination (22% of naturally occurring ABCB5$^+$ frequency) with ABCB5$^+$ cells may account for the observed tumor formation by ABCB5$^-$ inocula at the highest doses, and suggests potential underestimation of MMIC enrichment among ABCB5$^+$ populations. Notably, in those cases where tumor formation did occur as a result of ABCB5 cell injection at the highest cell doses, tumors were consistently found to be smaller than those resulting from ABCB5$^+$ xenografts (G3361: Tumor Volume (TV)=15±15 vs. 286±90 mm$^3$, respectively, mean±SEM, P<0.01; A375: TV=239±70 vs. 832±121 mm$^3$, respectively, mean±SEM, P<0.05) (FIGS. 2a and 2b).

Figure 2C:
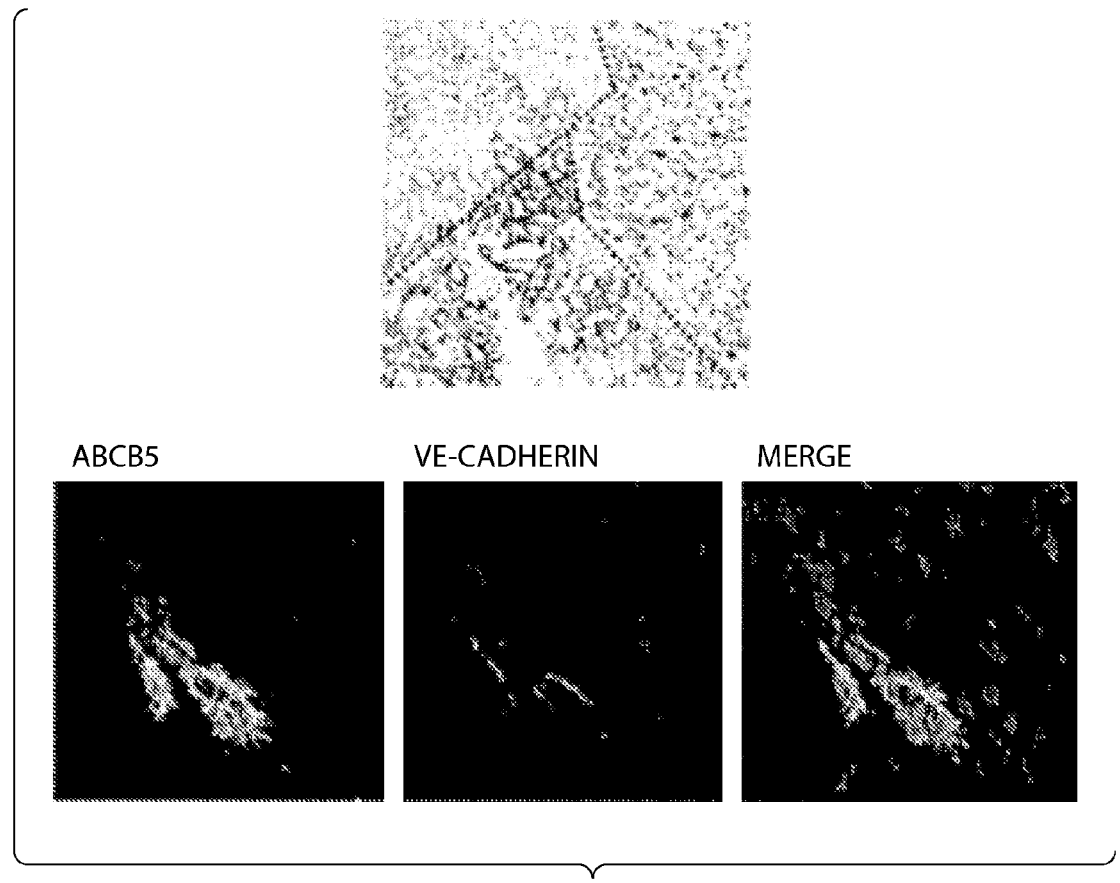
FIG. 2(c) (Left panel) shows the immunohistochemistry for ABCB5 expression in a representative primary, unsegregated melanoma cell-derived xenograft in NOD/SCID mice, illustrating three discrete zones demarcated by dotted lines: ABCB5−/melanin-negative (upper left of panel), ABCB5−/melanin-positive (upper right of panel), and ABCB5+/melanin-negative (bottom half of panel). (Right panel) is a series of images of immunofluorescence double staining of frozen melanoma xenograft sections for coexpression of ABCB5 (FITC) and VE-cadherin (Texas Red). Nuclei are visualized by staining with 4',6-diamidino-2-phenylindole (DAPI, blue).
Figure 2D:
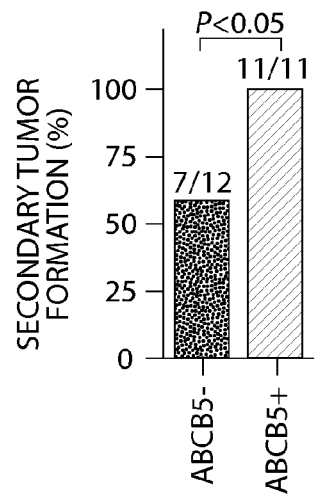
FIG. 2(d) is a graph depicting the secondary tumor formation capacity (%) in NOD/SCID mice of ABCB5− or ABCB5+ cells ($10^7$/inoculum) isolated from ABCB5+ melanoma cell-derived primary tumors.
Figure 2E:
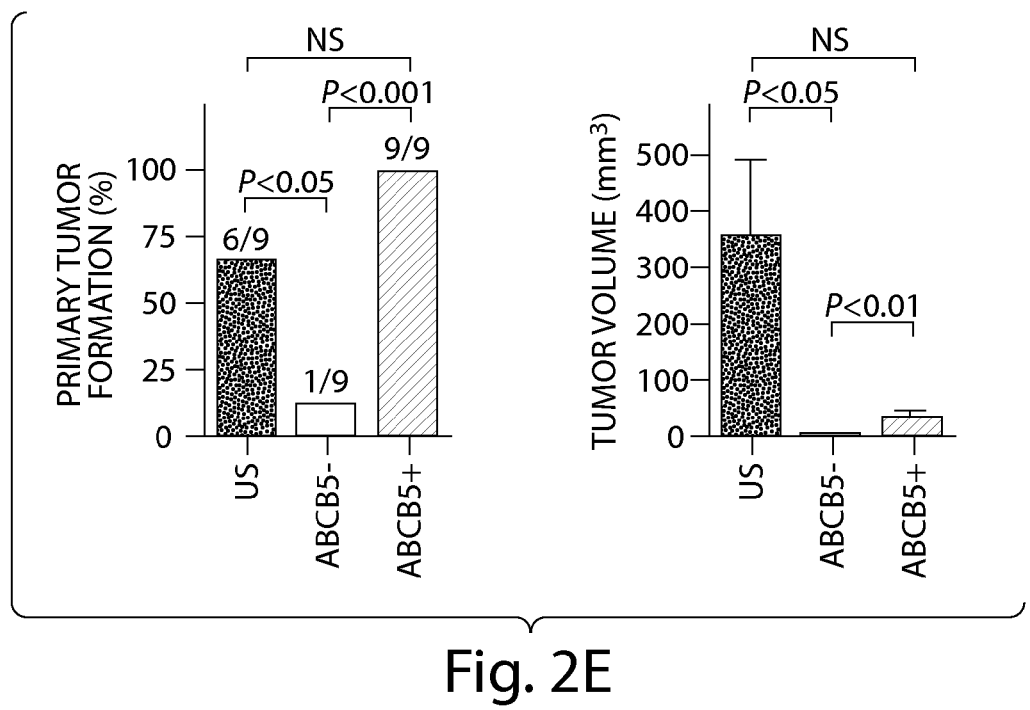
FIG. 2(e) contains two graphs depicting the in vivo tumor formation capacity (%) (left panel) and tumor volumes (mean±SEM, right panel) of unsegregated (US), ABCB5− or ABCB5 freshly patient-derived melanoma cells ($10^6$/inoculum) 8 weeks after s.c. xenotransplantation into NOD/SCID mice.

Melanoma culture xenografts were heterogeneous and comprised ABCB5$^+$ cells predominantly correlating with non-melanized regions and VE-cadherin expression, and ABCB5$^-$ zones corresponding to melanized areas (FIG. 2c). ABCB5$^+$ cells re-purified from ABCB5$^+$-derived primary tumors formed secondary tumors more efficiently than their ABCB5$^-$ counterparts in 11 of 11 vs. 7 of 12 recipients, respectively (P=0.037) (FIG. 2d) and re-established primary tumor heterogeneity. Consistent with the results obtained using clonal melanoma model systems, only 1 of 9 recipient mice injected with 10$^6$ freshly patient-derived ABCB5$^-$ melanoma cells developed a tumor, whereas all of 9 recipients of 10$^6$ ABCB5$^+$ melanoma cells formed tumors (P<0.001), with the mean TV smaller in recipients of ABCB5$^-$ vs. ABCB5$^+$ inocula (TV=2±2 vs. 35±11 mm$^3$, respectively, mean±SEM, P<0.01) (FIG. 2e, Table 1). Tumors generated from ABCB5$^+$ melanoma cells re-established naturally-occurring tumor heterogeneity with respect to ABCB5 expression, as determined by immunohistochemistry and flow cytometry of dissociated tumor specimen, with ABCB5 positivity ranging from 2 to 8% (results not illustrated). These findings establish that MMIC frequency is markedly enriched in the melanoma minority population defined by ABCB5.

Example 4

To directly examine the relative tumor growth contributions of co-xenografted ABCB5$^+$ and ABCB5$^-$ subpopulations, and to further investigate ABCB5+ self-renewal and differentiation capacity, we isolated ABCB5+ or ABCB5− melanoma cells from stably transfected G3361 cell line variants expressing either red fluorescent protein (DsRed2) or enhanced yellow-green fluorescent protein (EYFP), respectively, a model system designed in our laboratory to allow in vivo genetic lineage tracking. We found that xenotransplantation of ABCB5+ G3361/DsRed2 and ABCB5− G3361/EYFP fluorochrome transfectant co-cultures reconstituted at 14.0±3.0% and 86.0±3.0% relative abundance (mean±SD, n=6), respectively, to NOD/SCID mice resulted in time-dependent, serially increasing relative frequencies of DsRed2+ tumor cells of ABCB5+ origin (linear regression slope 6.4±1.0, P<0.0001) in experimental tumors compared to inoculates, up to a frequency of 51.3±1.4% at the experimental endpoint of 6 weeks (mean±SD, n=3, P=0.024) (FIGS. 3a, 3b, and 3c top and bottom panels). These findings establish greater tumorigenicity of ABCB5+ vs. co-xenografted ABCB5− melanoma bulk populations in a competitive tumor development model. Importantly, these results further indicate that tumor initiating cells may in addition drive more differentiated, and on their own non-tumorigenic cancer bulk populations to also, albeit less efficiently, contribute to a growing tumor mass. Experimental tumors also contained DsRed21EYFP double-positive melanoma cells (FIG. 3c center panels), indicating that ABCB5+-derived tumor cells, like physiological ABCB5+ skin progenitors (Frank, N. Y. et al. Regulation of progenitor cell fusion by ABCB5 P-glycoprotein, a novel human ATP-binding cassette transporter. J Biol Chem 278, 47156-65 (2003)), engage in cell fusion with ABCB5− subsets.

Example 5

Figure 3A:
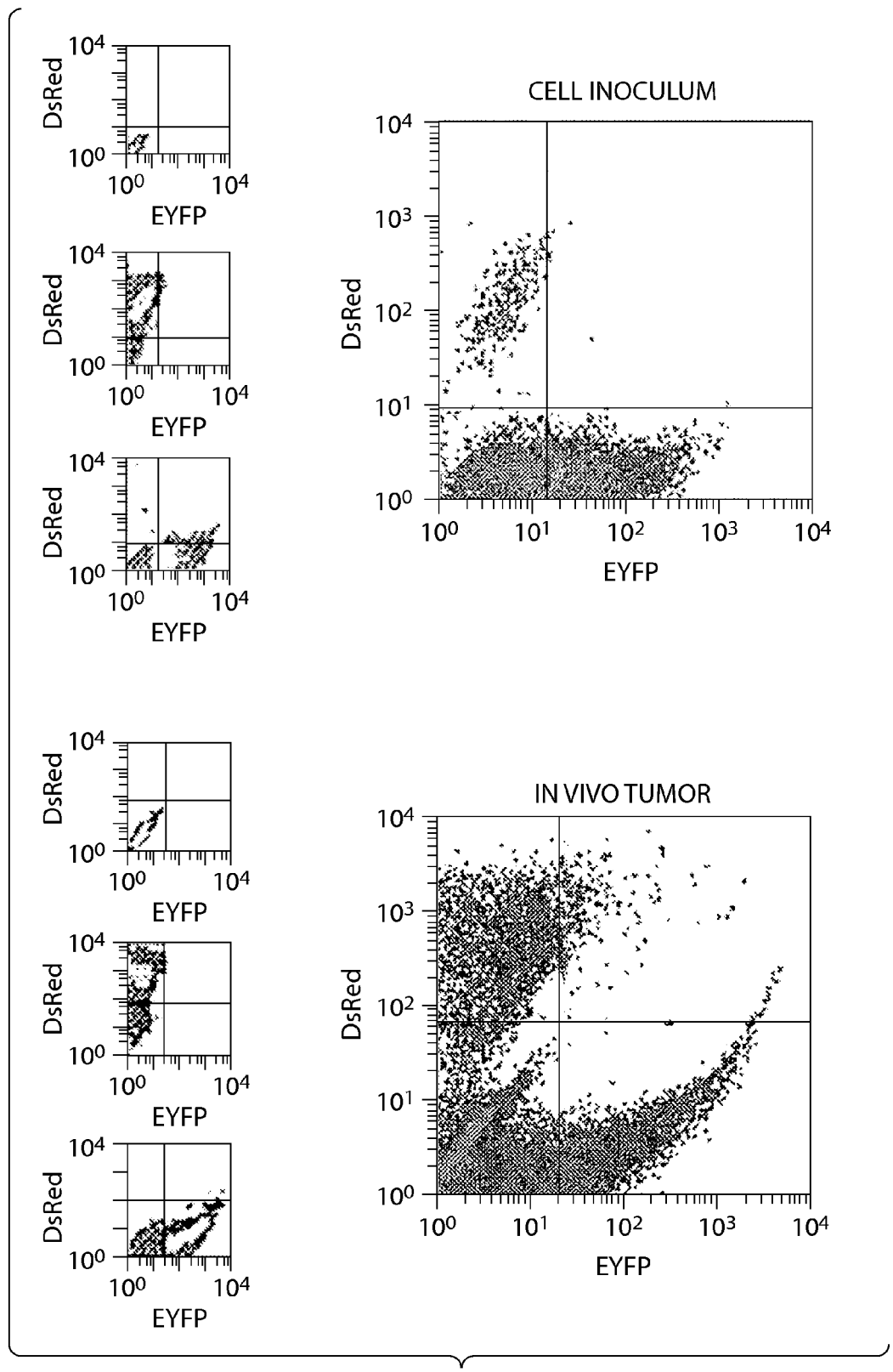
FIG. 3(a) (Left panels) shows the dual-color flow cytometry (Fl1 (EYFP) vs. Fl2 (DsRed2) dot plots) of a tumor cell inoculum consisting of 10% ABCB5+ G3361/DsRed2 and 90% ABCB5− G3361/EYFP cells prior to xenotransplantation (shown in large panel). Controls (shown in small panels) are non-transfected G3361 human melanoma cells (top), G3361/DsRed2 cells (middle), and G3361/EYFP cells (bottom). (Right panels) show the dual-color flow cytometry (EYFP) vs. Fl2 (DsRed2) dot plots) of a dissociated xenograft tumor formed 6 weeks after inoculation of 10% ABCB5+ G3361/DsRed2 and 90% ABCB5− G3361/EYFP cells (shown in large panel). Controls (shown in small panels) are non-transfected G3361 human melanoma cells (top), G3361/DsRed2 cells (middle), and G3361/EYFP cells (bottom).
Figure 3B:
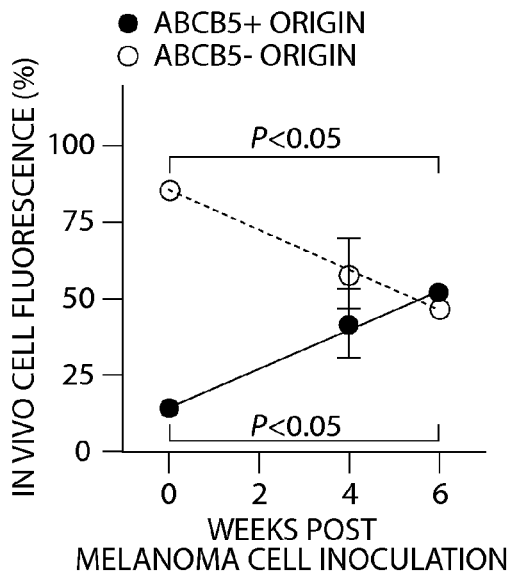
FIG. 3(b) is a graph of the mean percentage (mean±SEM) of DsRed2+ cells (% DsRed2+/(% DsRed2++% EYFP+)×100) of ABCB5+ origin or of EYFP+ cells (% EYFP+/(% DsRed2++% EYFP+)×100) of ABCB5− origin plotted against weeks post melanoma cell inoculation for resultant in vivo tumors at t=4 or 6 weeks (n=3 replicates, respectively) and respective xenografted cell inocula (n=6).
Figure 3C:
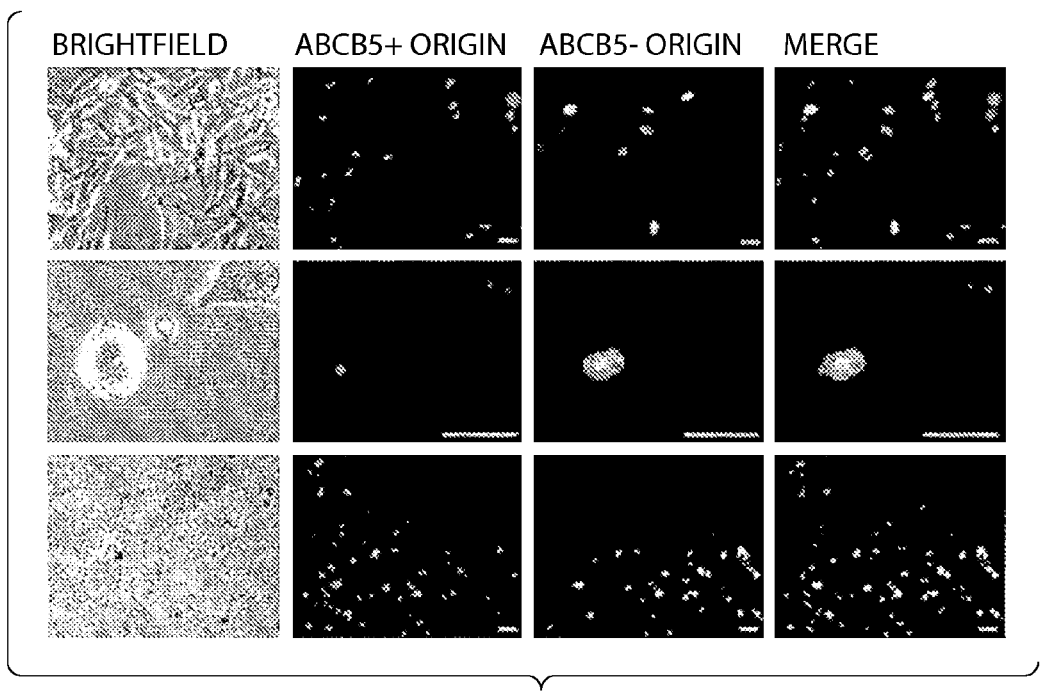
FIG. 3(c) is a series of dual-channel fluorescence microscopy images of G3361/DsRed2 and G3361/EYFP cells (top and center rows) and of a frozen tissue section (bottom row) derived from in vivo-formed tumors 6 weeks after s.c. xenotransplantation into NOD/SCID mice of 10% G3361/DsRed2 ABCB5+ and 90% G3361/EYFP ABCB5− cell inocula. The left panels show brightfield, the middle left panels show DsRed2 (ABCB5+ origin), the middle right panels show EYFP (ABCB5− origin), and the right-most panels show merged images (size bars: 25 μm).
Figure 3D:
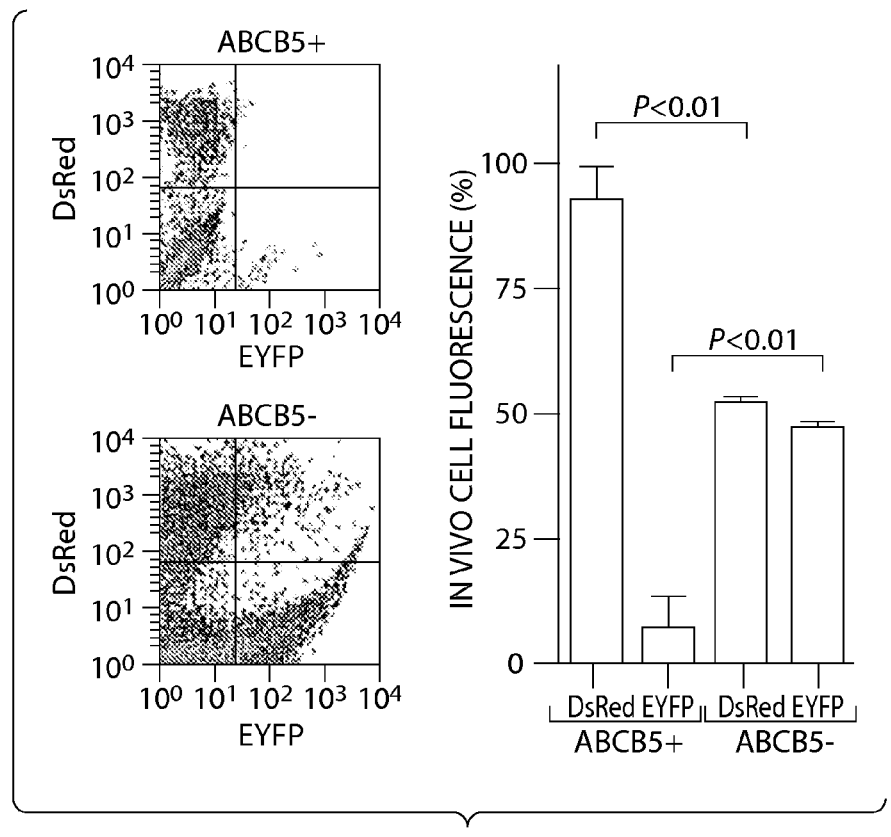
FIG. 3(d) (Left panels) Depict the flow cytometric analysis of DsRed2 and EYFP expression in ABCB5+ cells (top) and ABCB5− cells (bottom) derived from tumors formed in NOD/SCID mice 6 weeks after inoculation of 10% ABCB5+ G3361/DsRed2 and 90% ABCB5− G3361/EYFP cells. (Right panel) is a graph depicting the mean percentage (mean±SD) of either DsRed2 or EYFP fluorescent cells (calculated as % DsRed2+/(% DsRed2++% EYFP+)×100 or % EYFP+/(% DsRed2++% EYFP+)×100, respectively) in ABCB5+ and ABCB5− cell subsets derived from n=3 replicate tumors.

When ABCB5+ melanoma cells were purified from experimental tumors resulting from co-xenotransplantation of 10% ABCB5+ G3361/DsRed2 and 90% ABCB5− G3361/EYFP fluorochrome transfectants, we found 92.9±6.4% (mean±SD, n=3) of fluorescent cells to be of DsRed2+ phenotype (ABCB5+ origin) (FIG. 3d, upper left panel), demonstrating self renewal capacity of this cell subset. EYFP+ cells were not found at significant levels (7.1±6.4%, mean±SD, n=3) among ABCB5+ isolates, and the observed low frequency was fully accounted for in magnitude by the measured residual ABCB5+ cell contamination among co-grafted ABCB5− EYFP+ populations (1.1% of 90% EYFP+ cells=0.99% vs. 10% ABCB5+ DsRed2+ cells in inocula), indicating that ABCB5+ tumor cells arose only from ABCB5+ inocula and that ABCB5− cells give rise exclusively to ABCB5− progeny. Moreover, fluorescent ABCB5− tumor cell isolates exhibited 52.5±0.8% (mean±SD, n=3) DsRed2 positivity (ABCB5+ origin) and 47.5±0.8% EYFP positivity (ABCB5− origin) (FIG. 3d, lower left panel), demonstrating that ABCB5+ melanoma cells possess the capacity to differentiate and give rise to ABCB5− tumor populations. These findings show the existence of a tumor hierarchy in which ABCB5+ melanoma cells, enriched for MMIC, self-renew and give rise to more differentiated, ABCB5− tumor progeny.

Example 6

Figure 4A:
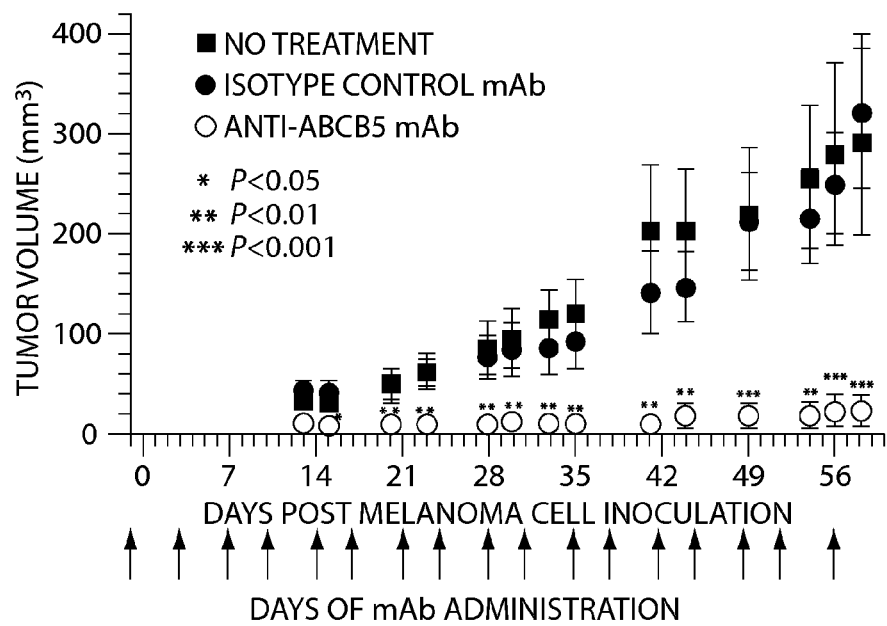
FIG. 4(a) is a graph measuring the tumor volumes (mean±SEM) of melanoma xenografts plotted against days after s.c. melanoma cell inoculation into Balb/c nude mice ($10^7$ cells/inoculum) for untreated (n=18), isotype control mAb-treated (n=10), or anti-ABCB5 mAb-treated (n=11) animals. [Days of i.p. mAb administration are indicated by arrows.]
Figure 4B:
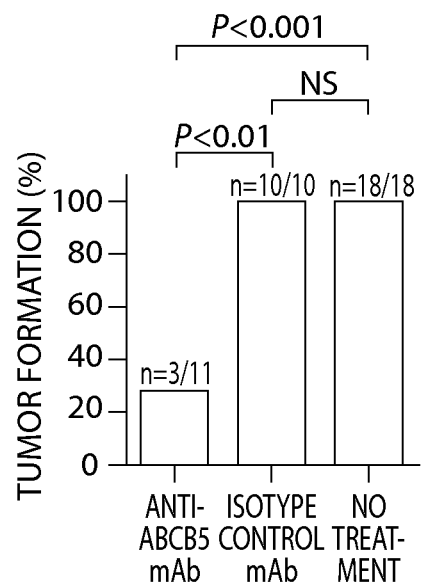
FIG. 4(b) is a graph measuring the tumor formation rate (%) 58 days after s.c. melanoma cell inoculation into Balb/c nude mice ($10^7$ cells/inoculum) in untreated (n=18), isotype control mAb-treated (n=10), or anti-ABCB5 mAb-treated (n=11) animals.

In order to mechanistically dissect whether the ABCB5-defined, MMIC-enriched minority population is required for tumorigenicity when unsegregated tumor bulk populations are xenografted, we examined whether selective killing of this cell subset can inhibit tumor growth and formation. A prospective molecular marker of tumor initiating cells has not been targeted to date for in vivo inhibition of tumor growth. We administered a monoclonal antibody (mAb) directed at ABCB5 in a human to nude mouse melanoma xenograft model, because nude, as opposed to NOD/SCID, mice are capable of antibody dependent cellular cytotoxicity (ADCC)-mediated tumor cell killing. Melanoma cells were xenografted s.c. into recipient Balb/c nude mice, the animals were injected i.p. with anti-ABCB5 mAb or control mAb bi-weekly starting 24 hrs prior to melanoma xenotransplantation, and tumor formation and growth were serially assessed by TV measurements as a time course. Administration of anti-ABCB5 mAb resulted in significantly inhibited tumor growth compared to that determined in control mAb-treated or untreated mice over the course of a 58-day observation period (mean TV at the endpoint of 58 days for anti-ABCB5 mAb-treated=11 mice, no death during the observation period) vs. control mAb-treated (n=10 mice, excluding 1 death during the observation period) or vs. untreated (n=18 mice, excluding 1 death during the observation period): 23±16 vs. 325±78 mm$^3$, P<0.01, or vs. 295±94 mm$^3$, P<0.001, mean±SEM, respectively) (FIG. 4a). Control mAb-treatment showed no significant difference in tumor growth compared to no treatment (FIG. 4a). Anti-ABCB5 mAb-treatment also significantly inhibited tumor formation assessed at 58 days following melanoma cell xenotransplantation, with tumors detected in only 3 of 11 anti-ABCB5 mAb-treated mice, vs. 10 of 10 control mAb-treated mice and 18 of 18 untreated control animals (P<0.01 and P<0.001, respectively) (FIG. 4b).

Example 7

Figure 4C:
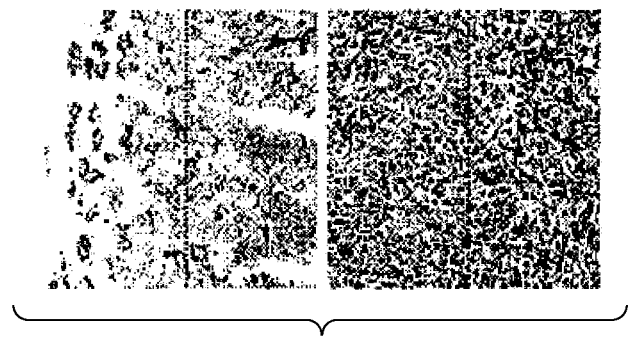
FIG. 4(c) depicts the ABCB5 immunohistochemistry (left panel) and conventional histology (H&E) (right panel) of human melanoma xenografts in nude mice. (Panels represent adjacent sections.) ABCB5+ regions segregate with unmelanized areas (to left of central dotted line), whereas ABCB5⁻ regions correlate with regions showing particulate brown-black melanization (to right of central dotted line).
Figure 4D:
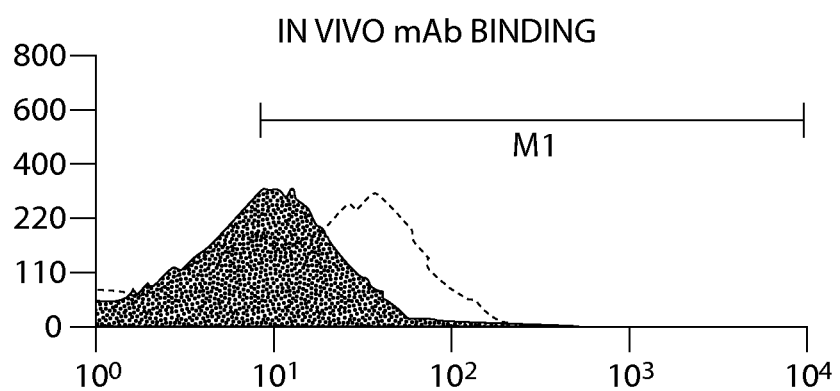
FIG. 4(d) shows the flow cytometry analysis (FITC, Fl1) for surface-bound antibody in melanoma xenografts, 1 day post i.p. administration of anti-ABCB5 mAb (solid line) or isotype control mAb (shaded). A representative melanoma xenograft isolated from an anti-ABCB5 mAb-treated mouse exhibited 20.5% positivity compared to one derived from an isotype control-treated animal.

Human melanoma xenografts grown in untreated nude mice, like those in NOD/SCID recipients, display tumor heterogeneity and comprise a minority population of ABCB5+ cells predominantly correlating with undifferentiated, non-melanized regions, and ABCB5− zones corresponding to differentiated, melanized areas (FIG. 4c). Analysis of in vivo binding efficacy revealed that systemically administered anti-ABCB5 mAb, but not control mAb, bound to a subset of tumor cells in established melanoma xenografts (FIG. 4d) consistent in magnitude with the ABCB5+ tumor cell subset (FIG. 4c), as quantitatively determined in xenograft-derived cell suspensions by flow cytometry (FIG. 4d), and also by immunohistochemistry by detection of positively staining cell clusters.

Example 8

Figure 4E:
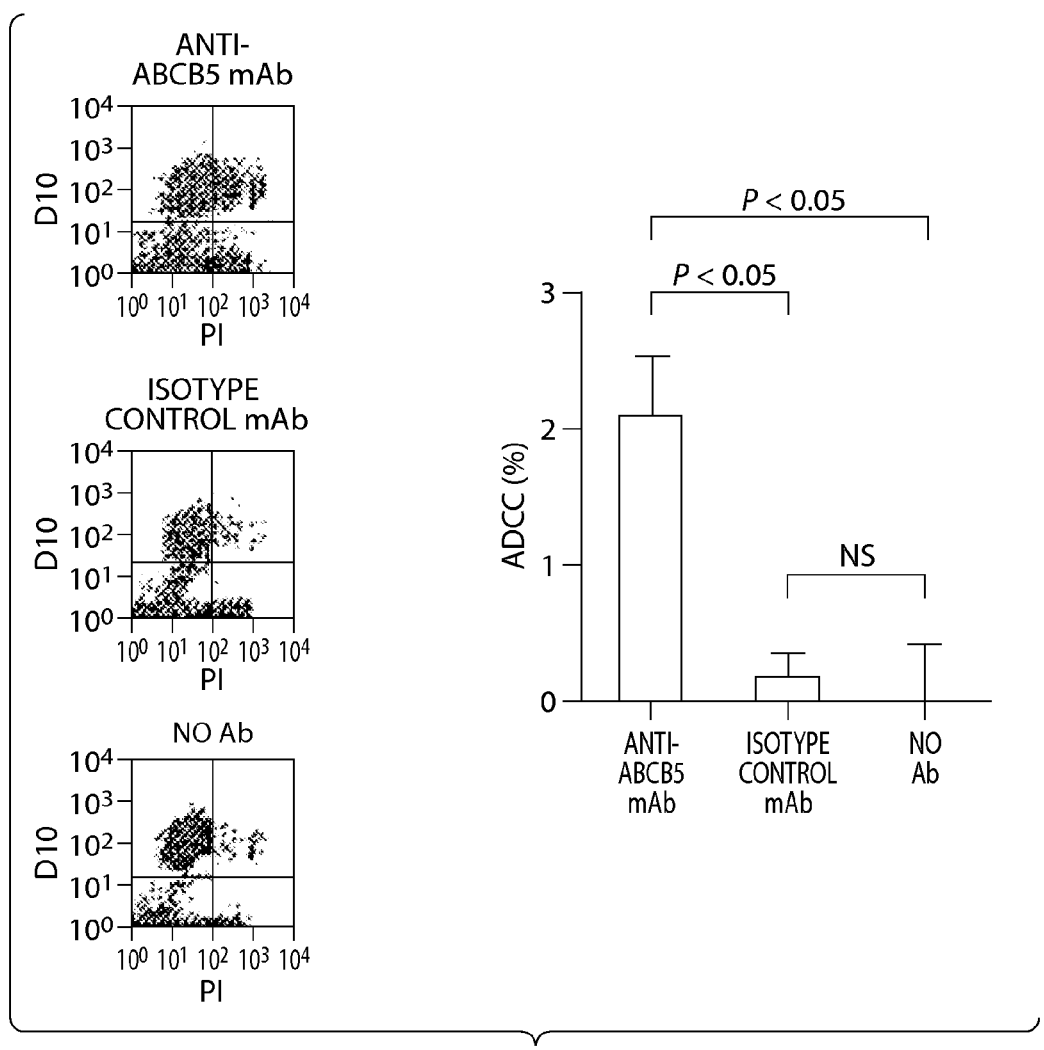
FIG. 4(e) summarizes an assessment of antibody-dependent cell-mediated cytotoxicity (ADCC) by dual color flow cytometry in anti-ABCB5 mAb-, or isotype control mAb-treated or untreated DiO-labeled melanoma target cell cultures counterstained with propidium iodide (PI) following 24 h coculture with unlabeled effector immune cells derived from Balb/c nude mouse spleens (1:40 target to effector ratios). (Left panels) are a series of representative dual-color flow cytometric results of ADCC with lysed, DIO⁺PI⁺ target cells found in the right upper quadrants of anti-ABCB5 mAb-treated (top), isotype control mAb-treated (center), or Ab-untreated (bottom) target/effector cocultures. (Right panel) depicts an analysis of ADCC (% mean±SEM) in n=6 replicate experiments in treatment groups as above as illustrated ([ADCC (%)=(DIO⁺PI⁺ percent sample positivity)−(mean Ab-untreated DIO⁺PI⁺ percent sample positivity)]).

To determine the mechanism of anti-ABCB5 mAb-mediated inhibition of tumor formation and growth, the immune effector responses ADCC and complement-dependent cytotoxicity (CDC) were assessed by dual-color flow cytometry as previously described. Anti-ABCB5 mAb-treated, control mAb-treated or untreated melanoma target cultures were labeled with the green-fluorescent membrane dye DiO and counterstained with red-fluorescent propidium iodide (PI, to which only lysed cells are permeable), following co-culture with unlabeled effector immune cells or serum derived from Balb/c nude mouse spleens. Anti-ABCB5 mAb but not isotype control mAb significantly induced ADCC-mediated melanoma target cell death (2.1±0.4% vs. 0.2±0.2%, respectively, P<0.05) in a melanoma subpopulation comparable in size to the ABCB5-expressing subset (Frank, N. Y. et al. ABCB5-mediated doxorubicin transport and chemoresistance in human malignant melanoma. Cancer Res 65, 4320-33 (2005)), as determined from the percentage of DiO/PI double-positive cells (FIG. 4e). Addition of serum to Ab-treated cultures in the absence of effector cells, or addition of anti-ABCB5 mAb alone under these experimental conditions did not induce significant cell death compared to controls (results not illustrated), suggesting CDC or direct toxic mAb effects are not the significant causes of tumor inhibition in this experimental system.

The effects of ABCB5 targeting on established human to nude mouse melanoma xenografts (n=13 derived from three distinct patients and n=10 derived from established melanoma cultures), was examined in order to test the hypothesis that negative selection for MMIC via ADCC-mediated ABCB5+ cell ablation inhibits tumour growth. Such a result would be observed in a dynamic in vivo situation if the ABCB5+ melanoma subset is critical to robust tumourigenesis.

Characterization of ABCB5+ or ABCB5− human melanoma cells used in xenotransplantation experiments was undertaken. In vivo anti-ABCB5 mAb administration, started 14 days following tumour cell inoculation when xenografts were established (day 0), abrogated the significant tumour growth observed in isotype control mAb-treated or untreated groups over the course of a 21-day treatment period (P<0.001 and P<0.001, respectively) and significantly inhibited mean tumour volume compared to that determined in either control mAb-treated or untreated mice (TV for anti-ABCB5 mAb-treated (n=23 mice) vs. control mAb-treated (n=22 mice) or vs. untreated (n=22 mice): 32.7±9.4 vs. 226.6±53.8 mm3, P<0.001, or vs. 165.4±36.9 mm$^3$, respectively, mean±s.e.m., P<0.01). The inhibitory effects of ABCB5 mAb were also statistically significant when the subsets of freshly patient-derived melanoma xenograft tumours were analyzed independently, with abrogation of the significant tumour growth observed in isotype control mAb-treated or untreated groups (P<0.05 and P<0.001, respectively) and significantly inhibited mean TV compared to that determined in either control mAb-treated or untreated mice (anti-ABCB5 mAb-treated (n=13 mice) vs. control mAb-treated (n=12 mice) or vs. untreated (n=12 mice): 29.6±9.2 vs. 289.2±91.8 mm$^3$, P<0.05, or vs. 222.9±57.5 mm$^3$, respectively, mean±s.e.m., P<0.001). Control mAb-treatment showed no significant effects on tumour growth or tumour volume compared to no treatment in any of the groups analyzed. The animals were sacrificed following the treatment interval as required by the applicable experimental animal protocol because of tumour burden and disease state in the patient-derived tumour control groups (measured maximal TV: 971.5 mm$^3$).

Immunohistochemical analysis of anti-ABCB5 mAb-treated patient-derived melanoma xenografts revealed only small foci of ABCB5 expression (overall <1% of cells) corresponding to in vivo-bound anti-ABCB5 mAb in an adjacent section. An additional adjacent section stained for CD11b disclosed macrophage infiltration corresponding with regions of anti-ABCB5 mAb localization, that frequently bordered zones of cellular degeneration and necrosis. In contrast, control mAb-treated xenografts revealed 10-15% ABCB5-reactive cells, secondary anti-Ig mAb failed to localize to the respective regions in an adjacent section but detected regions of intravascular murine immunoglobulin, and CD11b+ macrophages failed to infiltrate the tumour tissue. Similar effects were observed in cell line-derived melanoma xenografts, with enhanced tumour necrosis in anti-ABCB5 mAb-treated vs. isotype control mAb-treated animals (30-40% vs. <5% necrotic cells, respectively). These findings further support the notion that the ABCB5-defined, MMIC enriched minority population is required for tumourigenicity.

Characterization of G3361 melanoma xenografts to Balb/c nude mice was performed. ABCB5+ regions segregated with unmelanized areas, whereas ABCB5-regions correlate with regions showing particulate brown-black melanization. Immunohistochemistry of a melanoma xenograft treated with anti-ABCB5 mAb and stained with anti-ABCB5 mAb, secondary anti-Ig Ab or CD11b mAb revealed consistent results to those described above. As in primary patient-derived xenografts, immunohistochemical analysis of adjacent tumour sections revealed that systemically administered anti-ABCB5 mAb bound to ABCB5+ tumour regions, which also correlated with CD11b+ cell infiltration. Rare areas of ABCB5 expression to which in vivo administered antibody failed to localize and into which CD11b-positive cells failed to infiltrate were also detected.

Example 9

Sequencing of Antibody 3C1 1D12: Total RNA was extracted from the pellets using Fusion Antibodies Ltd in-house RNA extraction protocol. cDNA was created from the RNA by reverse-transcription with an oligo(dT) primer. PCR reactions using variable domain primers to amplify the heavy chain (HC) variable region (VR) and light chain (LC) VR regions of the monoclonal antibody DNA gave bands shown in FIG. 7. Both HC and LC VR PCR products were cloned into the Invitrogen sequencing vector pCR2.1 and transformed into TOP10 cells. Positive clones for the heavy and light chain were picked for sequencing analysis. The following sequences were obtained.

1. DNA Sequence of full length HC, including signal sequence (underlined)

SEQ ID NO: 17
<u>ATGGACTTTGGGCTGAGCTTGGTTTTCCTTGTCCTTGTTTTAAAAGGTG</u>

<u>TCCAGTGT</u>GAAGTGCAACTGGTGGAGTCTGGGGGAGACTTAGTGAAGCC

TGGAGGGTCCCTGAAGCTCTCCTGTGCAGCCTCTGGATTCACTTTCAGT

GACTATTACATGTATTGGGTTCGTCAGACTCCGGAAAAGAGGCTGGAGT

GGGTCGCCACCATTAATGATGGCGGTACTCACACCTACTATCCAGACAG

TCTGAAGGGGCGATTCACCATCTCCAGAGACAATGCCAAGAACATCCTG

TACCTGCAAATGAGCAGTCTGATGTCTGAGGACACAGCCATGTATTATT

GTGCAAGAGATGATTATTACTACGGTAGTCACTTCGATGCTATGGACTA

CTGGGGTCAAGGAACCTCAGTCACCGTCTCCTCAGCCTCCACCAAGGGC

CCATCGGTCTTCCCCCTGGCACCCTCCTCCAAGAGCACCTCTGGGGGCA

CAGCGGCCCTGGGCTGCCTGGTCAAGGACTACTTCCCCGAACCGGTGAC

GGTGTCGTGGAACTCAGGCGCCCTGACCAGCGGCGTGCACACCTTCCCG

GCTGTCCTACAGTCCTCAGGACTCTACTCCCTCAGCAGCGTGGTGACCG

TGCCCTCCAGCAGCTTGGGCACCCAGACCTACATCTGCAACGTGAATCA

CAAGCCCAGCAACACCAAGGTGGACAAGAAAGTTGAGCCCAAATCTTGT

GACAAAACTCACACATGCCCACCGTGCCCAGCACCTGAACTCCTGGGGG

GACCGTCAGTCTTCCTCTTCCCCCCAAAACCCAAGGACACCCTCATGAT

CTCCCGGACCCCTGAGGTCACATGCGTGGTGGTGGACGTGAGCCACGAA

GACCCTGAGGTCAAGTTCAACTGGTACGTGGACGGCGTGGAGGTGCATA

ATGCCAAGACAAAGCCGCGGGAGGAGCAGTACAACAGCACGTACCGGGT

```
GGTCAGCGTCCTCACCGTCCTGCACCAGGACTGGCTGAATGGCAAGGAG

TACAAGTGCAAGGTCTCCAACAAAGCCCTCCCAGCCCCCATCGAGAAAA

CCATCTCCAAAGCCAAAGGGCAGCCCCGAGAACCACAGGTGTACACCCT

GCCCCCATCCCGGGATGAGCTGACCAAGAACCAGGTCAGCCTGACCTGC

CTGGTCAAAGGCTTCTATCCCAGCGACATCGCCGTGGAGTGGGAGAGCA

ATGGGCAGCCGGAGAACAACTACAAGACCACGCCTCCCGTGCTGGACTC

CGACGGCTCCTTCTTCCTCTACAGCAAGCTCACCGTGGACAAGAGCAGG

TGGCAGCAGGGGAACGTCTTCTCATGCTCCGTGATGCATGAGGCTCTGC

ACAACCACTACACGCAGAAGAGCCTCTCCCTGTCTCCGGGTAAATGA
```

2. DNA Sequence of full length LC, including signal sequence (underlined)

SEQ ID NO: 18
```
ATGGAGACAGACACACTCCTGCTATGGGTACTGCTGCTCTGGGTTCCAG

GTTCCACTGGTGACATTGTGCTGACACAGTCTCCTGCTTCCTTAGCTGT

ATCTCTGGGGCAGAGGGCCACCATCTCATACAGGGCCAGCAAAAGTGTC

AGTACATCTGGCTATAGTTATATGCACTGGAACCAACAGAAACCAGGAC

AGCCACCCAGACTCCTCATCTATCTTGTATCCAACCTAGAATCTGAGGT

CCCTGCCAGGTTCAGTGGCAGTGGGTCTGGGACAGACTTCACCCTCAAC

ATCCATCCTGTGGAGGAGGAGGATGCTGCAACCTATTACTGTCAGCACA

TTAGGGAGCTTACACGTTCGGAGGGGGGCACCAAGCTGGAAATCAAACG

GACTGTGGCTGCACCATCTGTCTTCATCTTCCCGCCATCTGATGAGCAG

TTGAAATCTGGAACTGCCTCTGTTGTGTGCCTGCTGAATAACTTCTATC

CCAGAGAGGCCAAAGTACAGTGGAAGGTGGATAACGCCCTCCAATCGGG

TAACTCCCAGGAGAGTGTCACAGAGCAGGACAGCAAGGACAGCACCTAC

AGCCTCAGCAGCACCCTGACGCTGAGCAAAGCAGACTACGAGAAACACA

AAGTCTACGCCTGCGAAGTCACCCATCAGGGCCTGAGCTCGCCCGTCAC

AAAGAGCTTCAACAGGGGAGAGTGTTGA
```

3. DNA Sequence of HC VR, including CRDs (underlined)

SEQ ID NO: 9
```
GAAGTGCAACTGGTGGAGTCTGGGGGAGACTTAGTGAAGCCTGGAGGGT

CCCTGAAGCTCTCCTGTGCAGCCTCTGGATTCACTTTCAGTGACTATTA

CATGTATTGGGTTCGTCAGACTCCGGAAAAGAGGCTGGAGTGGGTCGCC

ACCATTAATGATGGCGGTACTCACACCTACTATCCAGACAGTCTGAAGG

GGCGATTCACCATCTCCAGAGACAATGCCAAGAACATCCTGTACCTGCA

AATGAGCAGTCTGATGTCTGAGGACACAGCCATGTATTATTGTGCAAGA

GATGATTATTACTACGGTAGTCACTTCGATGCTATGGACTACTGGGGTC

AAGGAACCTCAGTCACCGTCTCCTCA
```

4. DNA Sequence of LC VR, including CRDs (underlined)

SEQ ID NO: 10
```
GACATTGTGCTGACACAGTCTCCTGCTTCCTTAGCTGTATCTCTGGGGC

AGAGGGCCACCATCTCATACAGGGCCAGCAAAAGTGTCAGTACATCTGG

CTATAGTTATATGCACTGGAACCAACAGAAACCAGGACAGCCACCCAGA

CTCCTCATCTATCTTGTATCCAACCTAGAATCTGAGGTCCCTGCCAGGT

TCAGTGGCAGTGGGTCTGGGACAGACTTCACCCTCAACATCCATCCTGT

GGAGGAGGAGGATGCTGCAACCTATTACTGTCAGCACATTAGGGAGCTT

ACACGTTCGGAGGGGGGCACCAAGCTGGAAATCAAACGG
```

5. Amino Acid Sequence of HC VR, including Framework Regions (F1, F2, F3, and F4) and CRDs (CDR-H1, CDR-H2 and CDR-H3) as marked. The framework and CDR regions are determined according to the Kabat nomenclature (E. A. Kabat et al. Sequences of Proteins of Immunological Interest, Fifth Edition, 1991, NIH).

SEQ ID NO: 1
```
HC-F1                          CDR-H1
EVQLVESGGDLVKPGGSLKLSCAASGFTFS DYYMY

HC-F2         CDR-H2     HC-F3
WVRQTPEKRLEWVA TINDGGTHTY YPDSLKGRFTISRDNAKNILYLQ

CDR-H3         HC-F4
MSSLMSEDTAMYYCAR DDYYYGSHFDAMDY WGQGTSVTVSS
```

6. Amino Acid Sequence of LC VR, including Framework Regions (F1, F2, F3, and F4) and CRDs (CDR-L1, CDR-L2 and CDR-L3) as marked. The framework and CDR regions are determined according to the Kabat nomenclature (E. A. Kabat et al. Sequences of Proteins of Immunological Interest, Fifth Edition, 1991, NIH).

SEQ ID NO: 2
```
LC-F1                      CDR-L1              LC-F2
DIVLTQSPASLAVSLGQRATISY RASKSVSTSGYSYMH WNQQKPGQ

CDR-L2    LC-F3
PPRLLIY LVSNLES EVPARFSGSGSGDTFTLNIHPVEEEDAATYYC

CDR-L3    LC-F4
QHIRELTR SEGGTKLEIKR
```

7. CDR-H1, CDR-H2 and CDR-H3 Sequences:

CDR-H1: DYYMY            SEQ ID NO: 3

CDR-H2: TINDGGTHTY       SEQ ID NO: 4

CDR-H3: DDYYYGSHFDAMDY   SEQ ID NO: 5

8. CDR-L1, CDR-L2 and CDR-L3 Sequences:

CDR-L1: RASKSVSTSGYSYMH  SEQ ID NO: 6

CDR-L2: LVSNLES          SEQ ID NO: 7

CDR-L3: QHIRELTR         SEQ ID NO: 8

Example 10

Future Studies

We will study the ability to influence melanoma growth and progression by employing a) two complementary sources of human melanoma (established human melanoma cell lines and freshly isolated melanoma cells derived from primary and metastatic human tumors); b) two model systems for the study of these cells (subcutaneous screening of tumorigenesis in immunodeficient mice, and more relevant tumorigenesis as it occurs in authentic human skin xenografts); and c) two alternative strategies for melanoma stem cell abrogation (chemosensitization via ABCB5 functional blockade, and stem cell killing via immunotoxin or inhibitory siRNAs delivered specifically to ABCB5+ stem cell targets).

We will investigate whether ABCB5-targeted melanoma stem cell chemoresistance reversal can also inhibit tumor initiation/progression in chimeric Rag2−/− mouse/human skin xenografts in vivo.

Tumor-targeted immunotoxins have successfully been constructed by conjugating mAbs directed at tumor site-specific antigens to otherwise indiscriminately cytotoxic agents such as toxins, radionuclides, and growth factors. For the proposed studies we will initially focus on utilizing one such molecule, gelonin, a 29 kDa ribosome-inactivating plant toxin, because gelonin, when used in immunoconjugates directed at melanoma-specific antigens, has already been demonstrated to exert tumor-specific cytotoxicity in A375 human melanoma xenograft models also employed in this proposal, indicating that gelonin immunoconjugates are excellent candidates for clinical development. In other future studies, we also envision to study radionuclide immunoconjugates involving for example Yttrium, which is known to exerts anti-melanoma effects. When using ABCB5-targeted gelonin immunotoxins as a strategy to selectively ablate ABCB5+ melanoma xenograft subpopulations in vivo, ABCB5-targeted gelonin immunotoxins will involve gelonin/anti-ABCB5 3C2-1D12 mAb or gelonin/isotype control mAb chemical conjugates synthesized and purified as previously described. In addition, due to the potential limitations of intact mAb immunoconjugates with regard to tumor penetration, we will also use recombinant anti-ABCB5 3C2-1D12 sFv/gelonin fusion proteins, which will be constructed by fusion of the anti-ABCB5 3C2-1D12 sFv gene, generated as above, to gelonin DNA, using the splice-overlap extension PCR method. The recombinant fusion immunotoxin will be expressed in *E. coli* and purified as previously described. Recombinant control sFv/gelonin fusion proteins will be generated in an identical manner from isotype control mAb-producing murine hybridoma cell lines.

We will also develop and use ABCB5 antibody-mediated, target cell-specific delivery of siRNAs to specific oncogenes as a strategy to selectively inhibit ABCB5+ melanoma tumor stem populations in vivo. While delivery of small interfering RNAs (siRNAs) into cells has until recently been a key obstacle to their in vivo therapeutic application, a novel approach involving antibody/protamine fusion proteins as siRNA delivery vehicles, has recently demonstrated efficacy in systemic, cell-type specific siRNA delivery to melanoma tumors in experimental animal models in vivo, and proved effective in inhibiting in vivo melanoma growth when siRNAs directed at MYC, MDM2 and VEGF were antibody-targeted to a model receptor expressed on B16 murine melanoma cells. This approach takes advantage of the nucleic acid-binding properties of protamine, which normally nucleates DNA in sperm, to bind siRNAs of various specificities and deliver them to cells bearing a specific cell surface marker when protamine is fused to antibody Fab fragments or sFv specifically directed to such a marker. In order to utilize this strategy to target ABCB5-expressing melanoma stem cells, we will construct a recombinant anti-ABCB5 3C2-1D12 sFv/protamine fusion protein (ABCB5 sFv-P), by fusion of the anti-ABCB5 3C2-1D12 sFv gene to protamine DNA, using the splice-overlap extension PCR method. The recombinant fusion protein ABCB5 sFv-P will be expressed and purified as previously described. ABCB5 sFv-P will initially be used to deliver siRNA targeted to MYC, since gene-targeted MYC down-regulation inhibits in vivo tumor growth not only in murine B16 melanoma, but also in mice bearing established human melanoma xenografts, leading to extensive tumor cell apoptosis via induction of p53 and inhibition of Bcl-2 proteins. We have already found MYC consistently expressed in ABCB5+ human melanoma subpopulations. Furthermore, gene expression of human MYC can be effectively inhibited by RNAi approaches, and MYC-targeting siRNA oligonucleotides validated in these studies are commercially available from Dharmacon, Inc. (Chicago, Ill.). In the proposed studies, the ABCB5 sFv-P binding capacity for MYC siRNA, the ABCB5 sFv-P-mediated MYC siRNA target cell delivery and resultant MYC gene inhibition, and ABCB5 sFv-P/MYC siRNA-mediated blockade of tumor cell proliferation will first be examined in vitro in human G3361 and A375 melanoma cultures exactly as described previously.

The in vivo study protocol for ABCB5+ melanoma stem cell targeting will employ the human to mouse tumor xenograft models utilizing both NOD-SCID mice as well as chimeric Rag2−/−/human skin chimeric mice as recipients of human melanoma xenografts either derived from established cell lines or freshly isolated from human patients, exactly as already described above. In a first set of experiments aimed at assessing the effects of immunotoxins (ABCB5 mAb/gelonin or sFv/gelonin) or of ABCB5 sFv-P/MYC siRNA on tumor initiation, immunotoxins (ABCB5 mAb/gelonin or sFv/gelonin or controls) will be administered in 0.25 ml sterile PBS via tail vein injection, and ABCB5 sFv-P complexed to MYC siRNA or controls will be administered on days 0, 1 and 3 after tumor implantation via tail vein injection (80 µg siRNA in an injection volume of 100 µl at a molar ratio of ABCB5 sFv-P/total siRNA of 1:6) to murine recipients of human melanoma cell xenografts randomized on day 0 following xenotransplantation into the following treatment and control groups (n=10 replicate animals for each melanoma cell line and for each tumor cell specimen freshly isolated from each of n=10 primary melanomas and n=10 melanoma metastases, xenografted s.c. to NOD-SCID mice or intradermally to human skin/Rag2−/− mice chimera): 1) ABCB5 mAb/gelonin 500 µg/mouse i.v. q.o.d. starting at day 0; 2) isotype control mAb/gelonin 500 µg/mouse i.v. q.o.d. starting at day 0; 3) ABCB5 sFv/gelonin 500 µg/mouse i.v. q.o.d. starting at day 0; 4) control sFv/gelonin 500 µg/mouse i.v. q.o.d. starting at day 0; 5) ABCB5 sFv-P/MYC siRNA i.v. on days 0, 1 and 3; 6) ABCB5 sFv-P/control siRNA i.v. on days 0, 1 and 3; 7) ABCB5 sFv-P i.v. on days 0, 1 and 3. The treatment protocol is summarized in Table 2:

TABLE 2

| Group | No. mice | Treatment |
|---|---|---|
| 1 | 10 | ABCB5 mAb/gelonin 500 µg/mouse i.v. q.o.d. starting at day 0 |
| 2 | 10 | isotype control mAb/gelonin 500 µg/mouse i.v. q.o.d. starting at day 0 |

TABLE 2-continued

| Group | No. mice | Treatment |
|---|---|---|
| 3 | 10 | ABCB5 sFv/gelonin 500 µg/mouse i.v. q.o.d. starting at day 0 |
| 4 | 10 | control sFv/gelonin 500 µg/mouse i.v. q.o.d. starting at day 0 |
| 5 | 10 | ABCB5 sFv-P/MYC siRNA i.v. on days 0, 1 and 3 |
| 6 | 10 | ABCB5 sFv-P/control siRNA i.v. on days 0, 1 and 3 |
| 7 | 10 | ABCB5 sFv-P i.v. on days 0, 1 and 3 |

In a second set of experiments aimed at assessing the effects of immunotoxins (ABCB5 mAb/gelonin or sFv/gelonin) or of ABCB5 sFv-P/MYC siRNA on tumor progression of established tumors, murine recipients of human melanoma cell xenografts will be randomized on day 7 following xenotransplantation (when tumors are established) into the treatment and control groups summarized in Table 7 (n=10 replicate animals for each melanoma cell line and for each tumor cell specimen freshly isolated from each of n=10 primary melanomas and n=10 melanoma metastases, xenografted s.c. to NOD-SCID mice or intradermally to human skin/Rag2−/− mice chimera):

TABLE 3

| Group | No. mice | Treatment |
|---|---|---|
| 8 | 10 | ABCB5 mAb/gelonin 500 µg/mouse i.v. q.o.d. starting at day 7 |
| 9 | 10 | isotype control mAb/gelonin 500 µg/mouse i.v. q.o.d. starting at day 7 |
| 10 | 10 | ABCB5 sFv/gelonin 500 µg/mouse i.v. q.o.d. starting at day 7 |
| 11 | 10 | control sFv/gelonin 500 µg/mouse i.v. q.o.d. starting at day 7 |
| 12 | 10 | ABCB5 sFv-P/MYC siRNA i.v. on days 7, 8 and 10 |
| 13 | 10 | ABCB5 sFv-P/control siRNA i.v. on days 7, 8 and 10 |
| 14 | 10 | ABCB5 sFv-P i.v. on days 7, 8 and 10 |

Clinical tumor formation/growth will be assayed daily as a time course by determination of tumor volume (TV) according to the established formula [TV (mm3)=π/6×0.5×length×(width)2] for the length of the experiment (45 days). Statistically significant differences in tumor formation as a function of the applied treatment regimen will be assessed using the Fisher's Exact test. Differences in tumor volumes between experimental groups will be determined using nonparametric ANOVA. Two-tailed P values<0.05 will be considered statistically significant. Immunofluorescent and immunohistochemical analysis of each transplanted tumor xenograft dissected from animals of all treatment groups sacrificed initially on day 45 of the experiment (sequential sacrifices [e.g. at days 10, 20, 30, and 45] will be performed based on the day 45 findings, and in addition to examination of primary tumors, sacrificed animals will be necropsied, all metastases evaluated, and all tissues pathologically evaluated for evidence of toxicity mediated by the applied treatment regimen). Expression of ABCB5 and co-expression of ABCB5 with CD133 will be assayed by sequential HRP/AP-immunoenzymatic double staining of frozen melanoma xenograft sections as previously described. Tumor sections will be analyzed by brightfield microscopy, and mean percentages of cells staining positive for each marker will be semiquantitatively (no positivity: −; <10% positivity: +; 10-50% positivity: ++; >50% positivity: +++) classified based on cell counting in three microscopy fields (400× magnification) for each staining condition as previously described. Using fluorescent microscopy and separate filters for each fluorochrome, RFP-positive cells (ABCB5+ origin) and GFP-positive cells (ABCB5-origin) will be counted (100 cells/sample) and RFP/GFP cell ratios within each tumor will be calculated. Mean ratios derived from replicate animals subjected to each treatment regimen will be statistically compared using nonparametric ANOVA. To assess efficacy of ABCB5+ targeting strategies, apoptotic melanoma cells growing in the murine subcutis, human skin xenografts, and at sites of metastasis will be identified according to established criteria used for light microscopy and confirmed by the TUNEL assay. We will also screen immunohistochemically for protein expression relevant to apoptotic pathways, including Bax, Bcl-2, and Bcl-XL. Finally these results will be correlated with a screen for cell proliferation-related markers (MIB-1, PCNA, and cyclin D1/D3). Positive cells will be enumerated manually over cross-sectional profiles, and by the use of computer-assisted imaging programs available in the co-PI's laboratory (GFM) that should significantly enhance efficiency of quantitation.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of delivering a therapeutic agent to an intracellular compartment of a cell, comprising:
contacting a cell with an isolated antibody or peptide that selectively binds to ABCB5 conjugated to a therapeutic agent in an effective amount to deliver the therapeutic agent to an intracellular compartment of the cell.

2. The method of claim 1, wherein the isolated peptide is an antibody or antigen binding fragment thereof.

3. The method of claim 1, wherein the therapeutic agent is a toxin.

4. The method of claim 1, wherein the therapeutic agent is an siRNA.

5. The method of claim 1, wherein the therapeutic agent is a chemotherapeutic agent.

6. The method of claim 1, wherein the therapeutic agent is a therapeutic antibody.

7. A method of delivering a therapeutic agent to an intracellular compartment of a cell, comprising: contacting a cell with an isolated antibody or peptide that selectively binds to ABCB5 conjugated to a therapeutic agent in an effective amount to deliver the therapeutic agent to an intracellular compartment of the cell, further comprising contacting a cell with an isolated molecule that selectively binds to a surface marker selected from the group consisting of 25 CD49e, CD133, and CD166.

8. A method of delivering a therapeutic agent to an intracellular compartment of a cell, comprising: contacting a cell with an isolated antibody or peptide that selectively binds to ABCB5 conjugated to a therapeutic agent in an effective amount to deliver the therapeutic agent to an intracellular compartment of the cell, further comprising contacting a cell with an isolated molecule that selectively binds to a surface marker selected from the group consisting of BMPR1a, TIE-1, VE-cadherin (CD144) and nestin.

9. A method for treating a subject, comprising systemically administering an isolated peptide that selectively binds to ABCB5 and comprises an amino acid sequence having SEQ ID NO: 1 (heavy chain variable region) and SEQ ID NO:2 (light chain variable region) or having the following 6 CDRs: SEQ ID NO:3 (CDR-H1), SEQ ID NO:4 (CDR-H2), SEQ ID NO:5 (CDR-H3), SEQ ID NO:6 (CDR-L1), SEQ ID NO:7 (CDR-L2), or SEQ ID NO:8 (CDR-L3), to a subject having cancer in an effective amount to treat the cancer.

10. A method for treating a subject, comprising administering a composition comprising an isolated peptide having 6 CDRs that selectively bind to ABCB5 wherein the isolated peptide comprises SEQ ID NO: 1 (heavy chain variable region) and SEQ ID NO:2 (light chain variable region) or has the following 6 CDRs: SEQ ID NO:3 (CDR-H1), SEQ ID NO:4 (CDR-H2), SEQ ID NO:5 (CDR-H3), SEQ ID NO:6 (CDR-L1), SEQ ID NO:7 (CDR-L2), or SEQ ID NO:8 (CDR-L3), wherein the isolated peptide is not mAb 3C2-1D12 to a subject having cancer in an effective amount to treat the cancer.

11. A method for treating a subject, comprising administering an isolated peptide that selectively binds to ABCB5 and comprises an amino acid sequence having 6 CDRs wherein the isolated peptide comprises SEQ ID NO: 1 (heavy chain variable region) and SEQ ID NO:2 (light chain variable region) or has the following 6 CDRs: SEQ ID NO:3 (CDR-H1), SEQ ID NO:4 (CDR-H2), SEQ ID NO:5 (CDR-H3), SEQ ID NO:6 (CDR-L1), SEQ ID NO:7 (CDR-L2), or SEQ ID NO:8 (CDR-L3), and a chemotherapeutic agent, to a subject having cancer in an effective amount to treat the cancer.

12. A method for treating a subject, comprising systemically administering an isolated antibody or antibody fragment that selectively binds to ABCB5 and a chemotherapeutic agent to a subject having cancer in an effective amount to treat the cancer.

* * * * *